(12) United States Patent
Kawano et al.

(10) Patent No.: US 7,960,683 B2
(45) Date of Patent: Jun. 14, 2011

(54) OBSERVATION APPARATUS AND OBSERVATION METHOD WITH REFLECTED LIGHT PATTERNS BEING DETECTED BY CHANGING A WEIGHT FOR EACH OF ELEMENT LIGHTS

(75) Inventors: Hironao Kawano, Machida (JP); Ryoji Sato, Hino (JP); Hironobu Takizawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 136 days.

(21) Appl. No.: 12/547,206

(22) Filed: Aug. 25, 2009

(65) Prior Publication Data

US 2010/0032546 A1 Feb. 11, 2010

Related U.S. Application Data

(63) Continuation of application No. PCT/JP2008/053187, filed on Feb. 25, 2008.

(30) Foreign Application Priority Data

Feb. 26, 2007 (JP) .................................. 2007-046014

(51) Int. Cl.
*G01J 3/50* (2006.01)
(52) U.S. Cl. ..................................... 250/226; 250/208.1
(58) Field of Classification Search .................. 250/226, 250/208.1, 559.4; 600/323–340, 473, 480, 600/102–118; 382/162–167
See application file for complete search history.

(56) References Cited

U.S. PATENT DOCUMENTS

| 5,045,704 A | * | 9/1991 | Coates ........................... 250/372 |
| 5,142,359 A | | 8/1992 | Yamamori |
| 2007/0270641 A1 | | 11/2007 | Kimoto et al. |

FOREIGN PATENT DOCUMENTS

| EP | 1 880 657 A1 | 1/2008 |
| EP | 1 908 393 A1 | 4/2008 |
| JP | 08-111812 | 4/1996 |
| JP | 2003-093336 | 4/2003 |
| JP | 2004-167008 | 6/2004 |
| JP | 2006-314808 | 11/2006 |
| JP | 2006-341078 | 12/2006 |
| JP | 2006-345947 | 12/2006 |
| WO | WO 2006/040831 A1 | 4/2006 |
| WO | WO 2007/013245 A1 | 2/2007 |

OTHER PUBLICATIONS

Extended Supplementary European Search Report dated Feb. 3, 2010.

* cited by examiner

*Primary Examiner* — Que T Le
(74) *Attorney, Agent, or Firm* — Scully, Scott, Murphy & Presser, P.C.

(57) ABSTRACT

An observation apparatus includes a light radiating unit that radiates a plurality of element lights, each of which has a limited wavelength band, to an observation target; a light detecting unit that detects the plurality of element lights reflected by the observation target in a plurality of patterns by changing a weight for each of the element lights; and a processing unit that performs a procedure of separating a component of each of the element lights from a plurality of detection results of the light detecting unit based on the weight for each of the element lights of the light detecting unit.

20 Claims, 37 Drawing Sheets

OBSERVATION APPARATUS AND OBSERVATION METHOD WITH REFLECTED LIGHT PATTERNS BEING DETECTED BY CHANGING A WEIGHT FOR EACH OF ELEMENT LIGHTS

CROSS-REFERENCE TO RELATED APPLICATIONS

This application is a continuation of PCT international application Ser. No. PCT/JP2008/053187 filed on Feb. 25, 2008 which designates the United States, incorporated herein by reference, and which claims the benefit of priority from Japanese Patent Application No. 2007-046014, filed on Feb. 26, 2007, incorporated herein by reference.

BACKGROUND OF THE INVENTION

1. Field of the Invention

The present invention relates to an observation apparatus and an observation method for capturing a spectral image of each color component based on a simultaneous method in order to observe an image of a subject.

2. Description of the Related Art

Conventionally, observation apparatuses have been proposed that radiate lights of plural types of wavelength band (that is, color lights of plural colors) onto a subject in order to capture a spectral image of each color component and to observe an image of the subject based on the captured spectral image of each color component. As an example of such an observation apparatus, a narrow-band-filter-equipped electronic endoscope system (Narrow Band Imaging: hereinafter, referred to as NBI) has particularly attracted attention in the field of endoscopes, in which a narrow band pass filer is used to narrow the wavelength band of an illumination light. In NBI, RGB color lights with their bands narrowed by a narrow band pass filter are sequentially radiated to a subject (for example, the inside of an organ of a subject), and a spectral image of each color component is captured based on a frame sequential method. Thus, NBI acquires an image of the subject. Such NBI was published by Sano, Yoshida, Kobayashi, et al. in the general conference of the Japan Gastroenterological Endoscopy Society held in October 2000. NBI enables an acquisition of an image with the fine structure of mucous membranes of a living body accurately extracted.

An observation apparatus, such as an image acquiring apparatus that uses the frame sequential method and is exemplified by NBI, sequentially acquires (captures) spectral images of color lights reflected from the subject every time the apparatus radiates illumination lights of color components, such as RGB, to the subject. Thus, when the observation apparatus that uses the frame sequential method acquires an image of one frame, a long exposure time (light-emitting time of illumination light) is required. Therefore, when the observation apparatus that uses the frame sequential method captures an image of a subject while moving or captures an image of a subject that is moving at high speed, the apparatus may acquire a blurred image. Also, it is difficult to increase the frame rate of the observation apparatus that uses the frame sequential method.

In addition to the frame sequential method described above, there is another imaging method for such an observation apparatus called a simultaneous method, in which spectral images are simultaneously captured. An observation apparatus that uses the simultaneous method generally has light-emitting units that emit respective color lights of plural colors, and a solid-state imaging element in which a color filter that separates a reflected light from a subject into color components, such as RGB, is formed on each pixel. The observation apparatus that uses the simultaneous method simultaneously radiates color lights, such as RGB, to a subject and simultaneously captures spectral images of the color components included in the reflected light from the subject in order to acquire an image of the subject. In the observation apparatus that uses the simultaneous method, the exposure time required to acquire an image of one frame is shorter compared with the frame sequential method. Therefore, the problem with the observation apparatus that uses the frame sequential method described above can be solved.

As an example of the observation apparatus that uses the simultaneous method, there is an electronic endoscope apparatus that performs a calculating process on a color image signal acquired by a solid-state imaging element without using a narrow band pass filter in order to generate a spectral image signal (refer to Japanese Patent Application Laid-open No. 2003-93336).

SUMMARY OF THE INVENTION

An observation apparatus according to an aspect of the present invention includes a light radiating unit that radiates a plurality of element lights, each of which has a limited wavelength band, to an observation target; a light detecting unit that detects the plurality of element lights reflected by the observation target in a plurality of patterns by changing a weight for each of the element lights; and a processing unit that performs a procedure of separating a component of each of the element lights from a plurality of detection results of the light detecting unit based on the weight for each of the element lights of the light detecting unit.

An observation method according to another aspect of the present invention includes simultaneously radiating a plurality of element lights, each of which has a limited wavelength band, to an observation target; measuring light amounts of the plurality of element lights reflected by the observation target in a plurality of patterns by changing a weight for each of the element lights; and separating a light amount of each of the element lights from the measured light amounts in the plurality of patterns based on the weight for each of the element lights used when measuring the light amount.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

In the following, preferred embodiments of an observation apparatus and observation method according to the present invention are described in detail with reference to the drawings. Embodiments of the present invention are described below by taking an image acquiring apparatus that acquires an image of the inside of an organ of a subject, such as a patient, (hereinafter, referred to as an in-vivo image) as an example of the observation apparatus according to the present invention, but the present invention is not limited by these embodiments.

First Embodiment

Figure 1:
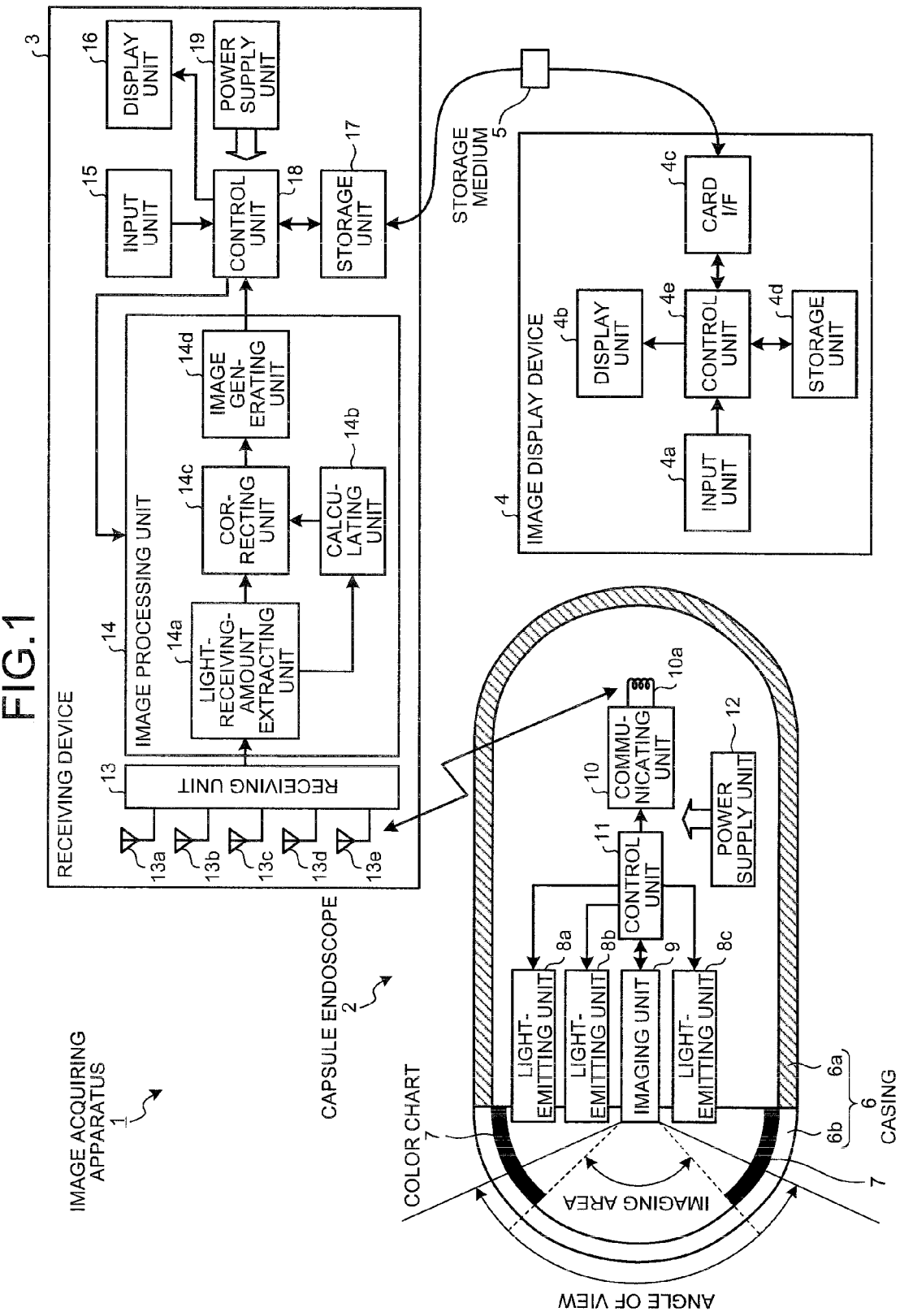
FIG. 1 is a block diagram schematically depicting a configuration example of an observation apparatus according to a first embodiment of the present invention.

FIG. 1 is a block diagram schematically depicting a configuration example of an image acquiring apparatus according to a first embodiment of the present invention. As depicted in FIG. 1, an image acquiring apparatus 1 according to the first embodiment is an example of an observation apparatus for acquiring an in-vivo image of a subject in order to observe the inside of the subject. The image acquiring apparatus 1 has a capsule endoscope 2 that captures an in-vivo image, a receiving device 3 that receives the in-vivo image captured by the capsule endoscope 2, an image display device 4 that displays the in-vivo image received by the receiving device 3, and a storage medium 5 for passing various information between the receiving device 3 and the image display device 4.

The capsule endoscope 2 simultaneously emits plural color lights to capture an in-vivo image or the like based on a simultaneous method of capturing a spectral image of each color component of a subject. Specifically, the capsule endoscope 2 has an imaging function based on a simultaneous method and a wireless communication function in a capsule casing, and is inserted into an organ of the subject. While moving by peristalsis or the like through the inside of the organ of the subject, the capsule endoscope 2 sequentially captures an in-vivo image or the like based on the simultaneous method at predetermined intervals (for example, at intervals of 0.5 seconds). The capsule endoscope 2 wirelessly transmits thus captured in-vivo image or the like in sequence to the receiving device 3 outside of the subject.

The receiving device 3 receives the image captured by the capsule endoscope 2. Specifically, the receiving device 3 has plural antennas disposed in a distributed manner on a body surface of the subject into which the capsule endoscope 2 is to be inserted, and is carried by the subject. Also, the receiving device 3 has the portable storage medium 5 removably inserted therein. The receiving device 3 sequentially receives in-vivo images or the like from the capsule endoscope 2 inside of the subject via the plural antennas, and sequentially stores the in-vivo images or the like in the inserted storage medium 5.

The image display device 4 has a configuration, such as that of a workstation that displays various information regarding the subject, such as in-vivo images captured by the capsule endoscope 2, on a display. Specifically, the image display device 4 has the storage medium 5 removably inserted therein, and acquires an in-vivo image from the receiving device 3 via the storage medium 5. The image display device 4 sequentially displays thus acquired in-vivo image on a display. A user, such as a doctor or nurse, observes the in-vivo image displayed on the display of the image display device 4 in order to examine the inside of the organ of the subject.

Next, the configuration of the capsule endoscope 2 included in the image acquiring apparatus 1 according to the first embodiment is described. As described above, the capsule endoscope 2 sequentially captures an in-vivo image as being inserted into an organ of the subject, and wirelessly transmits in sequence the acquired in-vivo image to the external receiving device 3. The capsule endoscope 2 has, as depicted in FIG. 1, in a capsule casing 6, plural light-emitting units 8a to 8c that illuminate a field of view to be captured, an imaging unit 9 that captures an image (in-vivo image) inside of an organ or the like illuminated by the light-emitting units 8a to 8c, a communicating unit 10 that wirelessly transmits the in-vivo images or the like captured by the imaging unit 9 to the outside, a control unit 11 that controls each component unit of the capsule endoscope 2, and a power supply unit 12 that supplies power to each component unit of the capsule endoscope 2.

The casing 6 is a capsule casing formed in dimension so as to be easily inserted into the organ of the subject, and is formed of a case main body 6a and an optical dome 6b. The case main body 6a has a cylindrical structure with its one end open and the other end closed in a dome shape, and contains each of the component units (the light-emitting units 8a to 8c, the imaging unit 9, the communicating unit 10, the control unit 11, and the power supply unit 12) of the capsule endoscope 2. The optical dome 6b is a transparent dome-shaped member, and is mounted at an open end of the case main body 6a. The optical dome 6b blocks the open end of the case main body 6a without hindering the field of view to be captured by the imaging unit 9. The casing 6 formed of these case main body 6a and the optical dome 6b contains the light-emitting units 8a to 8c, the imaging unit 9, the communicating unit 10, and the control unit 11, and the power supply unit 12, while ensuring water-tightness.

Also, at an end of the optical dome 6b, a color chart 7 is formed. The color chart 7 functions as a reflecting means that reflects element lights of plural colors forming a white light onto the imaging unit 9. Specifically, the color chart 7 has charts of the plural colors corresponding to the luminescent colors of the plural light-emitting units 8a to 8c, and is formed within the angle of view of the imaging unit 9 on the inner wall of the optical dome 6b and outside of a capturing area of an object (for example, the inside of an organ of the subject). When a white light is radiated by a simultaneous light emission of the light-emitting units 8a to 8c, the color chart 7 reflects element lights of the plural colors forming the white light onto the imaging unit 9. Here, color components of the element lights of the plural colors to be reflected from the color chart 7 onto the imaging unit 9 are identical to color components of plural color lights emitted from the light-emitting units 8a to 8c. Also, the color chart 7 has a white chart that reflects the white light and, when the white light is radiated by the simultaneous light emission of the light-emitting units 8a to 8c, reflects the white light together with the element lights of the plural colors described above onto the imaging unit 9.

The light-emitting units 8a to 8c illuminate an area (that is, the field of view to be captured by the imaging unit 9) within the angle of view of the imaging unit 9. Specifically, each of the light-emitting units 8a to 8c are constructed by using a light-emitting diode (LED) that emits a element light that forms a white light and an LED driving circuit that drives the LED. The light-emitting units 8a to 8c emit lights (color lights) of different color components and, with the simultaneous light emission of such color lights; output the white light. These light-emitting units 8a to 8c emit the plural color lights to the field of view to be captured by the imaging unit 9, thereby illuminating the object (for example, the inside of an organ of the subject) in the capturing area of the imaging unit 9 through the optical dome 6b and also illuminates the color chart 7 described above. Note the color chart 7 illuminated by these light-emitting units 8a to 8c reflects the element lights of the plural colors forming the white light onto the imaging unit 9. That is, these light-emitting units 8a to 8c and color chart 7 forms light output means that outputs the element lights of the plural colors that forms a white light onto the imaging unit 9.

Here, the plural color lights emitted from the light-emitting units 8a to 8c are element lights of the plural colors that forms a white light, and have color components corresponding to the charts of the plural colors of the color chart 7. Examples of such plural color lights include a red light with a red component (R), a green light with a green component (G), and a blue light with a blue component (B). For example, the light-emitting unit 8a emits a red light in a wavelength band $\Delta\lambda_1$ with a center wavelength $\lambda_1$, the light-emitting unit 8b emits a green light in a wavelength band $\Delta\lambda_2$ with a center wavelength $\lambda_2$, and the light-emitting unit 8c emits a blue light in a wavelength band $\Delta\lambda_3$ with a center wavelength $\lambda_3$.

Note that the wavelength band $\Delta\lambda_1$ of the red light is a wavelength band within a range of 610 nanometers to 780 nanometers, the wavelength band $\Delta\lambda_2$ of the green light is a wavelength band within a range of 500 nanometers to 570 nanometers, and the wavelength band $\Delta\lambda_3$ of the blue light is a wavelength band within a range of 380 nanometers to 460 nanometers. Each of these light-emitting units 8a to 8c desirably emits a color light of a narrow wavelength band. That is, these wavelength bands $\Delta\lambda_1$ to $\Delta\lambda_3$ are desirably narrowed to, for example, a wavelength band of 615 nanometers to 635 nanometers, a wavelength band of 530 nanometers to 550 nanometers, and a wavelength band of 390 nanometers to 445 nanometers, respectively.

The imaging unit 9 has a field of view to be captured on the optical dome 6b side of the casing 6, and captures an image in the field of view to be captured illuminated by the light-emitting units 8a to 8c based on the simultaneous method. Specifically, the imaging unit 9 is constructed by using an optical system that forms an optical image, a solid-state imaging element, such as a CCD or CMOS image sensor, and color filters of plural colors formed on each pixel of the solid-state imaging element. By receiving each of the color lights passing through the color filters of the plural colors, the imaging unit 9 captures a spectral image of each of the color components, such as RGB. In this case, the imaging unit 9 captures an image (for example, an in-vivo image) of the object within the capturing area through the optical dome 6b, and also captures an image of the charts of the plural colors (hereinafter, referred to as a chart image) included in the color chart 7 described above. The imaging unit 9 transmits image information containing a light-receiving-amount value of each pixel forming the captured image to the control unit 11. Examples of the image information include in-vivo image information containing a light-receiving-amount value of each color component forming the in-vivo image and chart image information containing a light-receiving-amount value of each color component forming a chart image.

Here, each of the plural color filters formed on each pixel of the imaging unit 9 is a color filter for each element light for letting the element light forming a white light pass through. That is, such plural color filters separate white light into each element light for passage. The element lights (color lights), which these plural color filters let pass through, correspond to color lights emitted from the light-emitting units 8a to 8c described above. Specifically, when the light-emitting units 8a to 8c emit a red light, a green light, and a blue light, respectively, the plural color filters of the imaging unit 9 are formed of a red filter FR for letting red light pass through, a green filter FG for letting green light pass through, and a blue filter FB for letting blue light pass through. These red filter FR, green filter FG, and blue filter FB are formed on each pixel of the imaging unit 9. In this case, the red filter FR, the green filter FG, and the blue filter FB are arranged based on a predetermined arrangement rule for each unit pixel group of the imaging unit 9. Here, the unit pixel group of the imaging unit 9 is formed of plural pixels that form one dot of a color image captured by the imaging unit 9.

The communicating unit 10 wirelessly transmits the image (for example, the in-vivo image and chart image) captured by the imaging unit 9 to the external receiving device 3. Specifically, the communicating unit 10 has a coil-shaped antenna 10a, performs a predetermined transmitting process, such as a modulating process, on an image signal received from the control unit 11, and generates a radio signal corresponding to the image signal. Note that the image signal received from the control unit 11 is a signal containing image information output from the imaging unit 9 described above. That is, the image signal contains a light-receiving-amount value of each color component forming the image captured by the imaging unit 9. The communicating unit 10 wirelessly transmits the radio signal corresponding to the image signal to the external receiving device 3 via the antenna 10a.

The control unit 11 controls each of the component units (the light-emitting units 8a to 8c, the imaging unit 9, and the communicating unit 10) of the capsule endoscope 2, and also controls inputs and outputs of signals among the component units. Specifically, the control unit 11 is constructed by using a CPU that performs various processes, a ROM having process programs or the like stored therein, and a RAM having various information temporarily stored therein. The control unit 11 controls light-emission driving timing of the light-emitting units 8a to 8c and capture-driving timing of the imaging unit 9 so that the imaging unit 9 captures an in-vivo image and a chart image based on the simultaneous method. In this case, the control unit 11 controls the light-emitting units 8a to 8c so that they simultaneously emit RGB color lights, and controls the imaging unit 9 so that it captures an image of the inside of the organ of the subject illuminated by the light-emitting units 8a to 8c and an image of the color chart 7.

Also, whenever acquiring image information from the imaging unit 9, the control unit 11 generates an image signal containing the image information, and transmits the generated image signal to the communicating unit 10. The control unit 11 controls the communicating unit 10 so that it wirelessly transmits the image signal containing the image information to the external receiving device 3.

The power supply unit 12 is constructed by using a button battery, such as a silver-oxide battery, and a switch circuit and supplies power to each component unit of the capsule endoscope 2. The switch circuit of the power supply unit 12 is constructed by using, for example, a reed switch that switches an ON/OFF state of power supply by an external magnetic force. When being switched to an ON state by an external magnetic force, the power supply unit 12 supplies power to the light-emitting units 8a to 8c, the imaging unit 9, the communicating unit 10, and the control unit 11.

Next, the configuration of the receiving device 3 included in the image acquiring apparatus 1 according to the first embodiment is described. As described above, the receiving device 3 is carried by the subject and receives an image captured by the capsule endoscope 2 (in detail, the imaging unit 9). Also, the receiving device 3 sequentially stores the received in-vivo image in the storage medium 5. The receiving device 3 has, as depicted in FIG. 1, a receiving unit 13 that receives image information about an in-vivo image or the like through plural antennas 13a to 13e disposed in a distributed manner on a body surface of the subject, and an image processing unit 14 that performs various correcting processes on the in-vivo image based on the image information received by the receiving unit 13. Also, the receiving device 3 has an input unit 15, a display unit 16 that displays specific information about the subject or the like, a storage unit 17 that stores in-vivo images or the like, a control unit 18 that controls each component unit of the receiving device 3, and a power supply unit 19 that supplies power to each component unit of the receiving device 3.

The receiving unit 13 has the plural antennas 13a to 13e and receives image information from the capsule endoscope 2 via these antennas 13a to 13e. Specifically, the antennas 13a to 13e are, for example, loop antennas, disposed in a distributed manner on the body surface of the subject into which the capsule endoscope 2 is to be inserted in an organ. Via these antennas 13a to 13e on the body surface, the receiving unit 13 sequentially receives a radio signal from the capsule endoscope 2 inserted in the organ of the subject. The receiving unit 13 performs a receiving process, such as a demodulating process, on thus received radio signal from the capsule endoscope 2 to demodulate the radio signal to an image signal. The image signal contains the in-vivo image information and chart image information described above. In this manner, the receiving unit 13 receives the image information from the capsule endoscope 2. The receiving unit 13 transmits the image signal containing the image information to the image processing unit 14. Note that the receiving unit 13 has one or more reception antenna, and the number of reception antennas included in the receiving unit 13 is not particularly restricted to five.

The image processing unit 14 performs various correcting processes on the in-vivo image received from the receiving unit 13, and generates and outputs a corrected in-vivo image. Specifically, the image processing unit 14 receives the image signal from the receiving unit 13 to acquire the in-vivo image information and chart image information contained in the received image signal. The image processing unit 14 uses the chart image information to perform various correcting processes on the in-vivo image. Further specifically, the image processing unit 14 corrects a color-mixture of the color components that occurs at component pixels of the in-vivo image due to mixture of an element light, which is to be received by the imaging unit 9 corresponding to the plural color filters formed on the respective pixels of the imaging unit 9, and other element lights. That is, based on the light-receiving-amount value of each color component forming the chart image, the image processing unit 14 calculates a color-mixture matrix M indicative of such a color-mixture state to find in advance an inverse matrix $M^{-1}$ of the color-mixture matrix M. Then, whenever acquiring in-vivo image information from the receiving unit 13, that is, whenever the imaging unit 9 of the capsule endoscope 2 captures an in-vivo image, the image processing unit 14 multiples each element light component forming the in-vivo image (that is, light-receiving-amount value of each color component forming the in-vivo image) by the inverse matrix $M^{-1}$. With this, the image processing unit 14 corrects the color-mixture state of each color component forming the in-vivo image. The image processing unit 14 calculates the color-mixture matrix M for each in-vivo image captured by the imaging unit 9 to find the inverse matrix $M^{-1}$, and sequentially corrects the color-mixture state of each in-vivo image as described above. Also, by using the inverse matrix $M^{-1}$, the image processing unit 14 calculates various correction coefficients and, by using the calculated correction coefficients, corrects a white balance, a gamma value, or the like of the in-vivo image. The image processing unit 14 sequentially generates an in-vivo image corrected through various correcting processes, and sequentially outputs an image signals containing the corrected in-vivo image to the control unit 18.

The image processing unit 14 has a light-receiving-amount extracting unit 14a that extracts in-vivo image information and chart image information contained in the image signal, a calculating unit 14b that calculates various correction coefficients including the inverse matrix $M^{-1}$ of the color-mixture matrix M described above, a correcting unit 14c that performs various correcting processes on the in-vivo image, and an image generating unit 14d that generates a corrected in-vivo image.

Whenever receiving an image signal from the receiving unit 13, the light-receiving-amount extracting unit 14a extracts chart image information contained in the received image signal, that is, a light-receiving-amount value of each color component forming the chart image captured by the imaging unit 9, and transmits the extracted chart image information to the calculating unit 14b. Also, whenever extracting the chart image information from the image signal, the light-receiving-amount extracting unit 14a transmits the image signal with the chart image information extracted therefrom to the correcting unit 14c.

Whenever receiving the chart image information from the light-receiving-amount extracting unit 14a, the calculating unit 14b calculates the color-mixture matrix M based on the received chart image information, and finds the inverse matrix $M^{-1}$ of the color-mixture matrix M. Specifically, the calculating unit 14b calculates the color-mixture matrix M by taking light-receiving-amount values of the color components forming the chart image as matrix elements. Matrix elements of color filters of the same color are arranged on the same row. Matrix elements of the same color light are arranged on the same column. Whenever calculating the color-mixture matrix M, the calculating unit 14b calculates the inverse matrix $M^{-1}$ of the color-mixture matrix M. Also, by using the inverse matrix $M^{-1}$, the calculating unit 14b calculates a white-balance correction coefficient, which is a correction coefficient for correcting the white balance of the in-vivo image, and a gamma value, which is a correction coefficient for gamma correction of the in-vivo image. Whenever receiving the chart image information, the calculating unit 14b transmits the inverse matrix $M^{-1}$ of the color-mixture matrix M, the white-balance correction coefficient, and gamma value to the correcting unit 14c.

Note that the matrix elements of color filters of the same color indicate light-receiving-amount values of color lights of the plural colors received by the pixels on which the color filters of the same color are formed. Those pixels are included in pixel groups forming chart images of the plural colors. Also, the matrix elements of the same color light indicate light-receiving-amount values of color light of the same color received by the pixels on which color filters of different colors are formed. Those pixels are included in the pixel groups forming chart images of the plural colors.

The correcting unit 14c performs various correcting processes on the in-vivo image captured by the imaging unit 9. Specifically, whenever receiving an image signal from the light-receiving-amount extracting unit 14a, the correcting unit 14c receives various correction coefficients corresponding to the image signal from the calculating unit 14b. Note that these various correction coefficients corresponding to the image signal include the inverse matrix $M^{-1}$ calculated by the calculating unit 14b based on the chart image information contained in the image signal (correction coefficient for a color-mixture correcting process), the white-balance correction coefficient calculated by the calculating unit 14b using the inverse matrix $M^{-1}$, and gamma value calculated by the calculating unit 14b using the inverse matrix $M^{-1}$. The correcting unit 14c acquires the in-vivo image information contained in the image signal received from the light-receiving-amount extracting unit 14a, and multiplies each element optical component forming the in-vivo image corresponding to the in-vivo image information (that is, the light-receiving-amount value of each color component forming the in-vivo image) by the inverse matrix $M^{-1}$. With this, the correcting unit 14c corrects the color-mixture state of each color component of the in-vivo image. Also, by using the light-receiving-amount value and white-balance correction coefficient of each color component forming the in-vivo image with the corrected color-mixture state, the correcting unit 14c corrects the white balance of the in-vivo image. Furthermore, by using the light-receiving-amount value and gamma value of each color component forming the in-vivo image with the corrected white balance, the correcting unit 14c performs gamma correction on the in-vivo image. Whenever completing the color-mixture correcting process, the white-balance correcting process, and the gamma correcting process on the in-vivo image, the correcting unit 14c transmits an image signal containing in-vivo image information corresponding to the corrected in-vivo image to the image generating unit 14d. Note that the in-vivo image information contains the light-receiving-amount value of each color component forming the corrected in-vivo image.

The image generating unit 14d generates and outputs the in-vivo image subjected to various correcting processes by the correcting unit 14c. Specifically, the image generating unit 14d receives the corrected in-vivo image information described above from the correcting unit 14c to acquire the light-receiving-amount value of each corrected color component contained in the in-vivo image information. Based on the light-receiving-amount value of each corrected color component, the image generating unit 14d generates the corrected in-vivo image. Furthermore, the image generating unit 14d performs mask processing to hide the chart image captured together with the in-vivo image. The image generating unit 14d transmits the generated corrected in-vivo image to the control unit 18.

The input unit 15 is constructed by using an input button or the like and inputs instruction information for instructing the control unit 18 to the control unit. Examples of the instruction information to be input by the input unit 15 to the control unit 18 include instruction information for making an instruction for the start of reception or the end of reception of a radio signal from the capsule endoscope 2.

The display unit 16 is constructed by using a liquid-crystal display or the like and displays various information to be displayed upon instruction from the control unit 18. Examples of the various information to be displayed by the display unit 16 include specific information about the subject carrying the receiving device 3 and information indicating that the in-vivo image of the subject is now being received. Note that examples of the specific information about the subject include a patient name and a patient ID that identify a subject.

The storage unit 17 stores the corrected in-vivo image described above. Specifically, the storage unit 17 has a structure in which the portable storage medium 5 can be removably inserted, and functions as a storage means for the in-vivo image when the storage medium 5 is inserted. The storage unit 17 sequentially stores the corrected in-vivo image to be stored upon instruction from the control unit 18. In this manner, the storage medium 5 in the storage unit 17 accumulates a corrected in-vivo image group. Note that the storage unit 17 may be configured to have a memory IC, such as a flash memory, so that the storage unit 17 itself stores information.

The control unit 18 controls each of the component units (the receiving unit 13, the image processing unit 14, the input unit 15, the display unit 16, and the storage unit 17) of the receiving device 3, and also controls inputs and outputs of signals among the component units. Specifically, the control unit 18 is constructed by using a CPU that performs various processes, a ROM having process programs or the like stored therein, and a RAM having various information temporarily stored therein. Based on instruction information input from the input unit 15, the control unit 18 controls a signal receiving operation of the receiving unit 13. The control unit 18 controls the image processing unit 14 so that it performs various correcting processes on the in-vivo image received by the receiving unit 13, and further controls the image processing unit 14 so that it generates and outputs the corrected in-vivo image. The control unit 18 sequentially acquires the corrected in-vivo image from the image processing unit 14 (specifically, the image generating unit 14d), and controls the storage unit 17 so that it sequentially stores the acquired corrected in-vivo image in the storage medium 5. When controlling the receiving unit 13 so that it starts receiving a radio signal from the capsule endoscope 2, the control unit 18 controls the display unit 16 so that it displays specific information about the subject into which the capsule endoscope 2 is inserted in the organ. Note that the control unit 18 reads the specific information about the subject from the storage medium 5 in the storage unit 17.

The power supply unit 19 is constructed by using a predetermined number of batteries and a power supply switch for switching an ON/OFF state of power supply. When switched to an ON state by the operation of the power supply switch, the power supply unit 19 supplies power to each of the component units (the receiving unit 13, the image processing unit 14, the input unit 15, the display unit 16, the storage unit 17, and the control unit 18) of the receiving device 3.

Next, the image display device 4 included in the image acquiring apparatus 1 according to the first embodiment is described. The image display device 4 acquires the corrected in-vivo image group via the storage medium 5, and displays the corrected in-vivo image group on a display. The image display device 4 has, as depicted in FIG. 1, an input unit 4a, a display unit 4b that displays the corrected in-vivo image or the like, a card interface (I/F) 4c in which the storage medium 5 can be removably inserted, a storage unit 4d that stores the corrected in-vivo image group, and a control unit 4e that controls each component unit of the image display device 4.

The input unit 4a is constructed by using an input device, such as a keyboard or mouse, and inputs various information to the control unit 4e. Examples of such various information to be input by the input unit 4a to the control unit 18 include instruction information to instruct the control unit 4e and the specific information about the subject as described above. Note that examples of the instruction information to instruct the control unit 4e include instruction information to make an instruction for taking in the corrected in-vivo image group in the storage medium 5 inserted in the card I/F 4c and instruction information to make an instruction for displaying the taken-in corrected in-vivo image group.

The display unit 4b is constructed by using a liquid-crystal display or the like, and displays various information to be displayed upon instruction from the control unit 4e. Examples of the various information to be displayed by the display unit 4b include the corrected in-vivo image group acquired via the storage medium 5 and specific information about a subject corresponding to the corrected in-vivo image group.

The card I/F 4c is an information input/output I/F for acquiring the corrected in-vivo image group via the storage medium 5. Specifically, the card I/F 4c has a structure of being able to removably insert the storage medium 5. Based on the control of the control unit 4e, the card I/F 4c reads the corrected in-vivo image group in the inserted storage medium 5, and transmits the read corrected in-vivo image group to the control unit 4e. In this manner, the corrected in-vivo image group is taken into the image display device 4. Also, based on the control of the control unit 4e, the card I/F 4c writes the specific information about the subject in the storage medium 5.

The storage unit 4d is constructed by using a large-capacity storage medium, such as a flash memory or hard disk. Based on the control of the control unit 4e, the storage unit 4d stores the corrected in-vivo image group taken in via the storage medium 5 inserted in the card I/F 4c. Note that the storage unit 4d may have a structure in which a portable storage medium, such as a CD or DVD, can be removably inserted, and the corrected in-vivo image group may be stored in the inserted storage medium.

The control unit 4e controls each of the component units (the input unit 4a, the display unit 4b, the card I/F 4c, and the storage unit 4d) of the image display device 4, and also controls inputs and outputs of signals among the component units. Specifically, the control unit 4e is constructed by using a CPU that performs various processes, a ROM having process programs or the like stored therein, and a RAM having various information temporarily stored therein. Based on instruction information input from the input unit 4a, the control unit 4e controls the card I/F 4c so that it takes in the corrected in-vivo image group in the storage medium 5. The control unit 4e acquires the corrected in-vivo image group via the card I/F 4c, and controls the storage unit 4d so that it stores the acquired corrected in-vivo image group. Also, based on instruction information input from the input unit 4a, the control unit 4e controls the display unit 4b so that it displays the acquired corrected in-vivo image group.

Figure 2A:
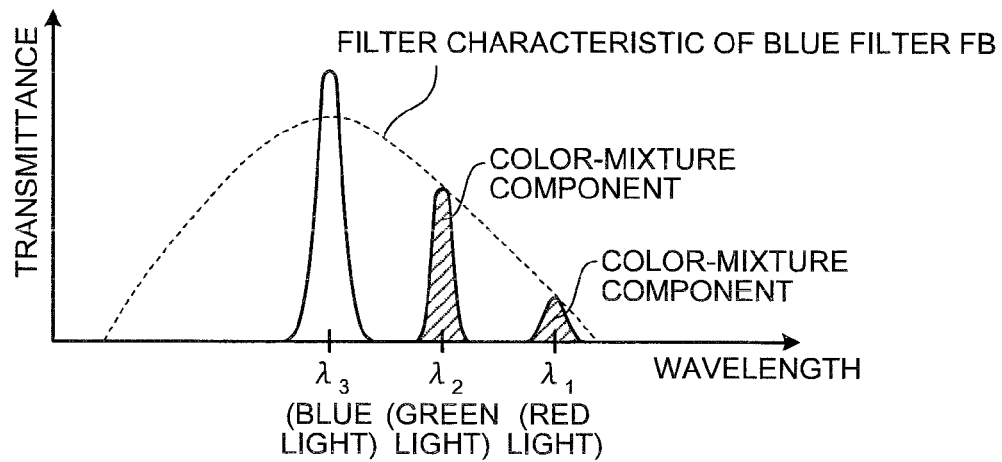
FIGS. 2A to 2C are schematic diagrams explaining light-receiving characteristics of an imaging unit in which RGB color filters are formed for each of pixels.
Figure 2B:
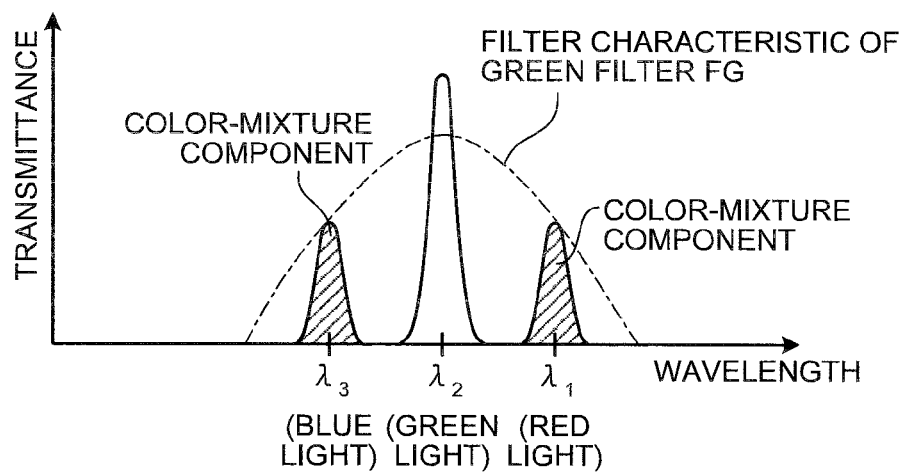
Figure 2C:
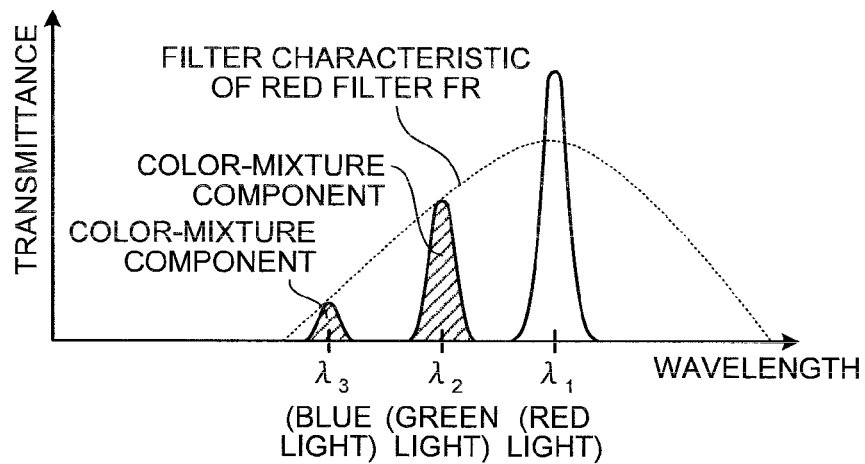

Next, a light-receiving characteristic of the imaging unit 9 of the capsule endoscope 2 is described. FIGS. 2A to 2C are schematic diagrams explaining the light-receiving characteristics of the imaging unit 9 in which RGB color filters are formed for each of pixels. As described above, any of the red filter FR, the green filter FG, and the blue filter FB is formed on each pixel of the imaging unit 9. The imaging unit 9 has the unit pixel group formed of a group of pixels. The group of pixels includes one or more pixel where the red filter FR is formed (hereinafter, referred to as an R component pixel), one or more pixel where the green filter FG is formed (hereinafter, referred to as a G component pixel), and one or more pixel where the blue filter FB is formed (hereinafter, referred to as a B component pixel). The imaging unit 9 has a structure in which plural such unit pixel groups are arranged in a matrix shape.

As depicted in FIGS. 2A to 2C, the red filter FR has a filter characteristic for passing a red light reflected from the field of view to be captured of the imaging unit 9. The green filter FG has a filter characteristic for passing a green light reflected from the field of view to be captured of the imaging unit 9. The blue filter FB has a filter characteristic for passing a blue light reflected from the field of view to be captured of the imaging unit 9.

Specifically, the red filter FR has a wide-range transmission wavelength band with a center wavelength approximately the same as the center wavelength $\lambda_1$ of the red light emitted from the light-emitting unit 8a, for reliably including the wavelength band $\Delta\lambda_1$ of the red light. In this case, the transmission wavelength band of the red filter FR includes the center wavelength $\lambda_2$ of a green light emitted from the light-emitting unit 8b and the center wavelength $\lambda_3$ of a blue light emitted from the light-emitting unit 8c. When receiving element lights of the respective RGB color components, the red filter FR that has such a transmission wavelength band lets the red light of the wavelength band $\Delta\lambda_1$ pass through at a high transmittance, while letting the green light of the wavelength band $\Delta\lambda_2$ and the blue light of the wavelength band $\Delta\lambda_3$ pass through at a lower transmittance compared with the transmittance of the red light.

The R component pixel where the red filter FR is formed receives an element light to be received corresponding to the red filter FR (that is, red light) and also other element lights not to be received by the red filter FR (that is, the green light and blue light). In this manner, a color-mixture state occurs at the R component pixel. In this case, the green light and blue light as opposed to the red light to be received corresponding to the red filter FR are color-mixture components in the R component pixel.

The green filter FG has a wide-range transmission wavelength band with a center wavelength approximately the same as the center wavelength $\lambda_2$ of the green light emitted from the light-emitting unit 8b, for reliably including the wavelength band $\Delta\lambda_2$ of the green light. In this case, the transmission wavelength band of the green filter FG includes the center wavelength $\lambda_1$ of a red light emitted from the light-emitting unit 8a and the center wavelength $\lambda_3$ of a blue light emitted from the light-emitting unit 8c. When receiving element lights of the respective RGB color components, the green filter FG that has such a transmission wavelength band lets the green light of the wavelength band $\Delta\lambda_2$ pass through at a high transmittance, while letting the red light of the wavelength band $\Delta\lambda_1$ and the blue light of the wavelength band $\Delta\lambda_3$ pass through at a lower transmittance compared with the transmittance of the green light.

The G component pixel where the green filter FG is formed receives an element light to be received corresponding to the green filter FG (that is, green light) and also other element lights not to be received by the green filter FG (that is, the red light and blue light). In this manner, a color-mixture state occurs at the G component pixel. In this case, the red light and blue light as opposed to the green light to be received corresponding to the green filter FG are color-mixture components in the R component pixel.

The blue filter FB has a wide-range transmission wavelength band with a center wavelength approximately the same as the center wavelength $\lambda_3$ of the blue light emitted from the light-emitting unit 8c, for reliably including the wavelength band $\Delta\lambda_3$ of the blue light. In this case, the transmission wavelength band of the blue filter FB includes the center wavelength $\lambda_1$ of red light emitted from the light-emitting unit 8a and the center wavelength $\lambda_2$ of green light emitted from the light-emitting unit 8b. When receiving element lights of the respective RGB color components, the blue filter FB that has such a transmission wavelength band lets the blue light of the wavelength band $\Delta\lambda_3$ pass through at a high transmittance, while letting the red light of the wavelength band $\Delta\lambda_1$ and the green light of the wavelength band $\Delta\lambda_2$ pass through at a lower transmittance compared with the transmittance of the blue light.

The B component pixel where the blue filter FB is formed receives an element light to be received corresponding to the blue filter FB (that is, blue light) and also other element lights not to be received by the blue filter FB (that is, red light and green light). In this manner, a color-mixture state occurs at the B component pixel. In this case, the red light and green light as opposed to the blue light to be received corresponding to the blue filter FB are color-mixture components in the B component pixel.

Here, when a color-mixture state occurs at each of the R component pixel, the G component pixel, and the B component pixel, the imaging unit 9 outputs, for each pixel, a light-receiving-amount value (hereinafter, referred to as a light-receiving-amount value of color-mixture state) including element lights to be received corresponding to the respective color filters (the red filter FR, the green filter FG, and the blue filter FB) and element lights of the color-mixture components. In this case, a light-receiving-amount output Sout output for each unit pixel group of the imaging unit 9 is represented by a matrix multiplication between the color-mixture matrix M described above and a light-receiving-amount output A in a non-color-mixture state, as expressed in the following Equation (1):

$$S_{out} = MA \quad (1)$$

Note that the light-receiving-amount output Sout represents a third-order column vector containing, as vector components, a light-receiving-amount value in a color-mixture state output correspondingly to the R component pixel in a color-mixture state, a light-receiving-amount value in a color-mixture state output correspondingly to the G component pixel in a color-mixture state, and a light-receiving-amount value in a color-mixture state output correspondingly to the B component pixel in a color-mixture state. Also, the light-receiving-amount output A in a non-color-mixture state represents a third-order column vector containing, as vector components, a light-receiving-amount value of only the R component to be output correspondingly to the R component pixel, a light-receiving-amount value of only the G component to be output correspondingly to the G component pixel, and a light-receiving-amount value of only the B component to be output correspondingly to the B component pixel.

Figure 3:
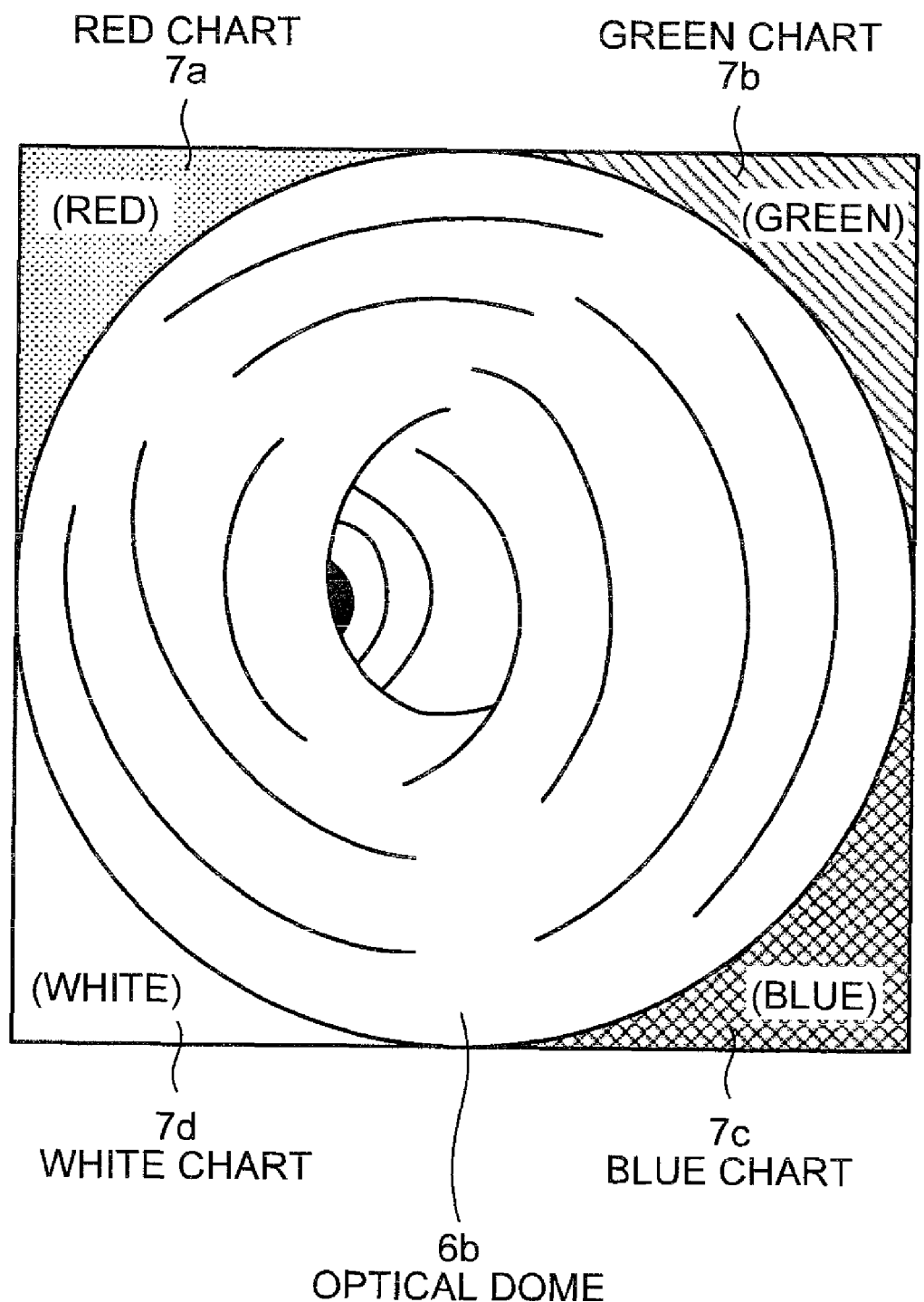
FIG. 3 is a schematic diagram depicting a configuration example of a color chart of plural colors formed in a region within an angle of view of the imaging unit.

Next, the color chart 7 formed on the optical dome 6b of the capsule endoscope 2 is described. FIG. 3 is a schematic diagram depicting a configuration example of the color chart 7 formed in a region within an angle of view of the imaging unit 9. Note that the color chart 7 depicted in FIG. 3 is viewed from the point of view of the imaging unit 9.

As depicted in FIG. 3, the color chart 7 has a red chart 7a of an R-component color chart, a green chart 7b of a G-component color chart, a blue chart 7c of a B-component color chart, and a white chart 7d of a white-component color chart. In the charts of the color components forming the color chart 7, the red chart 7a, the green chart 7b, and the blue chart 7c correspond to the respective luminescent colors (RGB) of the light-emitting units 8a to 8c or the respective color components (RGB) of the color filters formed on each pixel of the imaging unit 9. The red chart 7a, the green chart 7b, the blue chart 7c, and the white chart 7d are formed in the field of view to be captured by the imaging unit 9 on the inner wall surface of the optical dome 6b (that is, an area in an angle of view of the imaging unit 9) and outside of the capturing area for capturing an in-vivo image.

Specifically, the red chart 7a, the green chart 7b, the blue chart 7c, and the white chart 7d are formed in four corner areas of the area in the angle of view of the imaging unit 9 projected onto the inner wall surface of the optical dome 6b. In this case, the field of view to be captured of the imaging unit 9 inside of the organ of the subject (that is, the capturing area for capturing the in-vivo image) is secured in an inner side area surrounded by the red chart 7a, the green chart 7b, the blue chart 7c, and the white chart 7d.

The imaging unit 9 can view the inside of the organ of the subject through the optical dome 6b in the inner side area surrounded by the color chart 7, and receives reflected light from the subject (the inside of the organ) via the optical dome 6b in the inner side area. At the same time, the imaging unit 9 receives reflected light from the color chart 7. As a result, the imaging unit 9 captures chart images of the red chart 7a, the green chart 7b, the blue chart 7c, and the white chart 7d forming the color chart 7, together with the in-vivo image. In this case, the imaging unit 9 captures an original image containing the chart images of the respective color components and the in-vivo image in one frame.

Note that the original image is an image obtained by capturing an area in the angle of view of the imaging unit 9, and contains chart images of the red chart 7a, the green chart 7b, the blue chart 7c, and the white chart 7d in the four corner areas in one frame and also contains an in-vivo image in the inner side area surrounded by these chart images. The original image containing these chart images and the in-vivo image is received by the receiving device 3 over a radio signal from the capsule endoscope 2, as described above.

Figure 4:
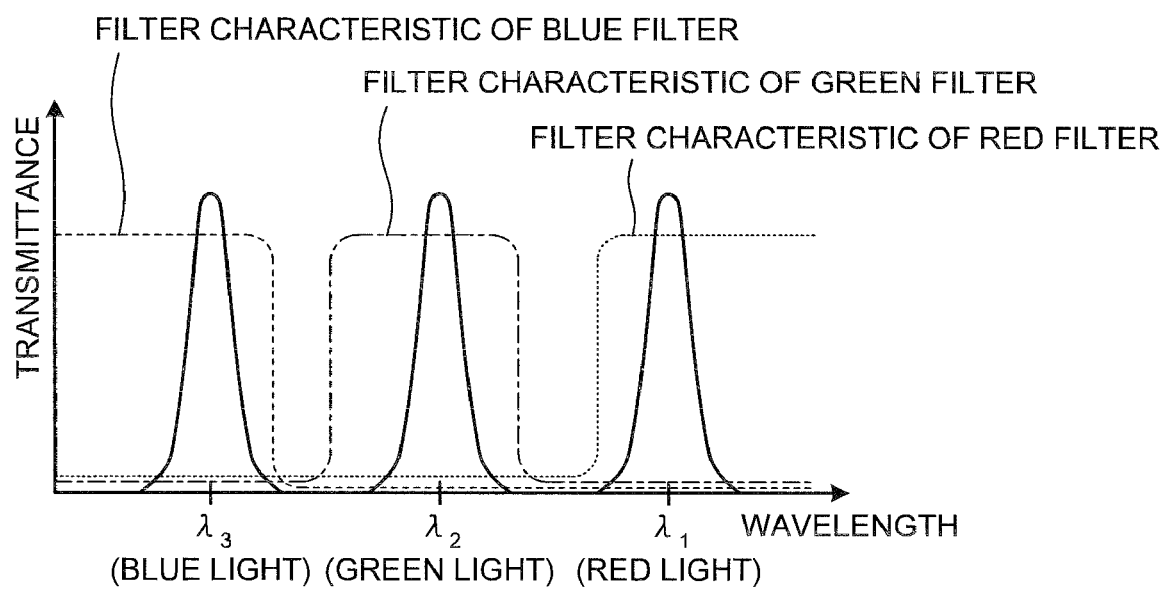
FIG. 4 is a schematic diagram exemplifying filter characteristics of charts of respective color components forming the color chart of the plural colors.

FIG. 4 is a schematic diagram exemplifying filter characteristics of charts of respective color components forming the color chart 7. As depicted in FIG. 4, the red chart 7a, the green chart 7b, and the blue chart 7c forming the color chart 7 function as reflecting means that reflect the red light, green light, and blue light, respectively.

The red chart 7a has a filter characteristic for selectively reflecting a red light in the RGB element lights forming a white light. Specifically, the red chart 7a has a reflective wavelength band including the wavelength band $\Delta\lambda_1$ of red light emitted from the light-emitting unit 8a. When RGB element lights forming a white light are emitted, the red chart 7a absorbs the green light and blue light of the element lights included in the white light, and reflects the remaining red light (red light of the wavelength band $\Delta\lambda_1$) to the imaging unit 9.

The green chart 7b has a filter characteristic for selectively reflection a green light in the RGB element lights forming a white light. Specifically, the green chart 7b has a reflective wavelength band including the wavelength band $\Delta\lambda_2$ of green light emitted from the light-emitting unit 8b. When RGB element lights forming a white light are emitted, the green chart 7b absorbs the red light and blue light of the element lights included in the white light, and reflects the remaining green light (green light of the wavelength band $\Delta\lambda_2$) to the imaging unit 9.

The blue chart 7c has a filter characteristic for selectively reflecting a blue light in the RGB element lights forming a white light. Specifically, the blue chart 7c has a reflective wavelength band including the wavelength band $\Delta\lambda_3$ of blue light emitted from the light-emitting unit 8c. When RGB element lights forming a white light are emitted, the blue chart 7c absorbs the red light and green light of the element lights included in the white light, and reflects the remaining blue light (blue light in the wavelength band $\Delta\lambda_3$) to the imaging unit 9.

Figure 5:
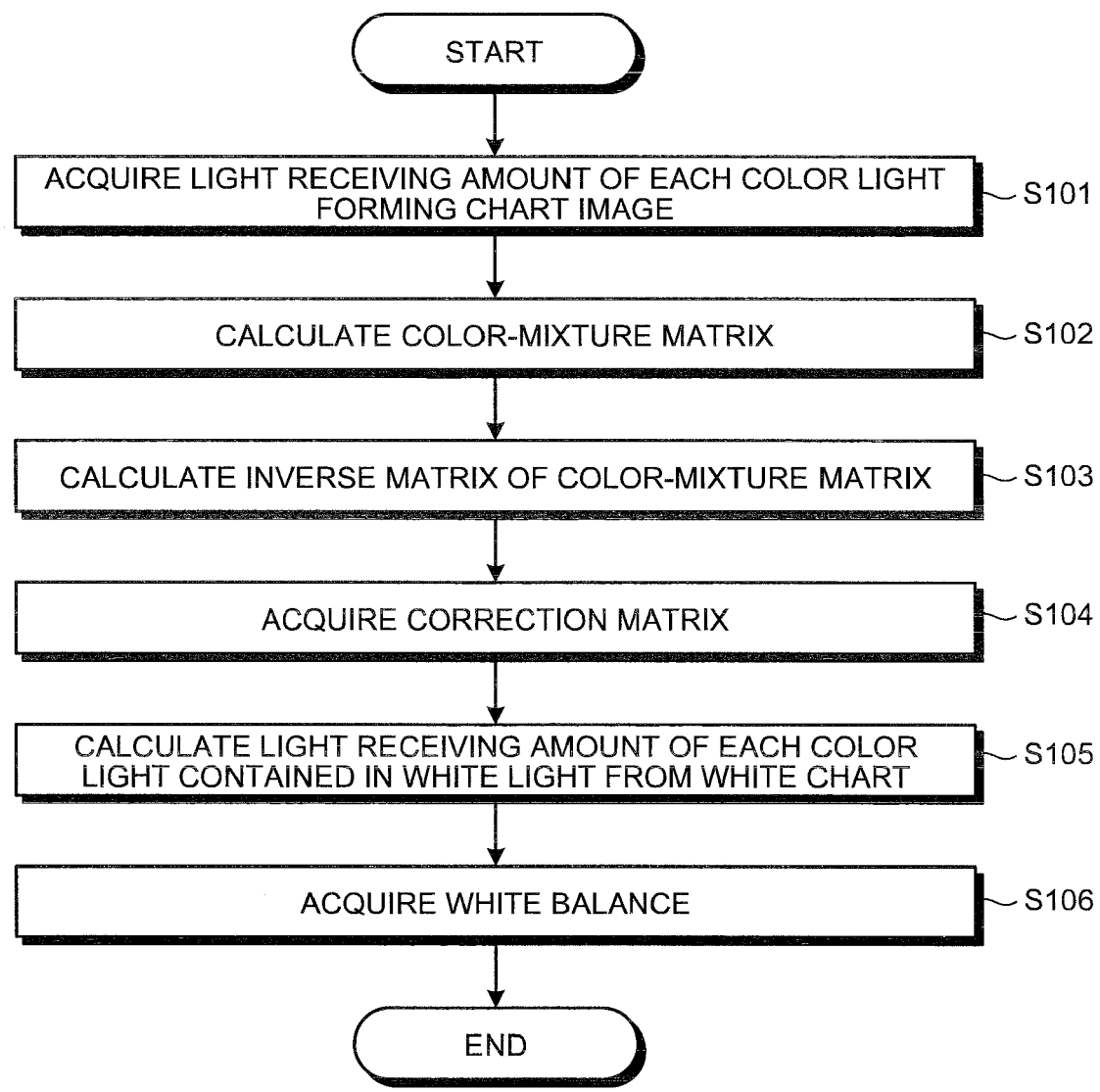
FIG. 5 is a flowchart exemplifying a process procedure until each correction coefficient of a color-mixture correcting process and a white-balance correcting process on an in-vivo image is acquired.

Next, the process procedure of the image processing unit 14 is described, which includes the procedure of calculating a correction coefficient for correcting a color-mixture state of the color components forming the in-vivo image (that is, the inverse matrix $M^{-1}$ of the color-mixture matrix M) and a white-balance correction coefficient for correcting the white balance of the in-vivo image. FIG. 5 is a flowchart exemplifying a process procedure until each correction coefficient of a color-mixture correcting process and a white-balance correcting process on the in-vivo image is acquired.

As depicted in FIG. 5, the image processing unit 14 receives an image signal from the receiving unit 13 and, based on the chart image information contained in the received image signal, acquires a light receiving amount of each color light forming the chart image (step S101). In this case, based on the chart image information extracted by the light-receiving-amount extracting unit 14a from the image signal, the calculating unit 14b acquires a light-receiving-amount output of each pixel group corresponding to each chart image in the color chart 7.

Specifically, the calculating unit 14b acquires a light-receiving-amount output $S_R$ of a pixel group corresponding to a chart image PR of the red chart 7a (that is, a red image), a light-receiving-amount output $S_G$ of a pixel group corresponding to a chart image PG of the green chart 7b (that is, a green image), and a light-receiving-amount output $S_B$ of a pixel group corresponding to a chart image PB of the blue chart 7c (that is, a blue image). Also, the calculating unit 14b acquires a light-receiving-amount output $S_W$ of a pixel group corresponding to a chart image PW of the white chart 7d (that is, a white image).

Here, the light-receiving-amount output $S_R$ represents a third-order column vector containing, as vector components, an average light-receiving-amount value of the red light received by the R-component pixel group, an average light-receiving-amount value of the red light received by the G-component pixel group, and an average light-receiving-amount value of the red light received by the B-component pixel group, in the pixel group corresponding to the red chart image PR. Also, the light-receiving-amount output $S_G$ represents a third-order column vector containing, as vector components, an average light-receiving-amount value of the green light received by the R-component pixel group, an average light-receiving-amount value of the green light received by the G-component pixel group, and an average light-receiving-amount value of the green light received by the B-component pixel group, in the pixel group corresponding to the green chart image PG. Furthermore, the light-receiving-amount output $S_B$ represents a third-order column vector containing, as vector components, an average light-receiving-amount value of the blue light received by the R-component pixel group, an average light-receiving-amount value of the blue light received by the G-component pixel group, and an average light-receiving-amount value of the blue light received by the B-component pixel group, in the pixel group corresponding to the blue chart image PB.

Note that the average light-receiving-amount value of the G-component pixel group and the average light-receiving-amount value of the B-component pixel group in the vector components contained in the light-receiving-amount output $S_R$, the average light-receiving-amount value of the R-component pixel group and the average light-receiving-amount value of the B-component pixel group in the vector components contained in the light-receiving-amount output $S_G$, and the average light-receiving-amount value of the R-component pixel group and the average light-receiving-amount value of the G-component pixel group in the vector components contained in the light-receiving-amount output $S_B$ are average light-receiving-amount values of color-mixture components.

The light-receiving-amount output $S_W$ described above represents a third-order column vector containing, as vector components, an average light-receiving-amount value of the R-component pixel group, an average light-receiving-amount value of the G-component pixel group, and an average light-receiving-amount value of the B-component pixel group, in the pixel groups corresponding to the white chart image PW. Note that the average light-receiving-amount value of the R-component pixel group, the average light-receiving-amount value of the G-component pixel group, and the average light-receiving-amount value of the B-component pixel group of the vector components of the light-receiving-amount output $S_W$ are average values of the light receiving amount in a color-mixture state output correspondingly to each pixel in a color-mixture state.

Next, the image processing unit 14 calculates the color-mixture matrix M based on the light-receiving-amount outputs of the respective pixel groups corresponding to the chart image of the respective color components described above (step S102). Specifically, the calculating unit 14b calculates the color-mixture matrix M by using the light-receiving-amount output $S_R$ of red light, the light-receiving-amount output $S_G$ of green light, and the light-receiving-amount output $S_B$ of blue light described above.

Here, between the light-receiving-amount outputs $S_R$, $S_G$, and $S_B$ and the color-mixture matrix M, relations expressed in the following Equations (2) to (4) hold:

$$S_R = M \begin{pmatrix} 1 \\ 0 \\ 0 \end{pmatrix} \tag{2}$$

$$S_G = M \begin{pmatrix} 0 \\ 1 \\ 0 \end{pmatrix} \tag{3}$$

$$S_B = M \begin{pmatrix} 0 \\ 0 \\ 1 \end{pmatrix} \tag{4}$$

Based on Equations (2) to (4), the calculating unit 14b can calculate the color-mixture matrix M. In this case, the color-mixture matrix M calculated by the calculating unit 14b is represented by the following Equation (5):

$$M = (k_1 S_R k_2 S_G k_3 S_B) \tag{5}$$

Note that constants $k_1$, $k_2$, and $k_3$ contained in the color-mixture matrix M in Equation (5) are predetermined constants determined by each of the light emission amounts of the light-emitting units 8a to 8c. Also, the color-mixture matrix M represented by Equation (5) is a third-order square matrix with three rows and three columns, and contains the vector components of the light-receiving-amount outputs $S_R$, $S_G$, and $S_B$ as matrix elements. Thus calculated color-mixture matrix M contains matrix elements of the same-color color filter in the same row and matrix elements of the same color light in the same column, as described above.

Then, the image processing unit 14 calculates the inverse matrix $M^{-1}$ of the color-mixture M calculated at step S102 (step S103), and acquires the calculated inverse matrix $M^{-1}$ as a correction matrix (step S104). In this case, the calculating unit 14b calculates the inverse matrix $M^{-1}$ of the color-mixture matrix M based on Equation (5), and acquires the calculated inverse matrix $M^{-1}$ as a correction matrix of a color-mixture correcting process on the in-vivo image (an example of a correction coefficient).

Next, the image processing unit 14 calculates a light receiving amount of each color light contained in the white light, which is a reflected light from the white chart 7d. That is, the light receiving amount of each RGB element light forming the white light (step S105) is calculated. In this case, the calculating unit 14b multiplies the light-receiving-amount output $S_W$ of the white light acquired at step S101 by the inverse matrix $M^{-1}$ calculated at step S103 (that is, the correction matrix for correcting a color-mixture state), thereby calculating a light-receiving-amount output W in a non-color-mixture state indicative a light receiving amount of each RGB element light forming the white light from the white chart 7d.

Note that the light-receiving-amount output W in the non-color-mixture state represents a third-order column vector containing, as vector components, an average light-receiving-amount value of the red light received by the R-component pixel group (R-component element light forming a white light), an average light-receiving-amount value of the green light received by the G-component pixel group (G-component element light forming a white light), and an average light-receiving-amount value of the blue light received by the B-component pixel group (B-component element light forming a white light). These pixel groups are included in the pixel group corresponding to the white chart image PW.

Here, any of the average light-receiving-amount value of the R-component pixel group, the average light-receiving-amount value of the G-component pixel group, and the average light-receiving-amount value of the B-component pixel group, which are vector components of the light-receiving-amount output $S_W$ of white light, represents a average light-receiving-amount value in a color-mixture state output corresponding to each pixel in the color-mixture state as described above. Therefore, between the light-receiving-amount output $S_W$, the color-mixture M, and the light-receiving-amount output W in the non-color-mixture state, a relation expressed by the following Equation (6) holds:

$$S_W = MW \quad (6)$$

Therefore, the calculating unit 14b multiplies the light-receiving-amount output $S_W$ by the inverse matrix $M^{-1}$ from the left, thereby calculating the light-receiving-amount output W in the non-color-mixture state as expressed in the following Equation (7):

$$W = M^{-1} S_W \quad (7)$$

When the light-receiving-amount output W in the non-color-mixture state is calculated at step S105, the image processing unit 14 acquires a white balance of the in-vivo image based on each vector component of the light-receiving-amount output W in the non-color-mixture state (step S106). Specifically, the calculating unit 14b acquires a white balance of the in-vivo image based on each vector component of the light-receiving-amount output W in the non-color-mixture state, that is, a ratio among the average light-receiving-amount value of the R-component element light forming the white light, the average light-receiving-amount value of the G-component element light forming the white light, and the average light-receiving-amount value of the B-component element light forming the white light. In this case, each vector component of the light-receiving amount output W in the non-color-mixture state is a white-balance correction coefficient for correcting the white balance of the in-vivo image.

Then, the calculating unit 14b transmits the thus acquired correction matrix (the inverse matrix $M^{-1}$ of the color-mixture matrix M) and white-balance correction coefficient (the light-receiving-amount output W in the non-color-mixture state) to the correcting unit 14c. Furthermore, the calculating unit 14b uses the inverse matrix $M^{-1}$ described above to calculate a gamma value (a correction coefficient for gamma correction on the in-vivo image), and transmits the calculated gamma value to the correcting unit 14c. The image processing unit 14 that has the calculating unit 14b repeats the process procedure at steps S101 to S106 described above for each in-vivo image captured by the imaging unit 9 of the capsule endoscope 2.

Figure 6:
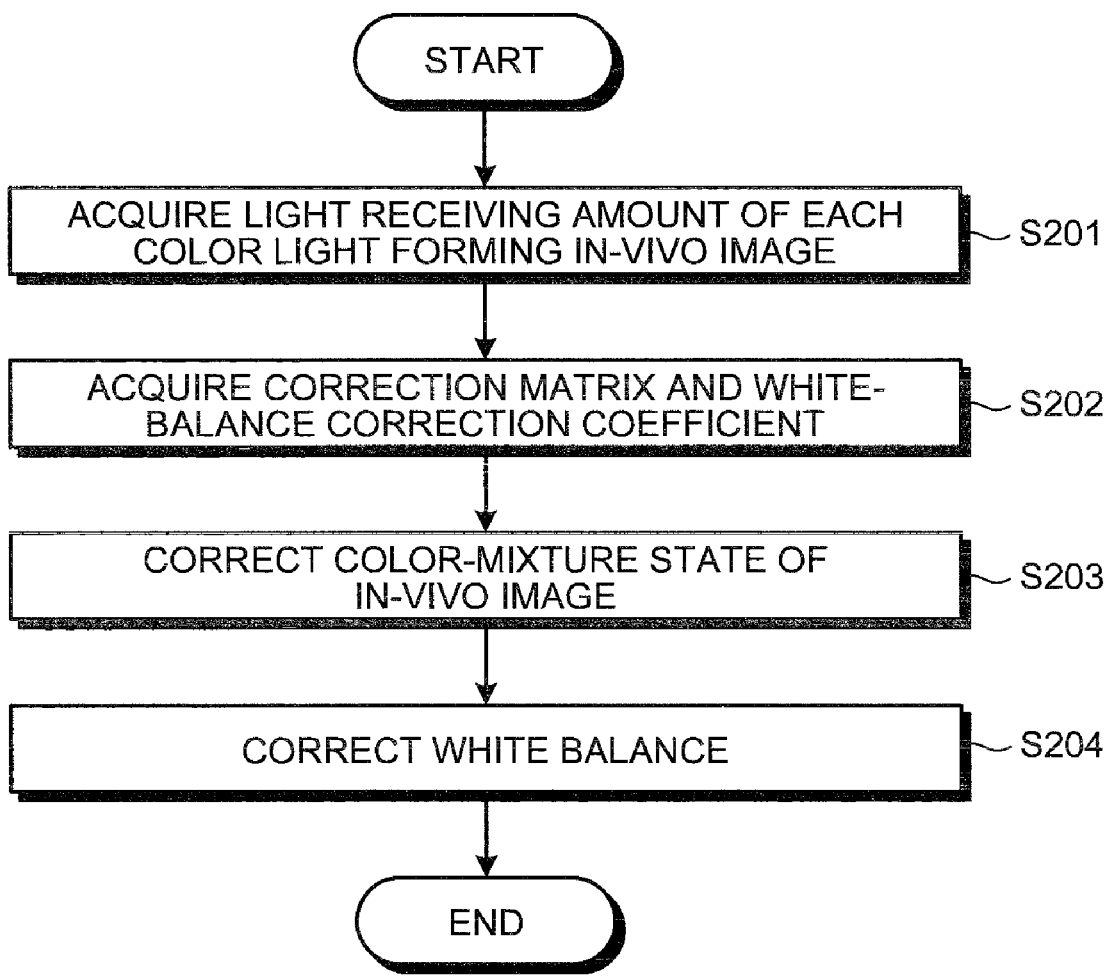
FIG. 6 is a flowchart exemplifying a process procedure until the color-mixture correcting process and the white-balance correcting process are performed on the in-vivo image.

Next, the process procedure of the image processing unit 14 is described, which includes the procedure performing a color-mixture correcting process and a white-balance correcting process on an in-vivo image. FIG. 6 is a flowchart exemplifying a process procedure until the color-mixture correcting process and the white-balance correcting process are performed on the in-vivo image.

As depicted in FIG. 6, the image processing unit 14 receives an image signal from the receiving unit 13 and, based on in-vivo image information contained in the received image signal, acquires a light receiving amount of each color light forming an in-vivo image (step S201). In this case, based on the in-vivo image information contained in the image signal received from the light-receiving-amount extracting unit 14a, the correcting unit 14c acquires the light-receiving-amount output Sout for each unit pixel group forming an in-vivo image. As described above, the light-receiving-amount output Sout is output for each unit pixel group forming an in-vivo image, and represents a third-order column vector containing, as vector components, each light-receiving-amount value (each light-receiving-amount value in a color-mixture state) of an R component pixel, a G component pixel, and a B component pixel contained in the unit pixel group.

Next, the image processing unit 14 acquires a correction matrix for correcting a color-mixture state of each color component of the in-vivo image corresponding to the in-vivo image information and a white-balance correction coefficient for correcting a white balance (step S202). In this case, the correcting unit 14c acquires, from the calculating unit 14b, the inverse matrix $M^{-1}$ of the color-mixture matrix M (the correction matrix in the color-mixture correcting process) and the light-receiving-amount output W in the non-color-mixture state (the white-balance correction coefficient) described above.

Then, the image processing unit 14 uses the correction matrix acquired at step S202 to correct the color-mixture state of the in-vivo image (step S203). In this case, the correcting unit 14c sequentially multiplies the light-receiving-amount output Sout of each unit pixel group acquired at step S201 by the inverse matrix $M^{-1}$, thereby correcting the color-mixture state of the in-vivo image.

Here, the light-receiving-amount output Sout of each unit pixel group is represented by a matrix multiplication between the color-mixture matrix M and the light-receiving-amount output A in the non-color-mixture state, as expressed in Equation (1) mentioned above. Therefore, the correcting unit 14c multiplies the light-receiving-amount output Sout by the inverse matrix $M^{-1}$ from the left, thereby calculating the light-receiving-amount output A in the non-color-mixture state. Thus calculated light-receiving-amount output A is obtained by removing the light-receiving-amount value of the color-mixture component from each vector component of the light-receiving-amount output Sout, and is a light-receiving-amount output for each unit pixel group when each pixel (each R component pixel, each G component pixel, and each B component pixel) forming the in-vivo image is in a non-color-mixture state. The correcting unit 14c repeats the multiplying process with the light-receiving-amount output Sout and the inverse matrix $M^{-1}$ for all unit pixel groups of in-vivo image groups. With this, the correcting unit 14c completes the color-mixture correcting process on the in-vivo image.

Next, by using the white-balance correction coefficient acquired at step S202, the image processing unit 14 corrects the white balance of the in-vivo image (step S204). In this case, the correcting unit 14c divides each vector component of the light-receiving-amount output A of the unit pixel group calculated at step S203 (that is, each of RGB light-receiving-amount values with a color-mixture component removed therefrom) by the white-balance correction coefficient (that is, each vector component of the light-receiving-amount output W). The correcting unit 14c repeats the dividing process with the light-receiving-amount output A and the white-balance correction coefficient for all unit pixel groups of the in-vivo image. With this, the correcting unit 14c completes the white-balance correcting process on the in-vivo image.

Then, the correcting unit 14c uses the gamma value calculated by the calculating unit 14b described above to perform a gamma correcting process on the in-vivo image. With this, the correcting unit 14c completes the color-mixture correcting process, the white-balance correcting process, and the gamma correcting process on an in-vivo image.

Figure 7:
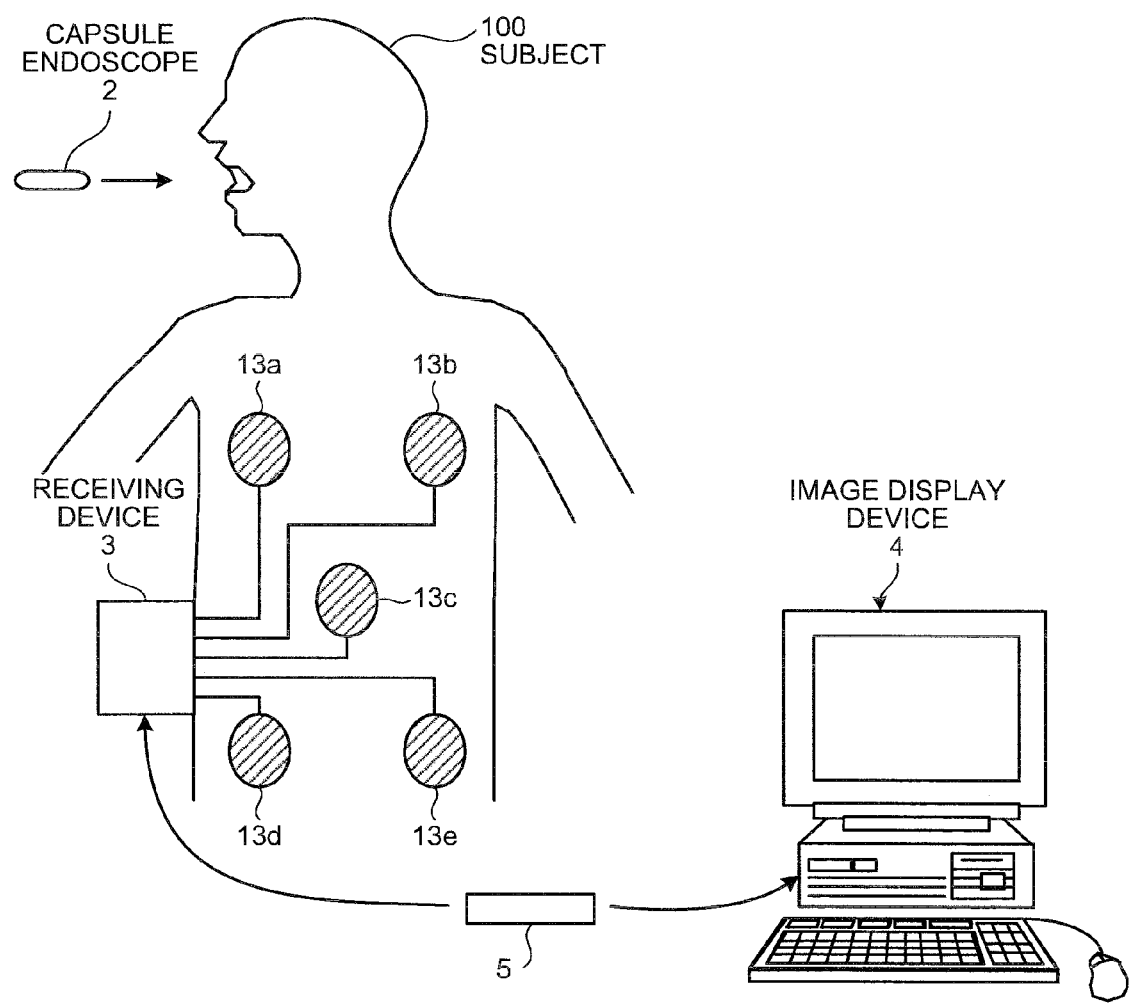
FIG. 7 is a schematic diagram exemplifying a specific mode of the observation apparatus that acquires an in-vivo image of a subject.
Figure 8:
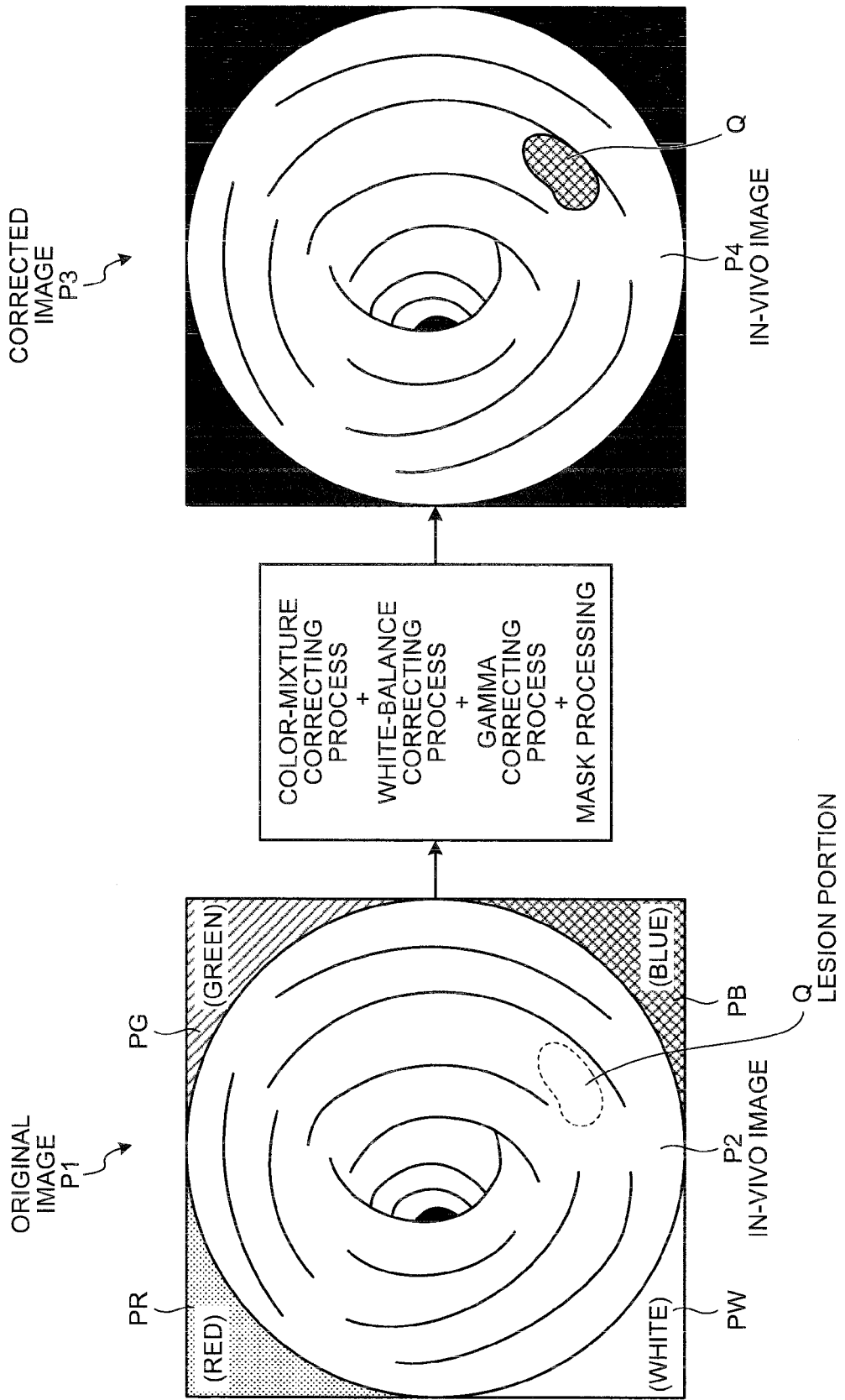
FIG. 8 is a schematic diagram explaining an operation of an image processing unit that generates and outputs the in-vivo image corrected based on an original image.

Next, the operation of the image processing unit 14 is described, which includes the operation of performing various correcting processes on an in-vivo image and generating and outputting the corrected in-vivo image. FIG. 7 is a schematic diagram exemplifying a specific mode of the image acquiring apparatus 1 that acquires an in-vivo image of a subject 100. FIG. 8 is a schematic diagram explaining the operation of the image processing unit 14 that generates and outputs the in-vivo image corrected based on an original image.

As depicted in FIGS. 7 and 8, the capsule endoscope 2 is inserted into an organ of the subject 100 by being swallowed from the mouth of the subject 100. The capsule endoscope 2 moves by peristalsis or the like through the inside of the organ of the subject 100, and also captures, at predetermined intervals, an original image P1 in which an in-vivo image P2 of the subject 100 and a chart image of the color chart 7 are contained in one frame. Note that the chart image of the color chart 7 is formed of, as described above, the chart image PR of the red chart 7a, the chart image PG of the green chart 7b, the charge image PB of the blue chart 7c, and the chart image PW of the white chart 7d.

The capsule endoscope 2 inside of the organ transmits, to the outside, a radio signal generated by performing a predetermined transmitting process on the image signal containing the original image P1. The receiving device 3 is carried by the subject 100, and receives the radio signal from the capsule endoscope 2 via the antennas 13a to 13e disposed in a distributed manner on a body surface of the subject 100. The receiving device 3 performs a predetermined receiving process on the radio signal to acquire the image signal.

The image processing unit 14 acquires the in-vivo image information and chart image information contained in the image signal. Based on the in-vivo image information, the image processing unit 14 acquires the light-receiving-amount output Sout of each unit pixel group forming the in-vivo image P2. Specifically, the image processing unit 14 acquires vector components of the light-receiving-amount output Sout, that is, a light-receiving-amount value $S_1$ of the R component pixel, a light-receiving-amount value $S_2$ of the G component pixel, and a light-receiving-amount value $S_3$ of the B component pixel. Note that any of these light-receiving-amount values $S_1$, $S_2$, and $S_3$ contains a light-receiving-amount value of a color-mixture component.

Based on the chart image information, the image processing unit 14 acquires the light-receiving-amount output $S_R$ of the pixel group corresponding to the chart image PR, the light-receiving-amount output $S_G$ of the pixel group corresponding to the chart image PG, the light-receiving-amount output $S_B$ of the pixel group corresponding to the chart image PB, and the light-receiving-amount output $S_W$ of the pixel group corresponding to the chart image PW.

Specifically, the image processing unit 14 acquires, as vector components of the light-receiving-amount output $S_R$, an average light-receiving-amount value $S_{11}$ of red light received by the R-component pixel group, an average light-receiving-amount value $S_{21}$ of red light received by the G-component pixel group, and an average light-receiving-amount value $S_{31}$ of red light received by the B-component pixel group. These pixel groups are included in the pixel group corresponding to the chart image PR. The image processing unit 14 acquires, as vector components of the light-receiving-amount output $S_G$, an average light-receiving-amount value $S_{12}$ of green light received by the R-component pixel group, an average light-receiving-amount value $S_{22}$ of green light received by the G-component pixel group, and an average light-receiving-amount value $S_{32}$ of green light received by the B-component pixel group. These pixel groups are included in the pixel group corresponding to the chart image PG. The image processing unit 14 acquires, as vector components of the light-receiving-amount output $S_B$, an average light-receiving-amount value $S_{13}$ of blue light received by the R-component pixel group, an average light-receiving-amount value $S_{23}$ of blue light received by the G-component pixel group, and an average light-receiving-amount value $S_{33}$ of blue light received by the B-component pixel group. These pixel groups are included in the pixel group corresponding to the chart image PB.

Note that, as represented in Equations (2) to (4) described above, between the light-receiving-amount outputs $S_R$, $S_G$, and $S_B$ containing these vector components and the color-mixture matrix M, relations expressed in the following Equations (8) to (10) hold:

$$\begin{pmatrix} S_{11} \\ S_{21} \\ S_{31} \end{pmatrix} = M \begin{pmatrix} 1 \\ 0 \\ 0 \end{pmatrix} \tag{8}$$

$$\begin{pmatrix} S_{12} \\ S_{22} \\ S_{32} \end{pmatrix} = M \begin{pmatrix} 0 \\ 1 \\ 0 \end{pmatrix} \tag{9}$$

$$\begin{pmatrix} S_{13} \\ S_{23} \\ S_{33} \end{pmatrix} = M \begin{pmatrix} 0 \\ 0 \\ 1 \end{pmatrix} \tag{10}$$

Also, the image processing unit 14 acquires, as vector components of the light-receiving-amount output $S_W$, an average light-receiving-amount value $S_{W1}$ of the R-component pixel group, an average light-receiving-amount value $S_{W2}$ of the G-component pixel group, and an average light-receiving-amount value $S_{W3}$ of the B-component pixel group. These pixel groups are included in the pixel group corresponding to the chart image PW.

The image processing unit 14 thus acquiring various light-receiving-amount outputs calculates the color-mixture matrix M based on Equations (5) and (8) to (10) mentioned above. In this case, the color-mixture matrix M calculated by the image processing unit 14 is represented by the following Equation (11):

$$M = \begin{pmatrix} k_1 S_{11} & k_2 S_{12} & k_3 S_{13} \\ k_1 S_{21} & k_2 S_{22} & k_3 S_{23} \\ k_1 S_{31} & k_2 S_{32} & k_3 S_{33} \end{pmatrix} \tag{11}$$

The image processing unit 14 calculates the inverse matrix $M^{-1}$ of the color-mixture matrix M expressed in Equation (11). The inverse matrix $M^{-1}$ calculated by the image processing unit 14 is a correction matrix of the color-mixture correcting process on the in-vivo image P2. In this manner, the image processing unit 14 acquires the correction matrix (the inverse matrix $M^{-1}$) of the color-mixture correcting process.

Also, based on Equation (6) mentioned above, the image processing unit 14 multiplies the light-receiving-amount output $S_W$ including the average light-receiving-amount values $S_{W1}$, $S_{W2}$, and $S_{W3}$ as vector components, and the inverse matrix $M^{-1}$ together to calculate the light-receiving-amount output W in the non-color-mixture state. The light-receiving-amount output W in the non-color-mixture state includes, as vector components, an average light-receiving-amount value $W_1$ of red light received by the R-component pixel group, an average light-receiving-amount value $W_2$ of green light received by the G-component pixel group, and an average light-receiving-amount value $W_3$ of blue light received by the B-component pixel group. These pixel groups are included in the pixel group corresponding to the chart image PW. Thus, the following Equation (12) holds.

$$\begin{pmatrix} W_1 \\ W_2 \\ W_3 \end{pmatrix} = M^{-1} \begin{pmatrix} S_{W1} \\ S_{W2} \\ S_{W3} \end{pmatrix} \quad (12)$$

These average light-receiving-amount values $W_1$, $W_2$, and $W_3$, which are vector components of the light-receiving-amount output W, are values calculated by removing the light-receiving-amount value of the color-mixture component from the average light-receiving-amount values $S_{W1}$, $S_{W2}$, and $S_{W3}$, which are vector components of the light-receiving-amount output $S_W$ in the color-mixture state. In this manner, the image processing unit 14 acquires a white balance of the in-vivo image P2 from a ratio among these average light-receiving-amount values $W_1$, $W_2$, and $W_3$. In this case, these average light-receiving-amount values $W_1$, $W_2$, and $W_3$ are white-balance correction coefficients.

The image processing unit 14 thus acquiring the correction matrix (the inverse matrix $M^{-1}$) and the white-balance correction coefficient (the average light-receiving-amount values $W_1$, $W_2$, and $W_3$) performs a color-mixture correcting process and a white-balance correcting process on the in-vivo image P2. Specifically, based on Equation (1) mentioned above, the image processing unit 14 sequentially multiplies the light-receiving-amount output Sout of all unit pixel groups forming the in-vivo image P2 by the inverse matrix $M^{-1}$, thereby sequentially calculating the light-receiving-amount output A in the non-color-mixture state for each unit pixel group.

The light-receiving-amount output A in the non-color-mixture state includes, as vector components, a light-receiving-amount value $a_1$ of only the R component obtained by removing the light-receiving amount value in the color-mixture state from the light-receiving-amount value $S_1$, a light-receiving-amount value $a_2$ of only the G component obtained by removing the light-receiving amount value in the color-mixture state from the light-receiving-amount value $S_2$, and a light-receiving-amount value $a_3$ of only the B component obtained by removing the light-receiving amount value in the color-mixture state from the light-receiving-amount value $S_3$. That is, the following Equation (13) holds. The image processing unit 14 acquires the light-receiving-amount output A expressed in the following Equation (13) for all unit pixel groups of the in-vivo image P2, thereby completing the color-mixture correcting process on the in-vivo image P2.

$$\begin{pmatrix} a_1 \\ a_2 \\ a_3 \end{pmatrix} = M^{-1} \begin{pmatrix} S_1 \\ S_2 \\ S_3 \end{pmatrix} \quad (13)$$

Next, the image processing unit 14 divides thus calculated light-receiving-amount values a1, a2, and a3, which are vector components of the light-receiving-amount output A in the non-color-mixture state, by the average light-receiving-amount values $W_1$, $W_2$, and $W_3$, respectively, which are white-balance correction coefficients. The image processing unit 14 repeats the dividing process with these light-receiving-amount output A and the white-balance correction coefficients for all unit pixel groups of the in-vivo image P2, thereby completing the white-balance correcting process on the in-vivo image P2. Then, the image processing unit 14 uses the gamma value calculated by the calculating unit 14b described above to perform gamma correction on the in-vivo image P2.

The image processing unit 14 performs various correcting processes on the in-vivo image P2 in this manner, thereby acquiring in-vivo image information about a corrected in-vivo image P4 with the color-mixture state, the white balance, or the like of the in-vivo image P2 being corrected. The in-vivo image information about the in-vivo image P4 includes a light-receiving-amount value $C_1$ of the R component, a light-receiving-amount value $C_2$ of the G component, and a light-receiving-amount value $C_3$ of the B component of each unit pixel group forming the in-vivo image P4. In this case, a light-receiving-amount output Cout including the light-receiving-amount values $C_1$, $C_2$, and $C_3$ of these RGB components as vector components is a light-receiving-amount output of each unit pixel forming the corrected in-vivo image P4, and is represented by the following Equation (14). Note that a constant k in the following Equation (14) is a desired constant for setting a luminance:

$$Cout = \begin{pmatrix} k\dfrac{a_1}{W_1} \\ k\dfrac{a_2}{W_2} \\ k\dfrac{a_3}{W_3} \end{pmatrix} \quad (14)$$

The image processing unit 14 generates the corrected in-vivo image P4 based on thus acquired light-receiving-amount output Cout of each unit pixel group. Furthermore, the image processing unit 14 performs mask processing of hiding the chart images PR, PG, PB, and PW contained in the original image P1. In this manner, the image processing unit 14 generates and outputs a corrected image P3 as depicted in FIG. 8. The corrected image P3 is an image that contains the corrected in-vivo image P4 with the chart images PR, PG, PB, and PW being deleted through the mask processing.

The corrected image P3 generated and output by the image processing unit 14 is acquired by the image display device 4 via the storage medium 5. The image display device 4 displays the corrected in-vivo image P4 contained in thus acquired the corrected image P3. The in-vivo image P4 displayed by the image display device 4 clearly depicts the state (such as color, size, and shape) of a lesion portion Q, which is unclear in the in-vivo image P2 before correction.

The image acquiring apparatus 1 that has the image processing unit 14 can acquire an in-vivo image with high color reproducibility capable of clearly depicting the state of a desired examination target, such as blood or a lesion portion, as exemplified by the in-vivo image P4. A user, such as a doctor or nurse, can reliably detect the desired examination target, such as blood or a lesion portion, based on the corrected in-vivo image acquired by the image acquiring apparatus 1, and can find a reflectance of each RGB color light (that is, each of the color lights of plural wavelength bands) for the desired examination target. As a result, the user can perform a detailed analysis of the desired examination target.

As described in the foregoing, in the first embodiment of the present invention, a color-mixture matrix is calculated indicative of a color-mixture state in which color lights to be received correspondingly to the color filters of plural colors formed on the respective pixels of the imaging unit and color lights of color-mixture components are mixed, and an inverse matrix of the color-mixture matrix is found in advance. When a desired object image, such as the inside of an organ of a subject, is captured, the light-receiving-amount output of each unit pixel group forming the object image is multiplied by the inverse matrix to correct the color-mixture state of the object image. Therefore, even without providing the imaging unit with a special filter allowing color light of a narrow wavelength band to pass through, color light of color-mixture components received by the imaging unit can be reliably eliminated when color lights of plural colors are simultaneously radiated to an object to capture an object image (that is, when a spectral image of each color component is captured based on the simultaneous method). As a result, image blurring due to the motion of the subject or the movement of the imaging unit can be reduced, and the capture frame rate can be increased. Also, a color mixture of the respective color components occurring when color lights of plural wavelength bands are simultaneously received can be corrected. Thus, an effect of providing an observation apparatus and observation method capable of acquiring an object image that is excellent in color reproducibility can be attained.

Also, the inverse matrix of the color-mixture matrix described above is calculated whenever an object image is captured together with the chart image of each color component, and the color-mixture state of each object image is corrected by using the inverse matrix of the color-mixture matrix calculated for each object image. Therefore, the color-mixture state of each object image can be reliably corrected without being influenced by a change in temperature or a change with time of the light-emitting characteristic of the light-emitting units that emit color lights of plural colors or being influenced by a change in temperature or a change with time of the light-receiving characteristic of the imaging unit.

Furthermore, the white-balance correction coefficient is calculated by using thus calculated inverse matrix of the color-mixture matrix. Therefore, the white-balance correction coefficient with the color-mixture components being removed can be acquired. By using the white-balance correction coefficient in the non-color-mixture state, the white balance of the object image can be corrected without having the light receiving amount of the color-mixture components included in the light-receiving-amount output of each unit pixel group forming the object image.

Further, since the light-emitting units and the imaging unit described above are contained in the capsule endoscope, it is not required to contain a special filter in the capsule endoscope, which allows color light of a narrow wavelength band to pass through. Therefore, downsizing of the capsule endoscope can be promoted, and a burden on the subject in which the capsule endoscope is inserted in an organ can be reduced.

Still further, when a chart image is captured, color lights of plural colors are simultaneously emitted. Therefore, without changing a light-emitting pattern of the color lights of the plural colors, chart image information about the respective color components of RGB or the like can be acquired to know the color-mixture state of each color component. As a result, without providing each light-emitting unit with a special circuit for changing the light-emitting pattern of the color lights of the plural colors, downsizing of the capsule endoscope having the light-emitting units described above incorporated therein can further be promoted.

Second Embodiment

Next, a second embodiment of the present invention is described. In the first embodiment described above, the in-vivo image and the chart image of each color component are simultaneously captured, the inverse matrix $M^{-1}$ of the color-mixture matrix M is calculated for each in-vivo image, and the color-mixture state of each in-vivo image is corrected by using the inverse matrix $M^{-1}$ for each of the in-vivo image. By contrast, in the second embodiment, before the in-vivo image is captured, chart images that selectively reflects the respective color components are captured to calculate in advance the inverse matrix $M^{-1}$ of the color-mixture matrix M, and then the common inverse matrix $M^{-1}$ is used for each of the in-vivo images sequentially captured to correct the color-mixture state.

Figure 9:
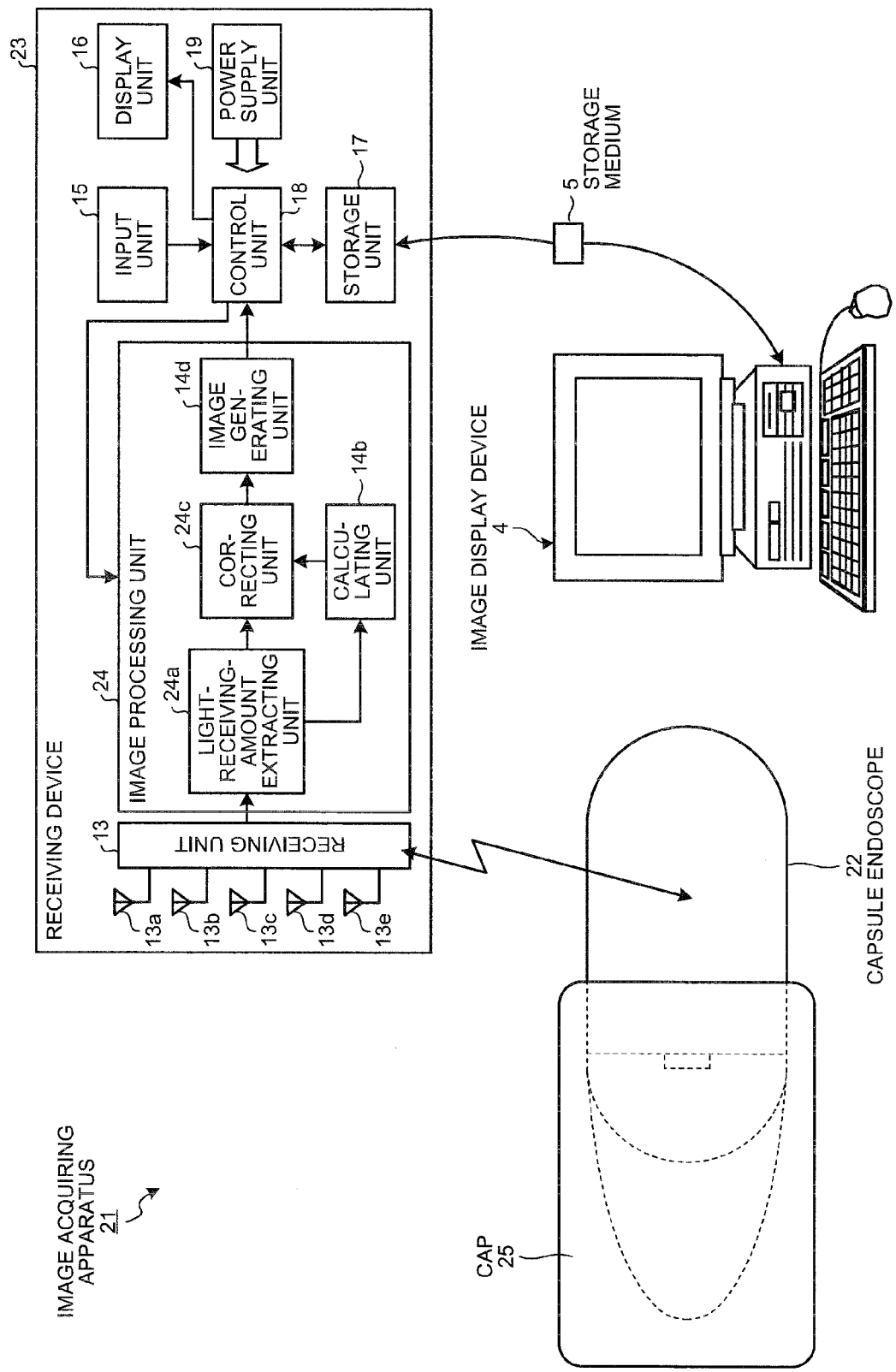
FIG. 9 is a block diagram schematically depicting a configuration example of an observation apparatus according to a second embodiment of the present invention.
Figure 10:
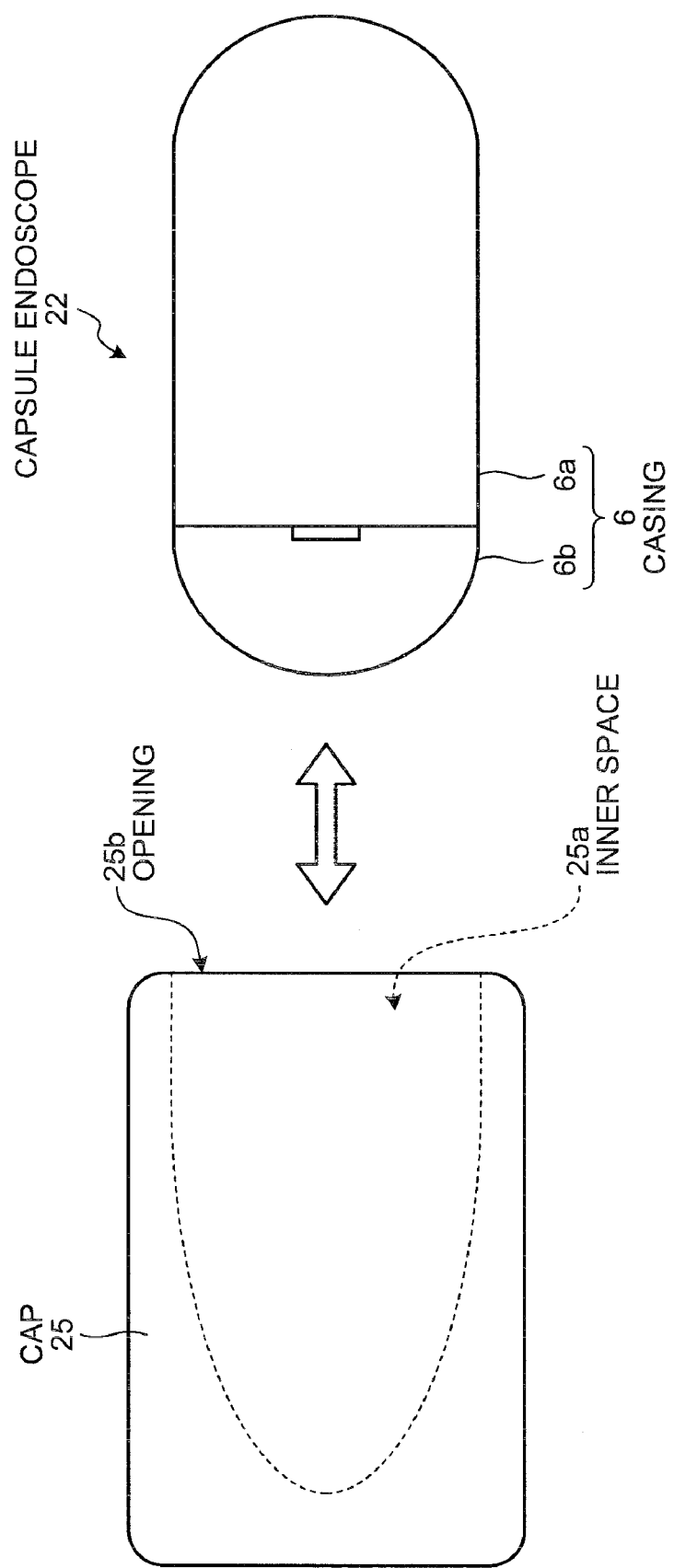
FIG. 10 is a schematic diagram exemplifying a connection and disconnection state of a cap that has a color chart of plural colors formed therein and a capsule endoscope.
Figure 11:
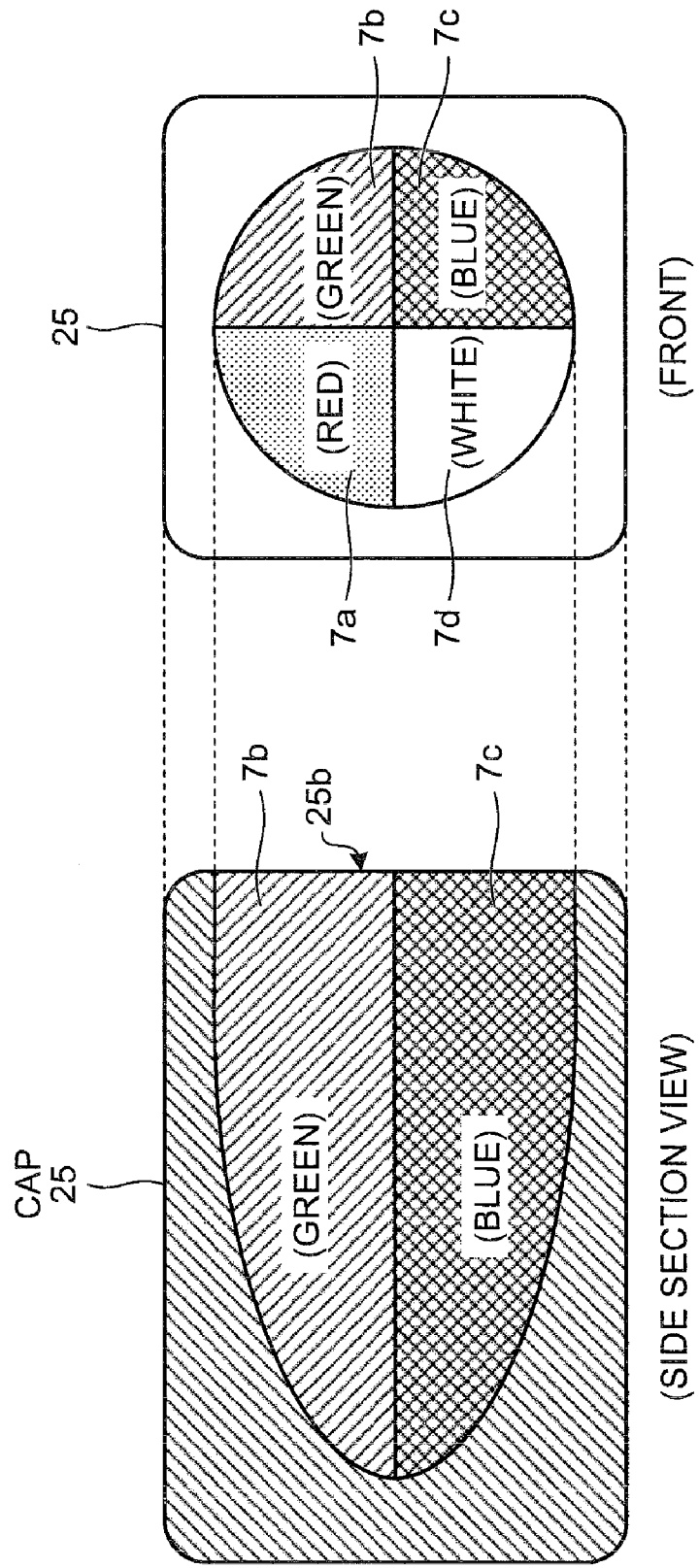
FIG. 11 is a schematic diagram depicting a configuration example of the cap that has color charts of plural colors formed therein.

FIG. 9 is a block diagram schematically depicting a configuration example of an observation apparatus according to the second embodiment of the present invention. FIG. 10 is a schematic diagram exemplifying a connection and disconnection state of a cap that has color charts of plural colors formed therein and a capsule endoscope. FIG. 11 is a schematic diagram depicting a configuration example of the cap that has color charts of plural colors formed therein.

As depicted in FIGS. 9 to 11, an image acquiring apparatus 21, which is an observation apparatus according to the second embodiment, has a capsule endoscope 22 in place of the capsule endoscope 2 of the image acquiring apparatus 1 according to the first embodiment described above, the receiving device 23 in place of the receiving device 3, and further has a cap 25 with the color chart 7 of plural colors formed therein. Also, the receiving device 23 has an image processing unit 24 in place of the image processing unit 14 of the receiving device 3 of the first embodiment described above. Other configurations are the same as those of the first embodiment, and the same component units are denoted with the same reference numerals.

The capsule endoscope 22 has a similar configuration as that of the capsule endoscope 2 according to the first embodiment described above, except that the color chart 7 is not formed on the inner wall of the optical dome 6b. The capsule endoscope 22 captures a chart image of the color chart 7 formed inside of the cap 25 in a state where the cap 25 is mounted so as to cover the optical dome 6b of the capsule casing 6, and wirelessly transmits chart image information corresponding to the chart image to the external receiving device 23. Also, the capsule endoscope 22 after having the cap 25 removed therefrom and being inserted into an organ of the subject captures an in-vivo image of the subject at predetermined intervals, and sequentially and wirelessly transmits the captured in-vivo images to the external receiving device 23. Other than the function of wirelessly transmitting the in-vivo image and the chart image separately, the capsule endoscope 22 has functions similar to those of the capsule endoscope 2 of the first embodiment described above.

The receiving device 23 has functions similar to those of the receiving device 3 of the first embodiment described above, other than the functions of the image processing unit 24. The image processing unit 24 acquires the light-receiving-amount outputs $S_R$, $S_G$, $S_B$, and $S_W$ corresponding to the chart images PR, PG, PB, and PW, respectively, of the color components captured separately from the in-vivo images, and calculates various correction coefficients, such as the inverse matrix $M^{-1}$ of the color-mixture matrix M, the white-balance correction coefficient, and the gamma value, before acquiring the in-vivo image. Then, the image processing unit 24 uses common various correction coefficients (such as the inverse matrix $M^{-1}$, the white-balance correction coefficient, and the gamma value) for each of the in-vivo images sequentially captured to perform a color-mixture correcting process, a white-balance correcting process, and a gamma correcting process on each in-vivo image. Other than the correcting process function, the image processing unit 24 has functions similar to those of the image processing unit 14 of the first embodiment described above.

The image processing unit 24 has a light-receiving-amount extracting unit 24a in place of the light-receiving-amount extracting unit 14a of the image processing unit 14 of the first embodiment described above, a correcting unit 24c in place of the correcting unit 14c, and the calculating unit 14b and the image generating unit 14d described above.

The light-receiving-amount extracting unit 24a extracts the chart image information about each color component captured separately from the in-vivo image from the image signal sequentially received from the receiving unit 13, and transmits the extracted chart image information to the calculating unit 14b. Specifically, the receiving unit 13 demodulates a radio signal from the capsule endoscope 22 to an image signal, and transmits the image signal obtained through demodulation to the light-receiving-amount extracting unit 24a. The light-receiving-amount extracting unit 24a extracts image information contained in the image signal received from the receiving unit 13 and, based on the light-receiving-amount value of each color component contained in the extracted image information, determines whether the image information is either of chart image information and in-vivo image information. When the image signal contains chart image information, the light-receiving-amount extracting unit 24a transmits an image signal containing the chart image information to the calculating unit 14b. When the image signal contains in-vivo image information, the light-receiving-amount extracting unit 24a transmits an image signal containing the in-vivo image information to the correcting unit 24c.

The correcting unit 24c acquires various correction coefficients calculated by the calculating unit 14b, holds these acquired various correction coefficients, and uses these held various correction coefficients to perform various correcting processes (such as a color-mixture correcting process, a white-balance correcting process, and a gamma correcting process) on the plural pieces of in-vivo image information sequentially received from the light-receiving-amount extracting unit 24a. That is, the correcting unit 24c commonly uses these held various correction coefficients for plural in-vivo images to sequentially perform various correcting processes on these plural in-vivo images. Whenever acquiring new one of various correction coefficients from the calculating unit 14b later, the correcting unit 24c updates the held one of the various correction coefficients.

Here, these various correction coefficients for common use by the correcting unit 24c on the plural in-vivo images are the correction matrix in the color-mixture correcting process (the inverse matrix $M^{-1}$ of the color-mixture matrix M), the white-balance correction coefficient (the light-receiving-amount output W in the non-color-mixture state), the gamma value, or the like. In the second embodiment, the calculating unit 14b calculates these various correction coefficients based on the chart image information corresponding to the chart image of each color component captured separately from the in-vivo image and, whenever calculating these values, transmits these calculated various correction coefficients to the correcting unit 24c.

As depicted in FIGS. 10 and 11, the cap 25 has an inner space 25a that communicates with the outside via an opening 25b formed at one end. The opening 25b has a shape similar to a cross-section shape of the casing 6 (specifically, the case main body 6a) of the capsule endoscope 22, and is formed in a dimension capable of removably inserting the casing 6 therein. The inner space 25a is formed so as to have a size and shape capable of containing the optical dome 6b of the casing 6 inserted via the opening 25b. On an inner wall surface of the cap 25 that has the inner space 25a, color charts of plural colors are formed, which includes a red chart 7a, a green chart 7b, a blue chart 7c, and a white chart 7d. The cap 25 configured as described above removably covers a casing portion including at least the optical dome 6b of the capsule endoscope 22 inserted in the inner space 25a via the opening 25b and also has the red chart 7a, the green chart 7b, the blue chart 7c, and the white chart 7d disposed in a field of view to be captured of the capsule endoscope 22 in this state (specifically, in an area in an angle of view of the imaging unit 9). The cap 25 having the capsule endoscope 22 inserted in this manner prevents external light from leaking into the field of view to be captured of the inserted capsule endoscope 22.

Here, the red chart 7a, the green chart 7b, the blue chart 7c, and the white chart 7d are formed on the inner wall surface of the cap 25 so as to each occupy an approximately equal area in the field of view to be captured of the capsule endoscope 22 inserted in the inner space 25a of the cap 25, with an optical axis of the imaging unit 9 being taken as a center. With the red chart 7a, the green chart 7b, the blue chart 7c, and the white chart 7d being formed in this manner, the imaging unit 9 can approximately equalize the numbers of pixels forming the chart images PR, PG, PB, and PW, and can capture a chart image in which the chart images PR, PG, PB, and PW each having the same number of pixels are included in one frame.

Figure 12:
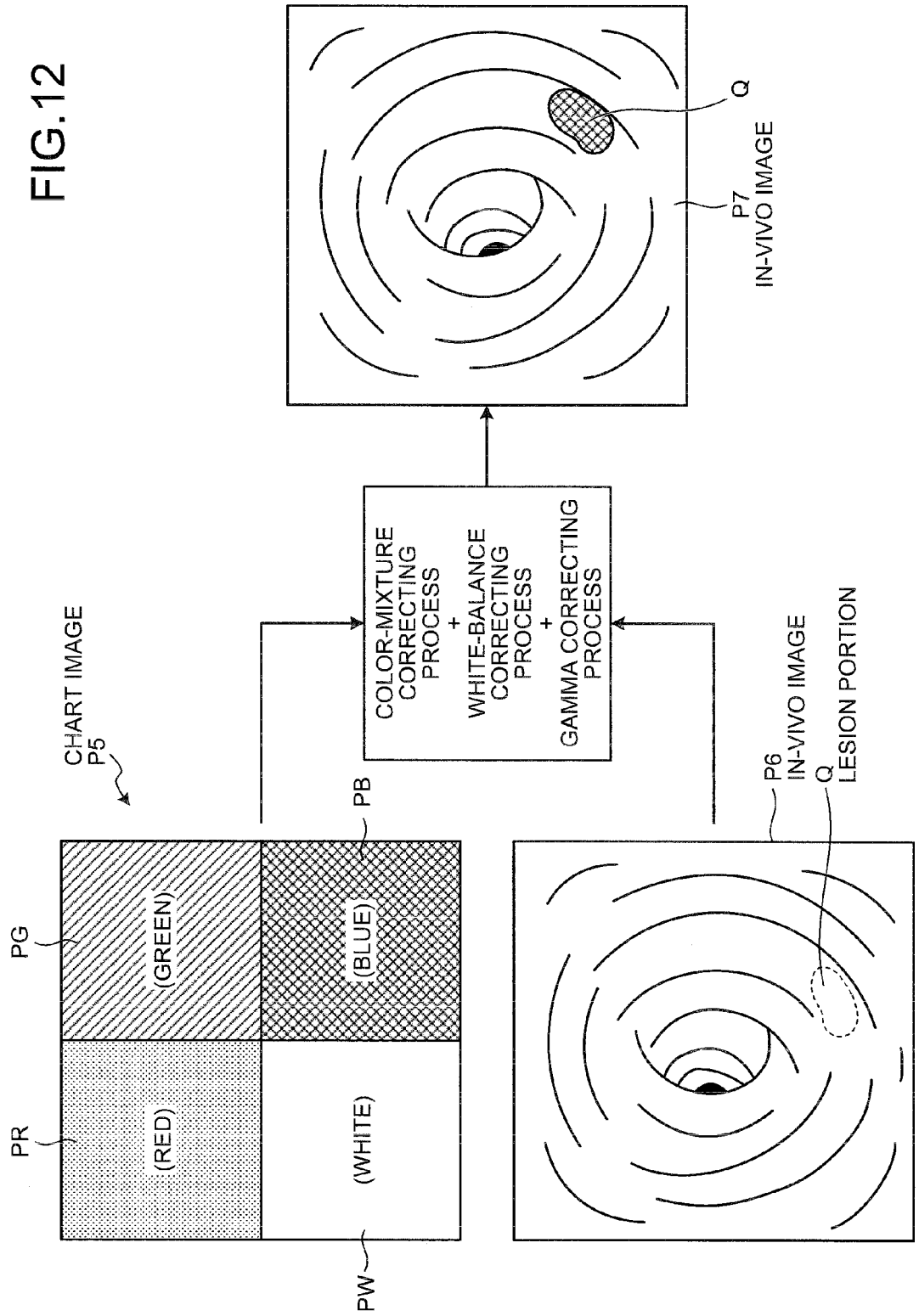
FIG. 12 is a schematic diagram explaining an operation of an image processing unit that corrects an in-vivo image captured separately from a chart image and generates and outputs a corrected in-vivo image.

Next, the operation of the image processing unit 24 is specifically described, which includes the operation of performing various correcting process on an in-vivo image based on various correction coefficients for common use on plural in-vivo images and generating and outputting the corrected in-vivo image. FIG. 12 is a schematic diagram explaining the operation of the image processing unit 24 that performs various correcting processes on an in-vivo image captured separately from the chart image and generates and outputs the corrected in-vivo image.

In the image acquiring apparatus 21 according to the second embodiment, before being inserted into an organ of the subject 100, the capsule endoscope 22 captures a chart image P5 of plural colors with the cap 25 fitting thereon as described above (refer to FIGS. 9 and 10). The chart image of the plural colors P5 is formed of the chart images PR, PG, PB, and PW of the plural colors, as depicted in FIG. 12. In this case, the chart images PR, PG, PB, and PW are each formed of a divided pixel group having approximately the same number of pixels obtained through division into four by two orthogonal axes passing through the image center of the chart image P5 corresponding to the optical axis of the imaging unit 9.

Whenever acquiring from the receiving unit 13 chart image information about the chart image P5 in which these chart images PR, PG, PB, and PW are contained in one frame, the image processing unit 24 performs a process procedure approximately similar to steps S102 to S106 described above to calculate the inverse matrix $M^{-1}$ of the color-mixture matrix M (the correction matrix for a color-mixture correcting process) and the light-receiving-amount output W in the non-color-mixture state (the white-balance correction coefficient) and further calculate the gamma value. The image processing unit 24 holds these correction matrix, the white-balance correction coefficient, and the gamma value as various correction coefficients for common use on plural in-vivo images.

In this case, the calculating unit 14b can acquire the light-receiving-amount outputs $S_R$, $S_G$, $S_B$, and $S_W$ of the pixel group arranged near the image center of the chart image P5. Therefore, the calculating unit 14b can calculate a correction matrix, white-balance correction coefficient, and gamma value that are more accurate (that is, allow color reproducibility to be more increased) compared with the case of the first embodiment described above.

As described above, the capsule endoscope 22 having the cap 25 fitting thereon captures the chart image P5, and is then swallowed from the mouth of the subject 100 with the cap 25 removed therefrom. In this case, the capsule endoscope 22 captures an in-vivo image P6 at predetermined intervals while moving by peristalsis or the like through the inside of the organ of the subject 100. The capsule endoscope 22 inside of the organ wirelessly transmits in-vivo image information about the captured in-vivo image P6 to the receiving device 23.

Whenever acquiring the in-vivo image information about the in-vivo image P6 through the receiving unit 13, the image processing unit 24 performs a process procedure approximately the same as steps S202 to S204 described above to perform a color-mixture correcting process and a white-balance correcting process on the in-vivo image P6 and further perform a gamma correcting process on the in-vivo image P6.

In this case, on the plural in-vivo images P6 sequentially captured, the correcting unit 24c commonly uses the correction matrix (the inverse matrix $M^{-1}$ of the color-mixture matrix M), white-balance correction coefficient (the light-receiving-amount output W in the non-color-mixture state), and gamma value held as described above to sequentially perform a color-mixture correcting process, a white-balance correcting process, and a gamma correcting process on these plural in-vivo images P6.

The image processing unit 24 acquires in-vivo image information about a corrected in-vivo image P7 with the color-mixture state, the white balance, or the like of the in-vivo image P6 being corrected. Note that the in-vivo image information about the in-vivo image P7 contains the light-receiving-amount output Cout of each unit pixel forming the corrected in-vivo image P7. Based on thus acquired light-receiving-amount output Cout of each unit pixel group, the image processing unit 24 generates the corrected in-vivo image P7. In this case, the image generating unit 14d does not have to perform the above-described mask processing on the chart image.

As with the case of the first embodiment described above, the corrected in-vivo image P7 generated and output by the image processing unit 24 is acquired by the image display device 4 via the storage medium 5. The in-vivo image P7 displayed by the image display device 4 more clearly depicts, as exemplarily depicted in FIG. 12, the state (such as color, size, and shape) of the lesion portion Q, which is unclear in the in-vivo image P6 before correction, compared with the case of the first embodiment.

As exemplified in the in-vivo image P7, the image acquiring apparatus 21 that has the image processing unit 24 can acquire an in-vivo image with high color reproducibility capable of more clearly depicting the state of a desired examination target, such as blood or lesion portion, compared with the case of the first embodiment. A user, such as a doctor or nurse, can more reliably detect the desired examination target, such as blood or a lesion portion, based on the corrected in-vivo image acquired by the image acquiring apparatus 21, and can more accurately find a reflectance of each RGB color light (that is, each of the color lights of plural wavelength bands) for the desired examination target. As a result, the user can perform a detailed analysis of the desired examination target with higher accuracy.

As described in the foregoing, in the second embodiment, a chart image in which a color chart of plural colors corresponding to element lights of plural colors forming a white light is captured in a frame separately from a desired object image, such as the inside of the organ of the subject, is captured. Based on the light-receiving-amount output of the chart image of plural colors contained in the chart image of one frame, various correction coefficients, such as a correction matrix (an inverse matrix of a color-mixture matrix), are calculated. By commonly using these calculated various correction coefficients for plural object images, various correcting processes, such as a color-mixture correcting process and a white-balance correcting process, are performed on the object image. Others are configured similarly to those in the first embodiment described above. Therefore, when various correcting processes, such as the color-mixture correcting process and the white-balance correcting process, are sequentially performed on the plural object images, the number of processes of calculating various correction coefficients for use in various correcting processes can be reduced (for example, the number of calculating processes can be one for an correction coefficient). With this, the processing speed until various correcting processes on plural object images are completed can be increased. As a result, operations and effects similar to those of the first embodiment described above can be obtained, and also the time required until various correcting processes on the plural object images are completed can be reduced.

Also, the light-emitting-amount output of the pixel group arranged near the image center of the chart image, in which the color chart of the plural colors are provided in one frame, is acquired. Therefore, various correction coefficients, such as the correction matrix and the white-balance correction coefficient, can be accurately calculated. As a result, color reproducibility of the object image can further be increased.

Furthermore, it is not necessary to perform chart-image mask processing required when the original image containing the object image and the chart image in one frame is captured. Therefore, the time until the corrected object image is acquired can be reduced. Also, compared with the case of the first embodiment, it is possible to capture an object image in a wider field of view to be captured.

Modification Example of the Second Embodiment

Next, a modification example of the second embodiment of the present invention is described. In the second embodiment described above, a color chart of plural colors (for example, the red chart 7a, the green chart 7b, the blue chart 7c, and the white chart 7d) is formed on the inner wall surface of one cap 25. In the modification example of the second embodiment, a cap is prepared for each color of the color chart of the plural colors, and the color chart of any of the plural colors is formed for each cap, and the color charts for the caps are sequentially captured.

Figure 13:
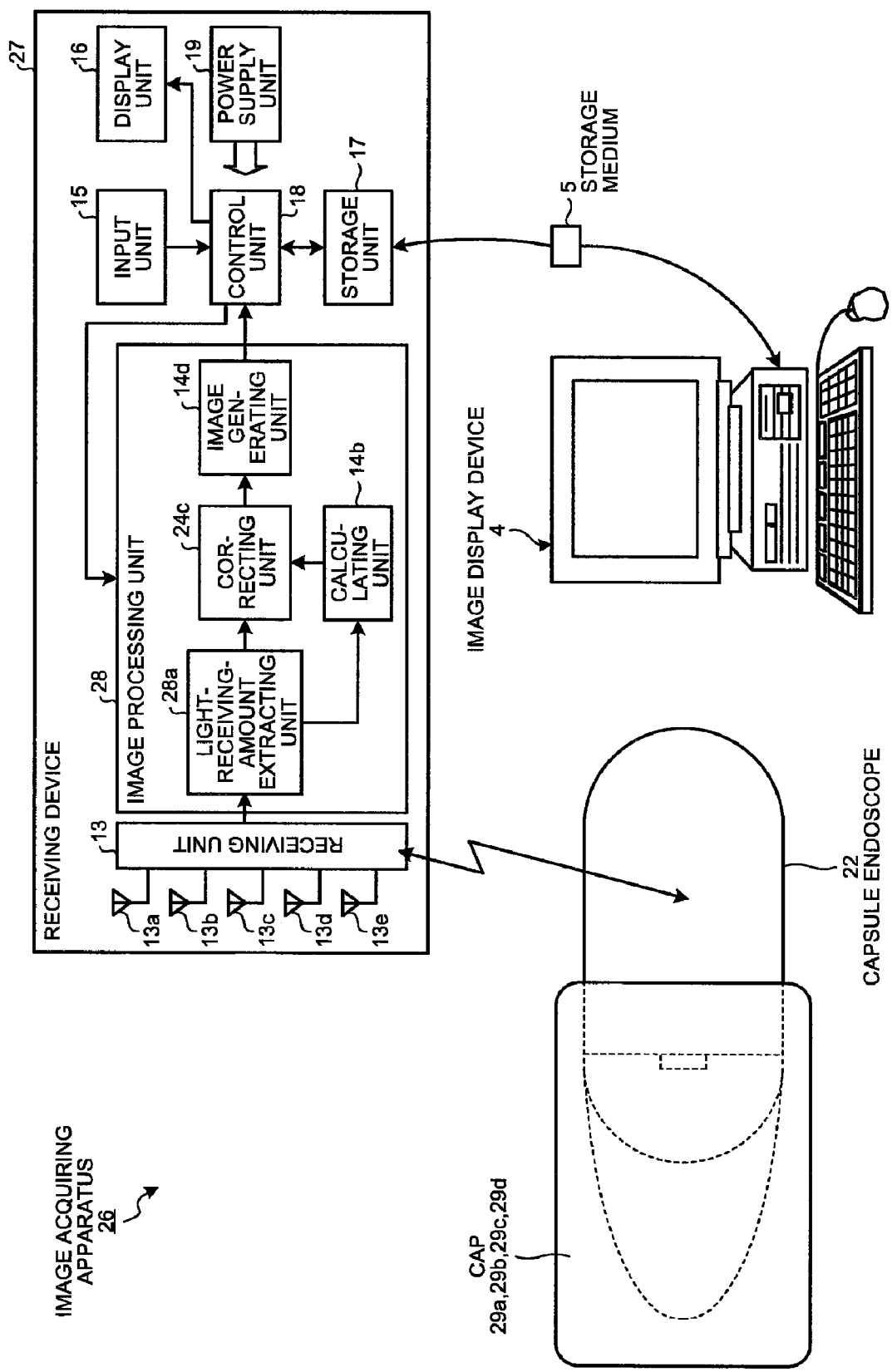
FIG. 13 is a block diagram schematically depicting a configuration example of an observation apparatus according to a modification example of the second embodiment of the present invention.
Figure 14:
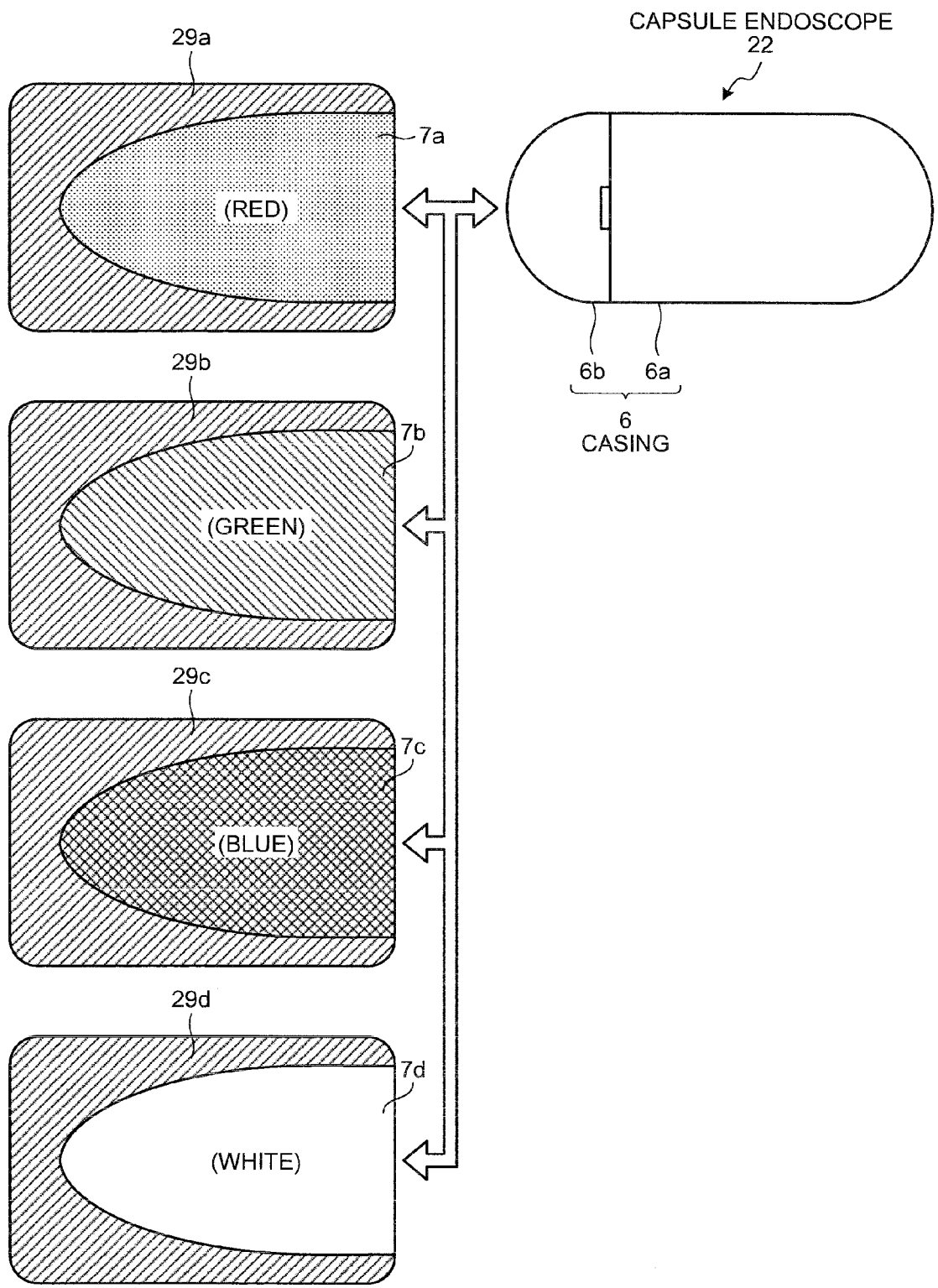
FIG. 14 is a schematic side section view depicting a configuration example of plural caps each of which has a color chart of any of plural colors.

FIG. 13 is a block diagram schematically depicting a configuration example of an observation apparatus according to the modification example of the second embodiment of the present invention. FIG. 14 is schematic side section view depicting a configuration example of plural caps each of which has a color chart of any of plural colors.

As depicted in FIGS. 13 and 14, an image acquiring apparatus 26, which is an observation apparatus according to the modification example of the second embodiment, has plural caps 29a to 29d in place of the cap 25 of the image acquiring apparatus 21 according to the second embodiment described above and a receiving device 27 in place of the receiving device 23. Also, the receiving device 27 has an image processing unit 28 in place of the image processing unit 24 of the receiving device 23 of the second embodiment described above. Other configurations are the same as those of the second embodiment, and the same component units are denoted with the same reference numerals.

Other than the functions of the image processing unit 28, the receiving device 27 has functions similar to those of the receiving device 23 of the second embodiment described above. The image processing unit 28 acquires light-receiving-amount outputs $S_R$, $S_G$, $S_B$, and $S_W$ corresponding to the chart images PR, PG, PB, and PW, respectively, captured separately from the in-vivo image, and calculates various correction coefficients, such as the inverse matrix $M^{-1}$ of the color-mixture matrix M, the white-balance correction coefficient, and the gamma value before acquiring an in-vivo image. In this case, the image processing unit 28 acquires the light-receiving-amount outputs $S_R$, $S_G$, $S_B$, and $S_W$ corresponding to all pixels of the imaging unit 9. Other functions of the image processing unit 28 are similar to those of the image processing unit 24 of the second embodiment described above.

The image processing unit 28 has a light-receiving-amount extracting unit 28a in place of the light-receiving-amount extracting unit 24a of the image processing unit 24 of the second embodiment described above, and the calculating unit 14b, the correcting unit 24c; and the image generating unit 14d described above.

The light-receiving-amount extracting unit 28a extracts chart image information about each color component captured separately from the in-vivo image for each image (each frame) from image signals sequentially received from the receiving unit 13, and transmits the extracted chart image information for each frame to the calculating unit 14b. Specifically, the receiving unit 13 demodulates a radio signal from the capsule endoscope 22 to an image signal, and transmits the image signal obtained through demodulation to the light-receiving-amount extracting unit 28a. The light-receiving-amount extracting unit 28a extracts image information contained in the image signal received from the receiving unit 13 and, based on the light-receiving-amount value of each color component contained in the extracted image information, determines whether the image information is either of chart image information and in-vivo image information for each of the frame. When the image signal contains chart image information for each frame, the light-receiving-amount extracting unit 28a transmits an image signal containing the chart image information for each frame to the calculating unit 14b. When the image signal contains in-vivo image information, the light-receiving-amount extracting unit 28a transmits an image signal containing the in-vivo image information to the correcting unit 24c.

Here, in the modification example of the second embodiment, the calculating unit 14b sequentially acquires chart image information for each frame from the light-receiving-amount extracting unit 28a and, whenever calculating various correction coefficients based on each piece of chart image information for each frame, transmits the calculated various correction coefficients to the correcting unit 24c. Note that the chart image information for each frame is image information corresponding to any of the chart images PR, PG, PB, and PW for each frame formed of all pixels of the imaging unit 9, and contains any of the light-receiving-amount outputs $S_R$, $S_G$, $S_B$, and $S_W$ corresponding to all pixels of the imaging unit 9.

In detail, the light-receiving-amount output $S_R$ corresponding to all pixels represents a third-order column vector containing, as vector components, an average light-receiving-amount value of red light received by all R-component pixels, an average light-receiving-amount value of red light received by all G-component pixels, and an average light-receiving-amount value of red light received by all B-component pixels when the chart image PR for each frame is captured. Also, the light-receiving-amount output $S_G$ corresponding to all pixels represents a third-order column vector containing, as vector components, an average light-receiving-amount value of green light received by all R-component pixels, an average light-receiving-amount value of green light received by all G-component pixels, and an average light-receiving-amount value of green light received by all B-component pixels when the chart image PG for each frame is captured. Furthermore, the light-receiving-amount output $S_B$ corresponding to all pixels represents a third-order column vector containing, as vector components, an average light-receiving-amount value of blue light received by all R-component pixels, an average light-receiving-amount value of blue light received by all G-component pixels, and an average light-receiving-amount value of blue light received by all B-component pixels when the chart image PB for each frame is captured. Still further, the light-receiving-amount output $S_W$ corresponding to all pixels represents a third-order column vector containing, as vector components, an average light-receiving-amount value of all R-component pixels, an average light-receiving-amount value of all G-component pixels, and an average light-receiving-amount value of all B-component pixels when the chart image PW for each frame is captured.

The plural caps 29a to 29d are each formed in a structure similar to that of the cap 25 of the second embodiment described above. Each cap has a color chart of any of plural colors (specifically, the red chart 7a, the green chart 7b, the blue chart 7c, and the white chart 7d). Specifically, as depicted in FIG. 14, the cap 29a has the red chart 7a on the inner wall surface formed similarly to the cap 25 described above. The cap 29b has the green chart 7b on the inner wall surface formed similarly to the cap 25 described above. The cap 29c has the blue chart 7c on the inner wall surface formed similarly to the cap 25 described above. The cap 29d has the white chart 7d on the inner wall surface formed similarly to the cap 25 described above.

Also, the plural caps 29a to 29d, when having the capsule endoscope 22 inserted in its inner space, removably covers the casing portion of the capsule endoscope including at least the optical dome 6b and also prevents external light from leaking into the field of view to be captured of the capsule endoscope 22. In this case, the cap 29a has the red chart 7a disposed in a field of view to be captured (specifically, an area in an angle of view of the imaging unit 9) of the capsule endoscope 22 in an inserted state. The cap 29b has the green chart 7b disposed in the field of view to be captured of the capsule endoscope 22 in the inserted state. The cap 29c has the blue chart 7c disposed in the field of view to be captured of the capsule endoscope 22 in the inserted state. The cap 29d has the white chart 7d disposed in the field of view to be captured of the capsule endoscope 22 in the inserted state.

With these plural caps 29a to 29d having the capsule endoscope 22 sequentially inserted therein in a predetermined order, the color chart disposed in the field of view to be captured of the capsule endoscope 22 in an inserted state can be sequentially switched to the red chart 7a, the green chart 7b, the blue chart 7c, and the white chart 7d. With this, the capsule endoscope 22 can sequentially capture the chart image PR in which the red chart 7a occupies the entire frame, the chart image PG in which the green chart 7b occupies the entire frame, the chart image PB in which the blue chart 7c occupies the entire frame, and the chart image PW in which the white chart 7d occupies the entire frame. Note that the capsule endoscope 22 sequentially and wirelessly transmits to the external receiving device 27 each piece of chart image information for each frame corresponding to the chart images PR, PG, PB, and PW sequentially captured in a manner as described above.

Figure 15:
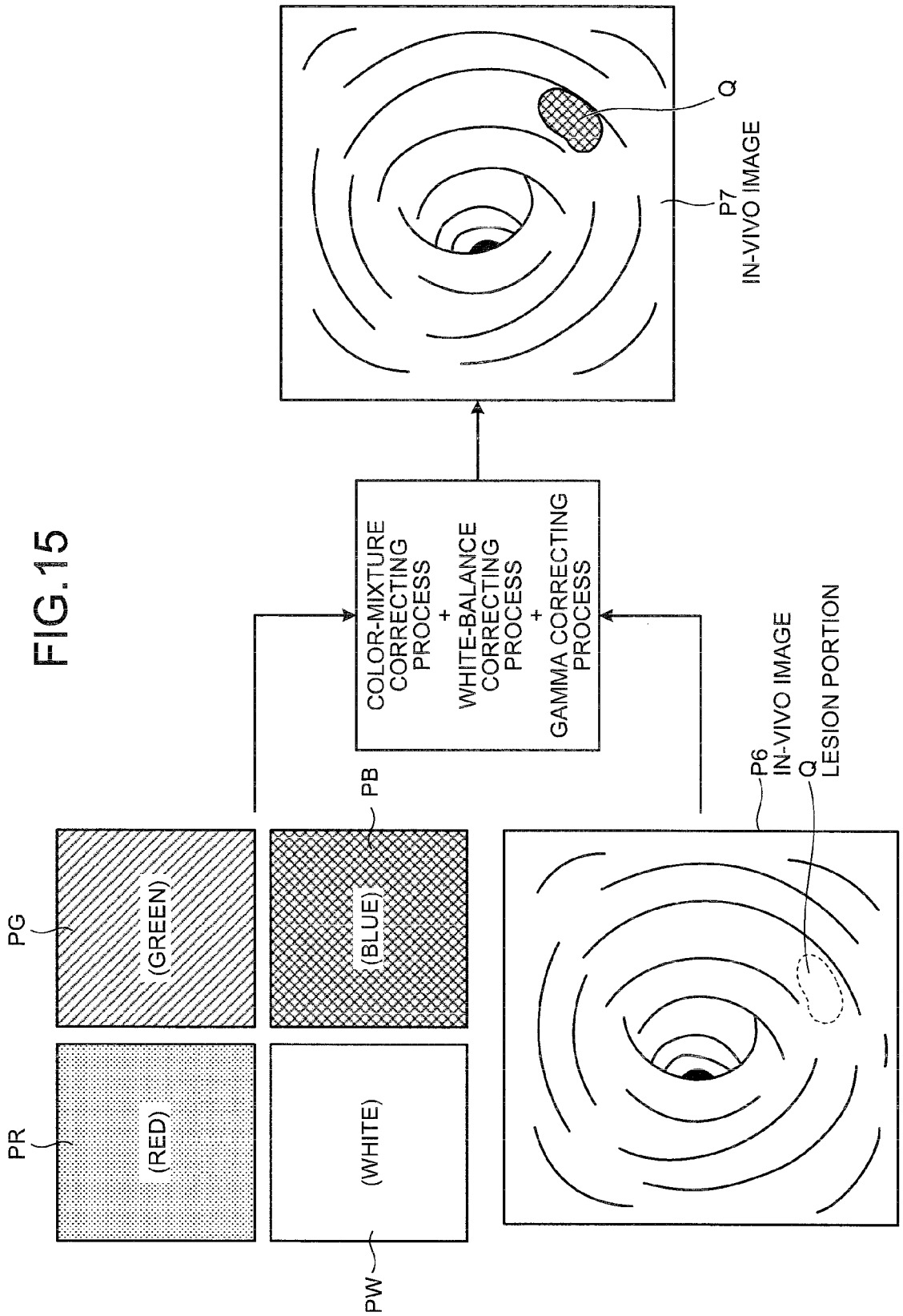
FIG. 15 is a schematic diagram explaining an operation of an image processing unit that uses various correction coefficients calculated based on each piece of chart image information for each frame to correct the in-vivo image.

Next, the operation of the image processing unit 28 is described, which includes the process of calculating various correction coefficients based on each piece of chart image information for each frame to perform various correcting processes on the in-vivo image, and generating and outputting the corrected in-vivo image. FIG. 15 is a schematic diagram explaining the operation of the image processing unit 28 that uses various correction coefficients calculated based on each piece of chart image information for each frame to correct the in-vivo image.

Before acquiring an in-vivo image P6, the image processing unit 28 sequentially acquires each piece of chart image information for each frame corresponding to the chart images PR, PG, PB, and PW as depicted in FIG. 15. In this case, based on each piece of chart image information for each frame, the image processing unit 28 acquires the light-receiving-amount outputs $S_R$, $S_G$, $S_B$, and $S_W$ corresponding to all pixels of the imaging unit 9. Whenever acquiring these light-receiving-amount outputs $S_R$, $S_G$, $S_B$, and $S_W$ corresponding to all pixels, the image processing unit 28 performs a process procedure approximately similar to steps S102 to S106 described above to calculate the inverse matrix $M^{-1}$ of the color-mixture matrix M (the correction matrix for a color-mixture correcting process) and the light-receiving-amount output W in the non-color-mixture state (the white-balance correction coefficient) and further calculate the gamma value. The image processing unit 28 holds these correction matrix, the white-balance correction coefficient, and the gamma value as various correction coefficients for common use on plural in-vivo images.

In this case, various correction coefficients are calculated based on the light-receiving-amount outputs $S_R$, $S_G$, $S_B$, and $S_W$ corresponding to all pixels. Therefore, the calculating unit 14b can calculate the various correction coefficients corresponding to the pixel groups forming the in-vivo image. As a result, the calculating unit 14b can calculate the correction matrix, the white-balance correction coefficient, and the gamma value more correctly (that is, in a manner such that color reproducibility can further be increased), compared with the case of the second embodiment described above.

Then, the image processing unit 28 performs a process procedure similar to that of the image processing unit 24 of the second embodiment described above to perform a color-mixture correcting process and a white-balance correcting process on the in-vivo image P6, and further perform a gamma correcting process On the in-vivo image P6. The image processing unit 28 can correct the color-mixture state, the white balance, or the like of the in-vivo image P6 more accurately compared with the image processing unit 24 of the second embodiment described above to generate and output a corrected in-vivo image P7.

The corrected in-vivo image P7 generated and output from the image processing unit 28 depicts the state (such as color, size, and shape) of the lesion portion Q, which is unclear in the in-vivo image P6 before correction, more clearly compared with the case of the second embodiment. The image acquiring apparatus 26 that has the image processing unit 28 can acquire an in-vivo image with high color reproducibility capable of clearly depicting the state of a desired examination target, such as blood or a lesion portion, compared with the case of the second embodiment described above.

As described in the foregoing, in the modification example of the second embodiment of the present invention, color charts of plural colors are sequentially captured for each frame to sequentially acquire each piece of chart image information for each frame. Based on each piece of chart image information for each frame, light-receiving-amount outputs of the plural colors corresponding to all pixels of the imaging unit are acquired. Based on the light-receiving-amount outputs of the plural colors corresponding to all pixels, various correction coefficients, such as a correction matrix (an inverse matrix of a color-mixture matrix), are calculated. Others are configured similarly to those in the second embodiment described above. Therefore, various correction coefficients, such as the correction matrix and white-balance correction coefficient corresponding to the pixel group forming a desired object image, such as the inside of an organ of a subject, can be calculated. Thus, operations and effects similar to those of the second embodiment described above can be obtained, and also color reproducibility of the object image can further be increased.

Also, in the modification example of the second embodiment of the present invention, since the light-receiving-amount outputs of plural colors corresponding to all pixels of the imaging unit are acquired, various correction coefficients, such as the correction matrix and the white-balance correction coefficient, can be sequentially calculated for each unit pixel group forming one dot of the object image. By using various correction coefficients for each unit pixel group on each unit pixel group of the object image, the color-mixture state, the white balance, or the like of the object image can be more accurately corrected.

Third Embodiment

Next, a third embodiment of the present invention is described. In the modification example of the second embodiment, the plural caps 29a to 29d each having a color chart of any of plural colors are prepared and the cap in which the capsule endoscope 22 is to be inserted is sequentially switched to sequentially capture the chart images PR, PG, PB, and PW for each frame, thereby acquiring each piece of chart image information for each frame. In the third embodiment, the luminescent color of the capsule endoscope in a state where one cap that has the white chart 7d is fitted thereon is sequentially switched to sequentially capture the chart images PR, PG, PB, and PW for each frame, thereby acquiring each piece of chart image information for each frame.

Figure 16:
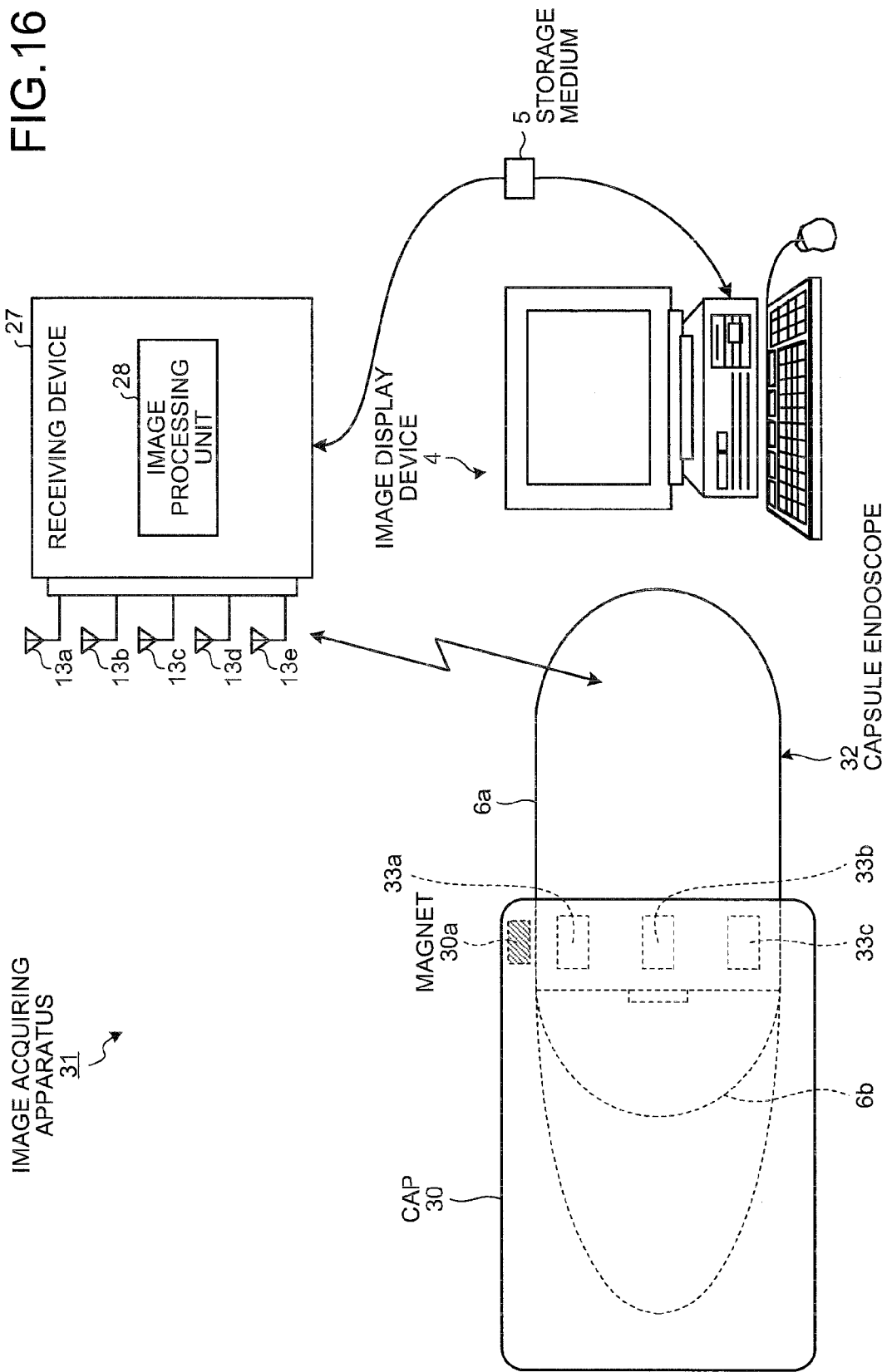
FIG. 16 is a schematic diagram depicting a configuration example of an observation apparatus according to a third embodiment of the present invention.
Figure 17:
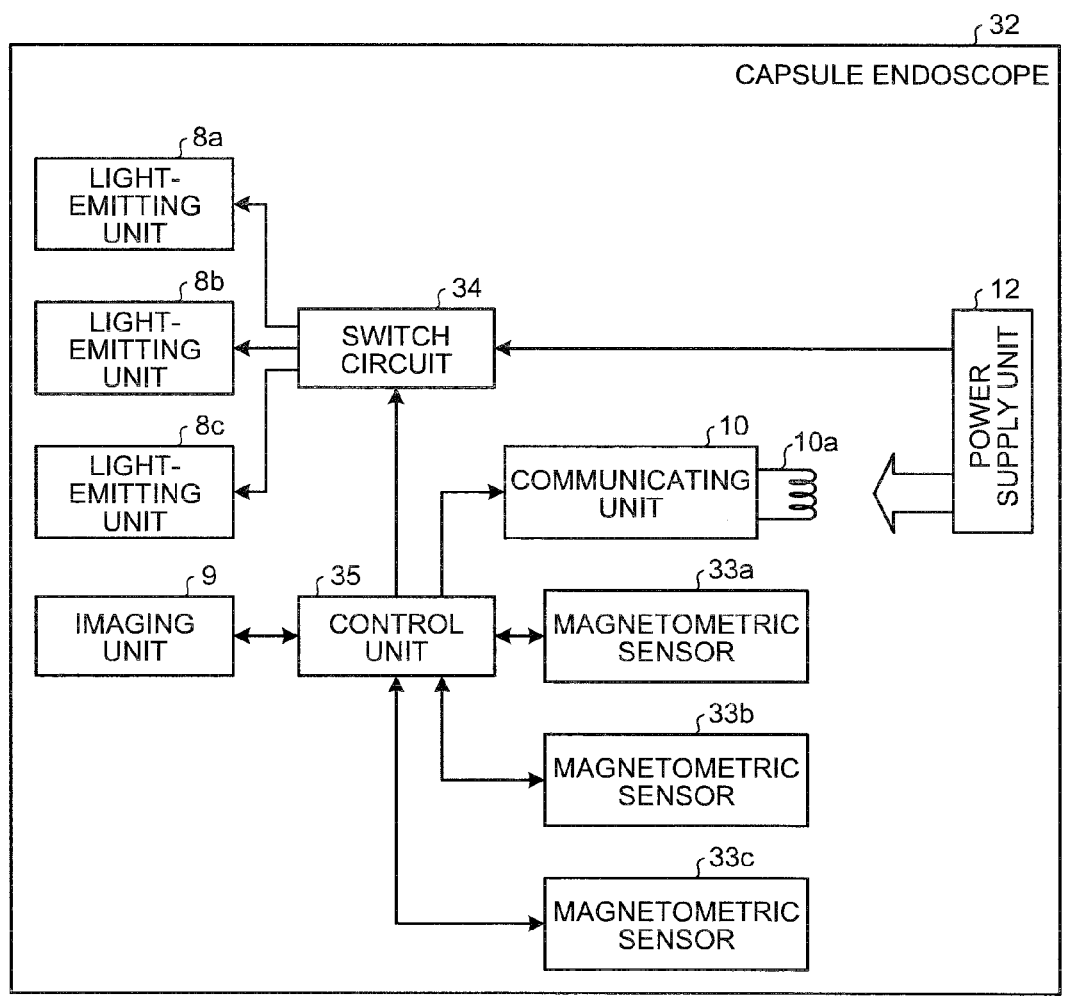
FIG. 17 is a block diagram schematically exemplifying the functional configuration of a capsule endoscope of the observation apparatus according to the third embodiment.

FIG. 16 is a schematic diagram depicting a configuration example of an observation apparatus according to the third embodiment of the present invention. FIG. 17 is a block diagram schematically exemplifying the functional configuration of a capsule endoscope of the observation apparatus according to the third embodiment. As depicted in FIGS. 16 and 17, an image acquiring apparatus 31, which is an observation apparatus according to the third embodiment, has a capsule endoscope 32 in place of the capsule endoscope 22 of the image acquiring apparatus 26 according to the modification example of the second embodiment described above, and one cap 30 in place of the plural caps 29a to 29d. Other configurations are the same as those of the modification example of the second embodiment, and the same component units are denoted with the same reference numerals.

The cap 30 is formed so as to have a structure similar to that of the cap 29d (a cap that has the white chart 7d on the inner wall surface) in the modification example of the second embodiment described above, and has the white chart 7d on its inner wall surface. As with the cap 29d described above, when the capsule endoscope 32 is inserted in the inner space, the cap 30 removably covers the casing portion including at least the optical dome 6b of the capsule endoscope 32, and also prevents external light from leaking into the field of view to be captured of the capsule endoscope 32. In this case, the cap 30 has the white chart 7d disposed in the field of view to be captured (specifically, an area in an angle of view of the imaging unit 9) of the capsule endoscope 32 in an inserted state.

Also, the cap 30 has a magnet 30a. The magnet 30a switches the luminescent color of the capsule endoscope 32 being inserted in the cap 30, and is disposed near the inner wall surface of the cap 30 in contact with the case main body 6a of the capsule endoscope 32 in an inserted state. Specifically, the magnet 30a is disposed near the opening of the cap 30.

The capsule endoscope 32 has magnetic sensors 33a to 33c that detects the magnetism of the magnet 30a and has a function of, in a state of being inserted in the inner space of the cap 30 (that is, in a state where the cap 30 is mounted), switching the luminescent color based on the magnetism detection result of the magnetic sensors 33a to 33c. Specifically, as depicted in FIG. 17, as with the capsule endoscope 22 in the modification example of the second embodiment described above, the capsule endoscope 32 has, in the capsule casing 6, the light-emitting units 8a to 8c, the imaging unit 9, the communicating unit 10, and the power supply unit 12, and further has the magnetic sensors 33a to 33c and a switch circuit 34. Also, the capsule endoscope 32 has a control unit 35 in place of the control unit 11 of the capsule endoscope 22 in the modification example of the second embodiment described above. Other than a function of switching the luminescent color based on the magnetism detection result of the magnetic sensors 33a tot 33c, the capsule endoscope 32 has functions similar to those of the capsule endoscope 22.

As described above, the magnetic sensors 33a to 33c detect the magnetism of the magnet 30a with the capsule endoscope 32 having the cap 30 mounted thereon, and transmits the magnetism detection result to the control unit 35. Specifically, the magnetic sensors 33a to 33c are disposed in a distributed manner on the inner wall surface of the case main body 6a and near the optical dome 6b. These magnetic sensors 33a to 33c detect the intensity of the magnetism output from the magnet 30a, and transmit a magnetism detection signal to the control unit 35 when the detected magnetic intensity is equal to or greater than a predetermined threshold.

The switch circuit 34 instructs to switch the luminescent color of the capsule endoscope 32 based on the magnetism detection result of the magnetic sensors 33a to 33c. Specifically, the switch circuit 34 switches the conduction state between the light-emitting units 8a to 8c and the power supply unit 12 based on the control of the control unit 35. Examples of patterns of the conduction state between the light-emitting units 8a to 8c and the power supply unit 12 to be switched by the switch circuit 34 include a pattern in which only the light-emitting unit 8a and the power supply unit 12 are caused to be in a conduction state, a pattern in which only the light-emitting unit 8b and the power supply unit 12 are caused to be in a conduction state, a pattern in which only the light-emitting unit 8c and the power supply unit 12 are caused to be in a conduction state, and a pattern in which the light-emitting units 8a to 8c and the power supply unit 12 are caused to be in a conduction state.

The control unit 35 controls each of the component units of the capsule endoscope 32 (the light-emitting units 8a to 8c, the imaging unit 9, the communicating unit 10, the magnetic sensors 33a to 33c, and the switch circuit 34), and also controls inputs and outputs of signals among the component units. Specifically, the control unit 35 is constructed by using a CPU that performs various processes, a ROM having process programs or the like stored therein, and a RAM having various information temporarily stored therein. The control unit 35 controls each magnetism detecting operation of the magnetic sensors 33a to 33c, controls the switching operation of the switch circuit 34, controls the light-emitting operation of the light-emitting units 8a to 8c via the switch circuit 34, and controls the imaging operation of the imaging unit 9.

Also, the control unit 35 controls the light-emission driving timing of the light-emitting units 8a to 8c and the imaging driving timing of the imaging unit 9 correspondingly to the pattern of the conduction state switched by the switch circuit 34 described above. Specifically, when acquiring a magnetism detection signal from the magnetic sensor 33a, the control unit 35 controls the switch circuit 34 so that only the light-emitting unit 8a and the power supply unit 12 are brought into a conduction state. In this case, the control unit 35 controls the light-emitting unit 8a so that it emits red light, and controls the imaging unit 9 so that it receives reflected light from the field of view to be captured illuminated with the red light (that is, it captures an image in the field of view to be captured). Also, when acquiring a magnetism detection signal from the magnetic sensor 33b, the control unit 35 controls the switch circuit 34 so that only the light-emitting unit 8b and the power supply unit 12 are brought into a conduction state. In this case, the control unit 35 controls the light-emitting unit 8b so that it emits green light, and controls the imaging unit 9 so that it receives reflected light from the field of view to be captured illuminated with the green light. Furthermore, when acquiring a magnetism detection signal from the magnetic sensor 33c, the control unit 35 controls the switch circuit 34 so that only the light-emitting unit 8c and the power supply unit 12 are brought into a conduction state. In this case, the control unit 35 controls the light-emitting unit 8c so that it emits blue light, and controls the imaging unit 9 so that it receives reflected light from the field of view to be captured illuminated with the blue light. When not acquiring a magnetism detection signal from any of the magnetic sensors 33a to 33c for a predetermined time or more, for example, the control unit 35 controls the switch circuit 34 so that the light-emitting units 8a to 8c and the power supply unit 12 are brought into a conduction state. In this case, the control unit 35 controls the light-emitting units 8a to 8c so that they simultaneously emit red light, green light, and blue light, respectively, and controls the imaging unit 9 so that it receives reflected light from the field of view to be captured illuminated with white light formed by simultaneous light emission.

Figure 18:
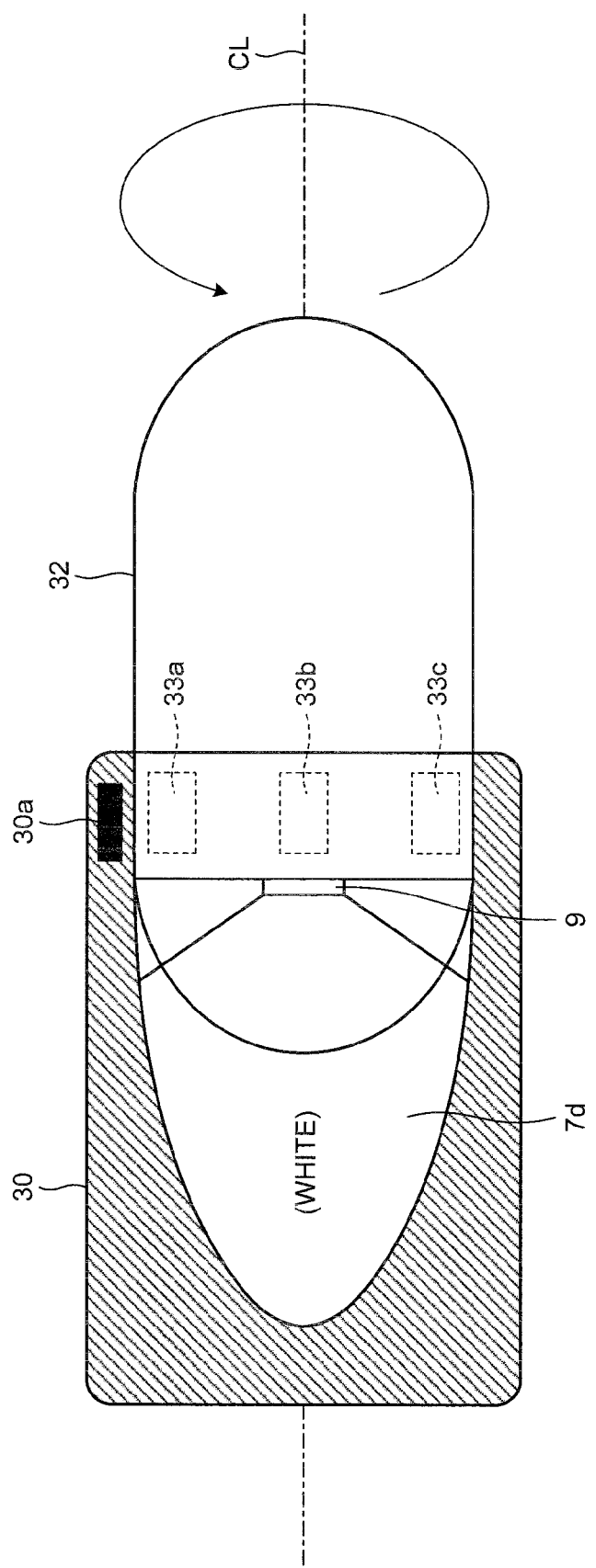
FIG. 18 is a schematic diagram exemplifying a state of sequentially switching a luminescent color with the capsule endoscope having a cap mounted thereon to sequentially capture chart images in frame.
Figure 19:
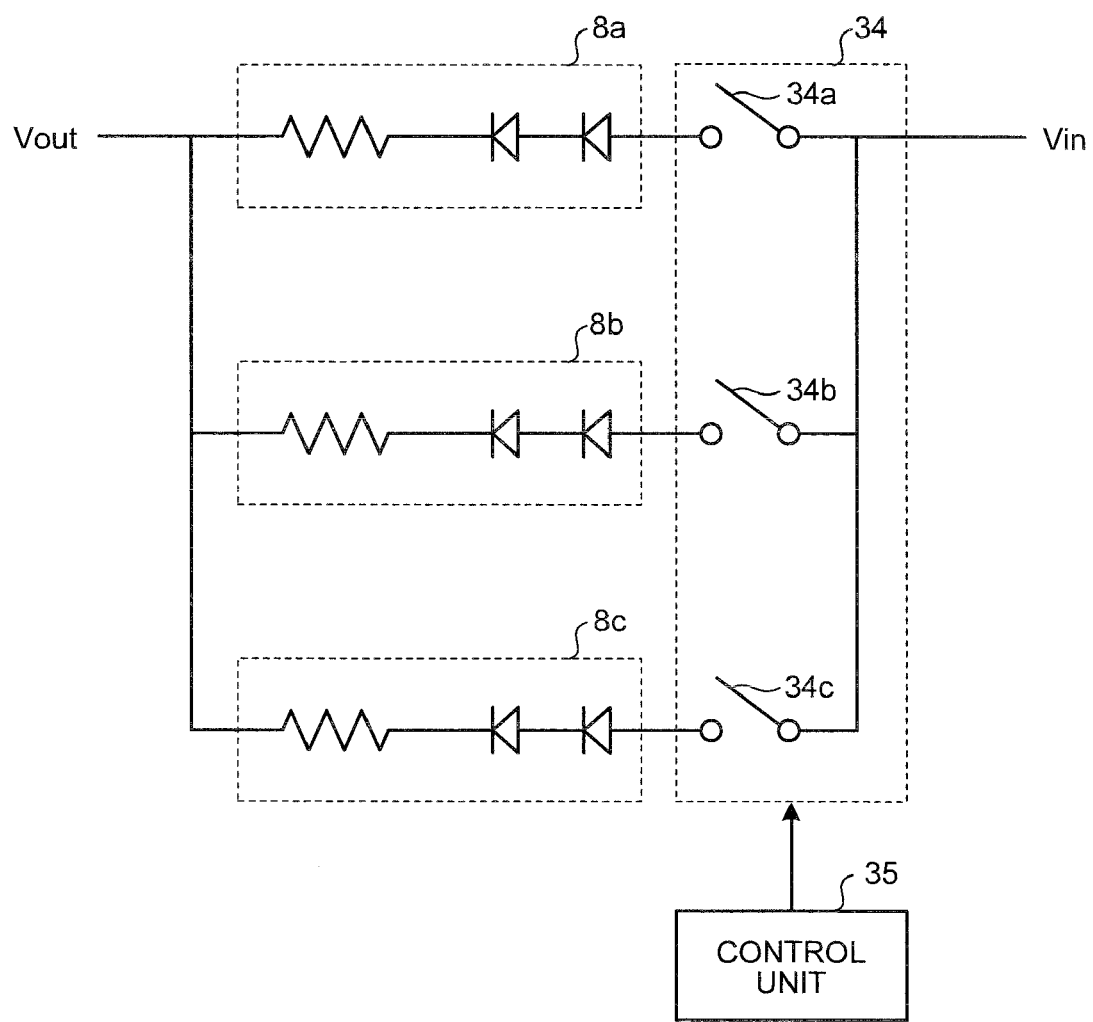
FIG. 19 is a circuit diagram explaining a switching operation of a switch circuit.

Next, the operation of the capsule endoscope 32 is specifically described, which includes the operation of switching the luminescent color based on the magnetism detection result of the magnetic sensors 33a to 33c to sequentially capture the chart images PR, PG, PB, and PW for each frame. FIG. 18 is a schematic diagram exemplifying a state of sequentially switching luminescent colors with the capsule endoscope 32 having the cap mounted thereon to sequentially capture the chart images PR, PG, PB, and PW for each frame. FIG. 19 is a circuit diagram explaining a switching operation of the switch circuit 34. Note in FIG. 18 that a side section view of the cap 30 is depicted for easy understanding of the state in which the capsule endoscope 32 captures each chart image for each frame.

As depicted in FIGS. 18 and 19, the capsule endoscope 32 starts the simultaneous light emission of each of RGB color lights by an external magnetic force (not shown), and also has the cap 30 mounted thereon before being inserted into an organ of the subject 100. In this state, the capsule endoscope 32 rotationally moves relative to the cap 30 while sliding on the inner wall surface of the cap 30, with a center axis CL in a longitudinal direction of the casing 6 taken as a rotation axis. In this case, the capsule endoscope 32 sequentially changes each relative position of the magnet 30a of the cap 30 and the magnetic sensors 33a to 33c by the rotation.

Here, when a relative position distance between the magnetic sensor 33a and the magnet 30a is shorter than a predetermined distance, the magnetic sensor 33a detects a magnetic intensity equal to or greater than a predetermined threshold from this near magnet 30a. In this case, the magnetic sensor 33a transmits a magnetism detection signal to the control unit 35. In this state, since a relative position distance between each of the remaining magnetic sensors 33b and 33c and the magnet 30a is equal to or longer than the predetermined distance, these sensors do not detect a magnetic intensity equal to or greater than the predetermined threshold. Therefore, the magnetic sensors 33b and 33c do not transmit a magnetism detection signal to the control unit 35.

When the magnetic sensor 33a transmits a magnetism detection signal to the control unit 35, the control unit 35 controls the switch circuit 34 based on the magnetism detection signal from the magnetic sensor 33a so that the switch circuit 34 brings only the light-emitting unit 8a and the power supply unit 12 into a conduction state for each predetermined time. Based on the control of the control unit 35, the switch circuit 34 closes only a switch 34a depicted in FIG. 19 for each predetermined time to cause only the light-emitting unit 8a and the power supply unit 12 to be in a conduction state. In such a conduction state, the light-emitting unit 8a emits red light for each predetermined time to the white chart 7d inside of the cap 30.

When the red light from the light-emitting unit 8a illuminates the white chart 7d, the imaging unit 9 receives red light reflected from the white chart 7d to capture the chart image PR for each frame. The chart image PR for each frame is wirelessly transmitted to the receiving device 27 as described above.

When a relative position distance between the magnetic sensor 33b and the magnet 30a is shorter than the predetermined distance, the magnetic sensor 33b detects a magnetic intensity equal to or greater than the predetermined threshold from this near magnet 30a. In this case, the magnetic sensor 33b transmits a magnetism detection signal to the control unit 35. In this state, since a relative position distance between each of the remaining magnetic sensors 33a and 33c and the magnet 30a is equal to or longer than the predetermined distance, these sensors do not detect a magnetic intensity equal to or greater than the predetermined threshold from the magnet 30a. Therefore, the magnetic sensors 33a and 33c do not transmit a magnetism detection signal to the control unit 35.

When the magnetic sensor 33b transmits a magnetism detection signal to the control unit 35, the control unit 35 controls the switch circuit 34 based on the magnetism detection signal from the magnetic sensor 33b so that the switch circuit 34 brings only the light-emitting unit 8b and the power supply unit 12 into a conduction state for each predetermined time. Based on the control of the control unit 35, the switch circuit 34 closes only a switch 34b depicted in FIG. 19 for each predetermined time to cause only the light-emitting unit 8b and the power supply unit 12 to be in a conduction state. In such a conduction state, the light-emitting unit 8b emits green light for each predetermined time to the white chart 7d inside of the cap 30.

When the green light from the light-emitting unit 8b illuminates the white chart 7d, the imaging unit 9 receives green light reflected from the white chart 7d to capture the chart image PG for each frame. The chart image PG for each frame is wirelessly transmitted to the receiving device 27 as described above.

When a relative position distance between the magnetic sensor 33c and the magnet 30a is shorter than the predetermined distance, the magnetic sensor 33c detects a magnetic intensity equal to or greater than the predetermined threshold from this near magnet 30a. In this case, the magnetic sensor 33c transmits a magnetism detection signal to the control unit 35. In this state, since a relative position distance between each of the remaining magnetic sensors 33a and 33b and the magnet 30a is equal to or longer than the predetermined distance, these sensors do not detect a magnetic intensity equal to or greater than the predetermined threshold from the magnet 30a. Therefore, the magnetic sensors 33a and 33b do not transmit a magnetism detection signal to the control unit 35.

When the magnetic sensor 33c transmits a magnetism detection signal to the control unit 35, the control unit 35 controls the switch circuit 34 based on the magnetism detection signal from the magnetic sensor 33c so that the switch circuit 34 brings only the light-emitting unit 8c and the power supply unit 12 into a conduction state for each predetermined time. Based on the control of the control unit 35, the switch circuit 34 closes only a switch 34c depicted in FIG. 19 for each predetermined time to cause only the light-emitting unit 8c and the power supply unit 12 to be in a conduction state. In such a conduction state, the light-emitting unit 8c emits blue light for each predetermined time to the white chart 7d inside of the cap 30.

When the blue light from the light-emitting unit 8c illuminates the white chart 7d, the imaging unit 9 receives blue light reflected from the white chart 7d to capture the chart image PB for each frame. The chart image PB for each frame is wirelessly transmitted to the receiving device 27 as described above.

When a relative position distance between any of the magnetic sensor 33a to 33c and the magnet 30a is equal to or longer than the predetermined distance, none of the magnetic sensors 33a to 33c detect a magnetic intensity equal to or greater than the predetermined threshold from the magnet 30a. In this case, the magnetic sensors 33a to 33c do not transmit a magnetism detection signal to the control unit 35.

In this state, the control unit 35 controls the switch circuit 34 so that the switch circuit 34 approximately simultaneously brings all of the light-emitting units 8a to 8c and the power supply unit 12 into a conduction state for each predetermined time. Based on the control of the control unit 35, the switch circuit 34 simultaneously closes the switches 34a to 34c depicted in FIG. 19 for each predetermined time. With this, the switch circuit 34 causes all of the light-emitting units 8a to 8c and the power supply unit 12 to be approximately simultaneously in a conduction state for each predetermined time. In such a conduction state, the light-emitting units 8a to 8c simultaneously emit red light, green light, and blue light, respectively, to the white chart 7d inside of the cap 30.

When white light formed of the red light, the green light, and the blue light from the light-emitting units 8a to 8c illuminates the white chart 7d, the imaging unit 9 receives white light reflected from the white chart 7d to capture the chart image PW for each frame. The chart image PW for each frame is wirelessly transmitted to the receiving device 27 as described above.

In this manner, the capsule endoscope 32 sequentially and wirelessly transmits each piece of chart image information about the chart images PR, PG, PB, and PW for each frame to the receiving device 27. Then, the capsule endoscope 32 is inserted into the organ of the subject 100 with the cap 30 removed therefrom. The capsule endoscope 32 sequentially captures in-vivo images of the subject 100, and sequentially and wirelessly transmits the in-vivo images to the receiving device 27.

As described in the foregoing, in the third embodiment of the present invention, when chart images of plural colors are to be captured, light-emitting timings of the plural light-emitting units that emit color lights of plural colors forming a white light are switched, and color lights of plural colors including white light are sequentially emitted to a white chart. The color lights of the plural colors reflected from the white chart are sequentially received. Other configuration is similar to that of the modification example of the second embodiment described above. Therefore, without requiring a color chart of plural colors, chart images of plural colors including white can be sequentially captured for each frame by using only the white chart. As a result, operations and effects similar to those of the modification example of the second embodiment described above can be obtained, and also chart images of plural colors can be captured with a simple apparatus configuration.

Modification Example of The Third Embodiment

Next, a modification example of the third embodiment of the present invention is described. In the third embodiment described above, the capsule endoscope 32 is rotated relative to the cap 30 that has the magnet 30a, thereby sequentially switching the luminescent color of the capsule endoscope 32. In the modification example of the third embodiment, the luminescent color of the capsule endoscope with the cap mounted thereon is changed with time to sequentially emit color lights of plural colors including white light to a white chart formed on the inner wall surface of the cap, thereby sequentially capturing the chart images PR, PG, PB, and PW for each frame.

Figure 20:
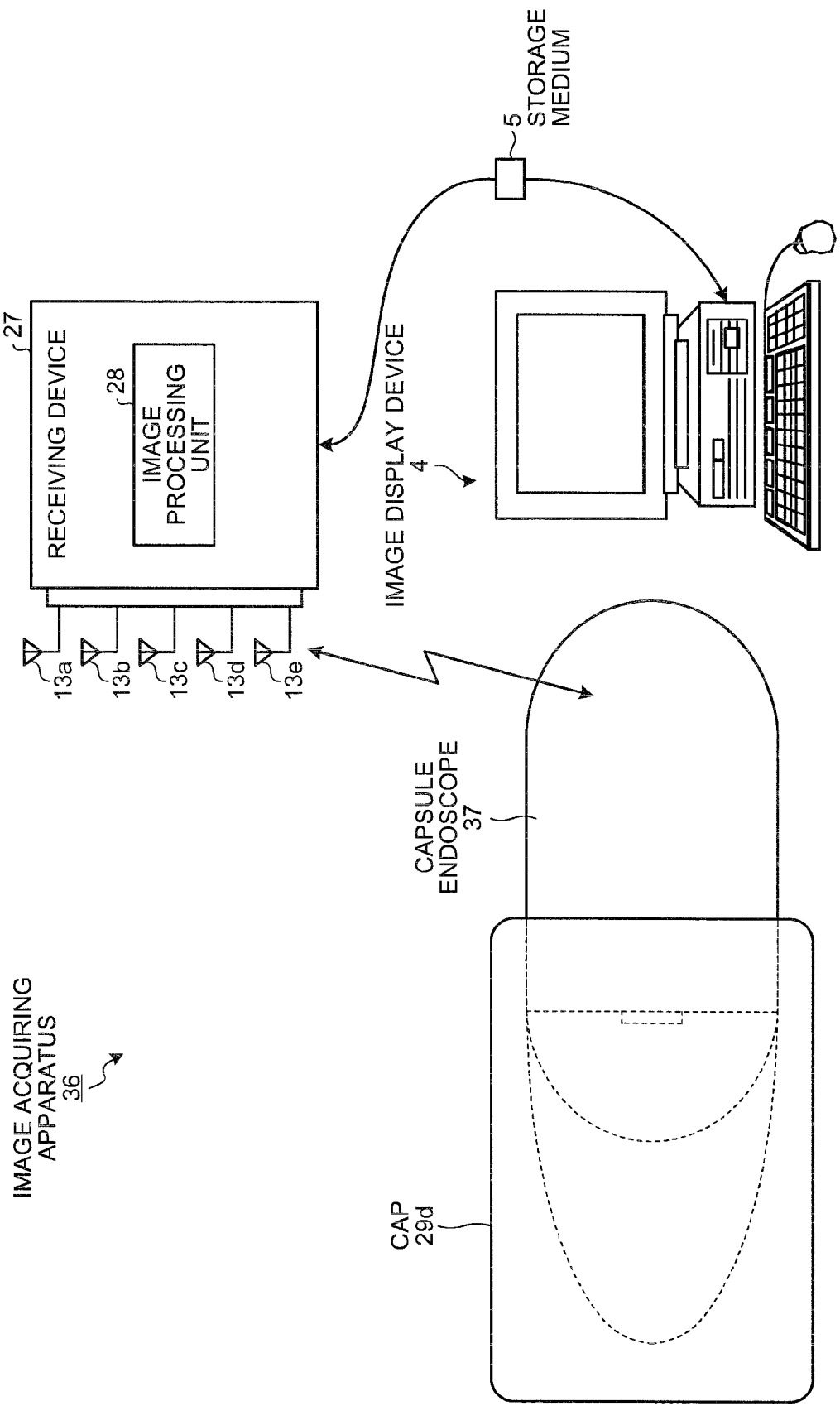
FIG. 20 is a schematic diagram depicting a configuration example of an observation apparatus according to a modification example of the third embodiment of the present invention.
Figure 21:
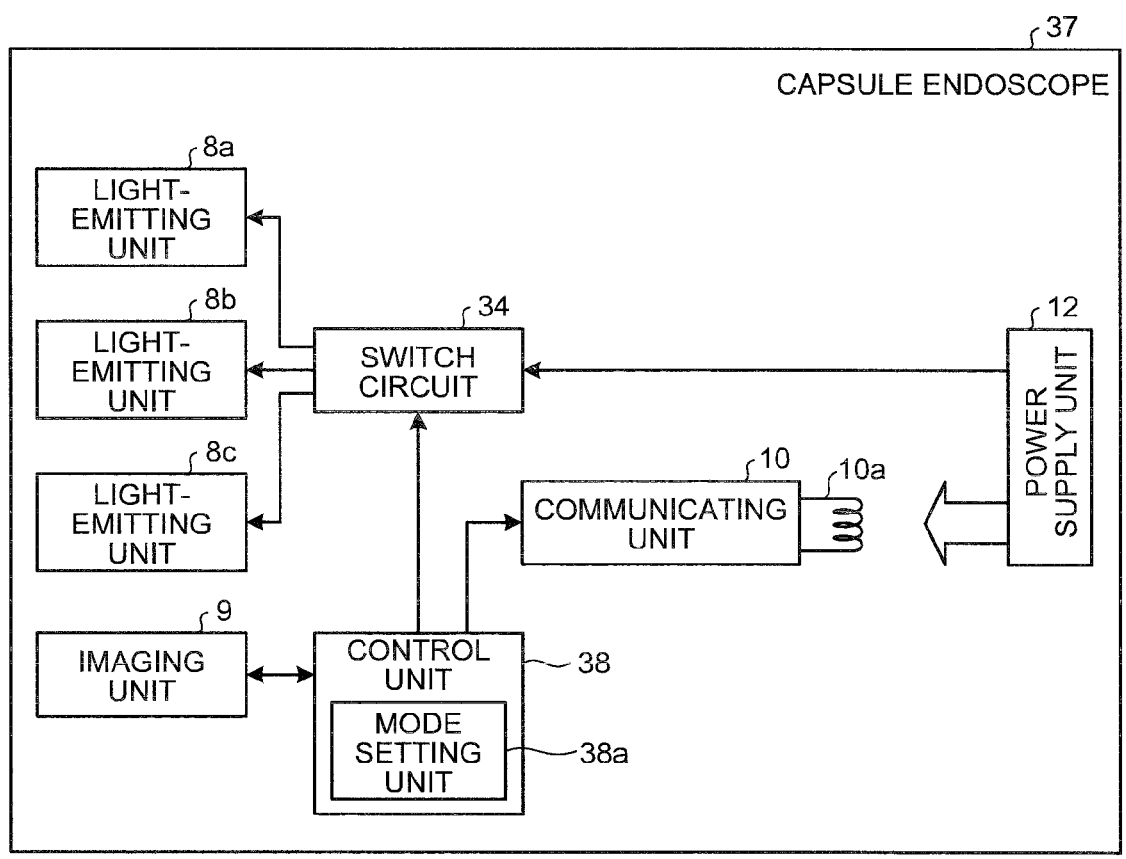
FIG. 21 is a block diagram schematically exemplifying the functional configuration of a capsule endoscope of the observation apparatus according to the modification example of the third embodiment.

FIG. 20 is a schematic diagram depicting a configuration example of an observation apparatus according to the modification example of the third embodiment of the present invention. FIG. 21 is a block diagram schematically exemplifying the functional configuration of a capsule endoscope of the observation apparatus according to the modification example of the third embodiment. As depicted in FIGS. 20 and 21, an image acquiring apparatus 36, which is an observation apparatus according to the modification example of the third embodiment, has the cap 29d (refer to the modification example of the second embodiment) in place of the cap 30 of the image acquiring apparatus 31 according to the third embodiment described above, and a capsule endoscope 37 in place of the capsule endoscope 32. Other configurations are the same as those of the first embodiment, and the same component units are denoted with the same reference numerals.

The capsule endoscope 37 has a function of, in a state where the cap 29d that has the white chart 7d on its inner wall surface is mounted thereon, changing the luminescent color of color light emitted to the white chart 7d with time. Color lights of plural colors (including white light) reflected from the white chart 7d are received, and the chart images PR, PG, PB, and PW are sequentially captured for each frame. Other functions of the capsule endoscope 37 are similar to those of the capsule endoscope 32 of the third embodiment described above.

As depicted in FIG. 21, as with the capsule endoscope 32 of the third embodiment described above, the capsule endoscope 37 has, in the capsule casing 6, the light-emitting units 8a to 8c, the imaging unit 9, the communicating unit 10, the power supply unit 12, and the switch circuit 34. Also, the capsule endoscope 37 has a control unit 38 in place of the control unit 35 of the capsule endoscope 32 described above, and does not have the magnetic sensors 33a to 33c described above.

The control unit 38 controls each of the component units (the light-emitting units 8a to 8c, the imaging unit 9, the communicating unit 10, and the switch circuit 34) of the capsule endoscope 37, and also controls inputs and outputs of signals among the component units. Specifically, the control unit 38 is constructed by using a CPU that performs various processes, a ROM having process programs or the like stored therein, and a RAM having various information temporarily stored therein. The control unit 38 controls the switch circuit 34 so that, when the power supply unit 12 starts power supply by an external magnetic force, conduction states of the light-emitting units 8a to 8c and the power supply unit 12 are sequentially switched with time via the switch circuit 34. With this, the luminescent color of the capsule endoscope 37 is changed with time. Other functions of the control unit 38 are similar to those of the control unit 35 of the capsule endoscope 32 described above.

The control unit 38 has a mode setting unit 38a that sets a switching operation mode of the switch circuit 34. Corresponding to an elapsed time from the time when the power supply unit 12 starts power supply by an external magnetic force, the mode setting unit 38a sets the switching operation mode of the switch circuit 34 to either one of an individual light-emitting mode and a simultaneous light-emitting mode. Note that the individual light-emitting mode is a switching operation mode for individually driving the light-emitting units 8a to 8c for light emission for each predetermined time. The simultaneous light-emitting mode is a switching operation mode for approximately simultaneously driving the light-emitting units 8a to 8c for light emission for each predetermined time.

When the individual light-emitting mode is set, the control unit 38 controls the switch circuit 34 so that the light-emitting unit in the light-emitting units 8a to 8c that becomes in a conduction state with respect to the power supply unit 12 is sequentially switched for each predetermined time. When the simultaneous light-emitting mode is set, the control unit 38 controls the switch circuit 34 so that all of the light-emitting units 8a to 8c and the power supply unit 12 are approximately simultaneously brought into a conduction state for each predetermined time.

Figure 22:
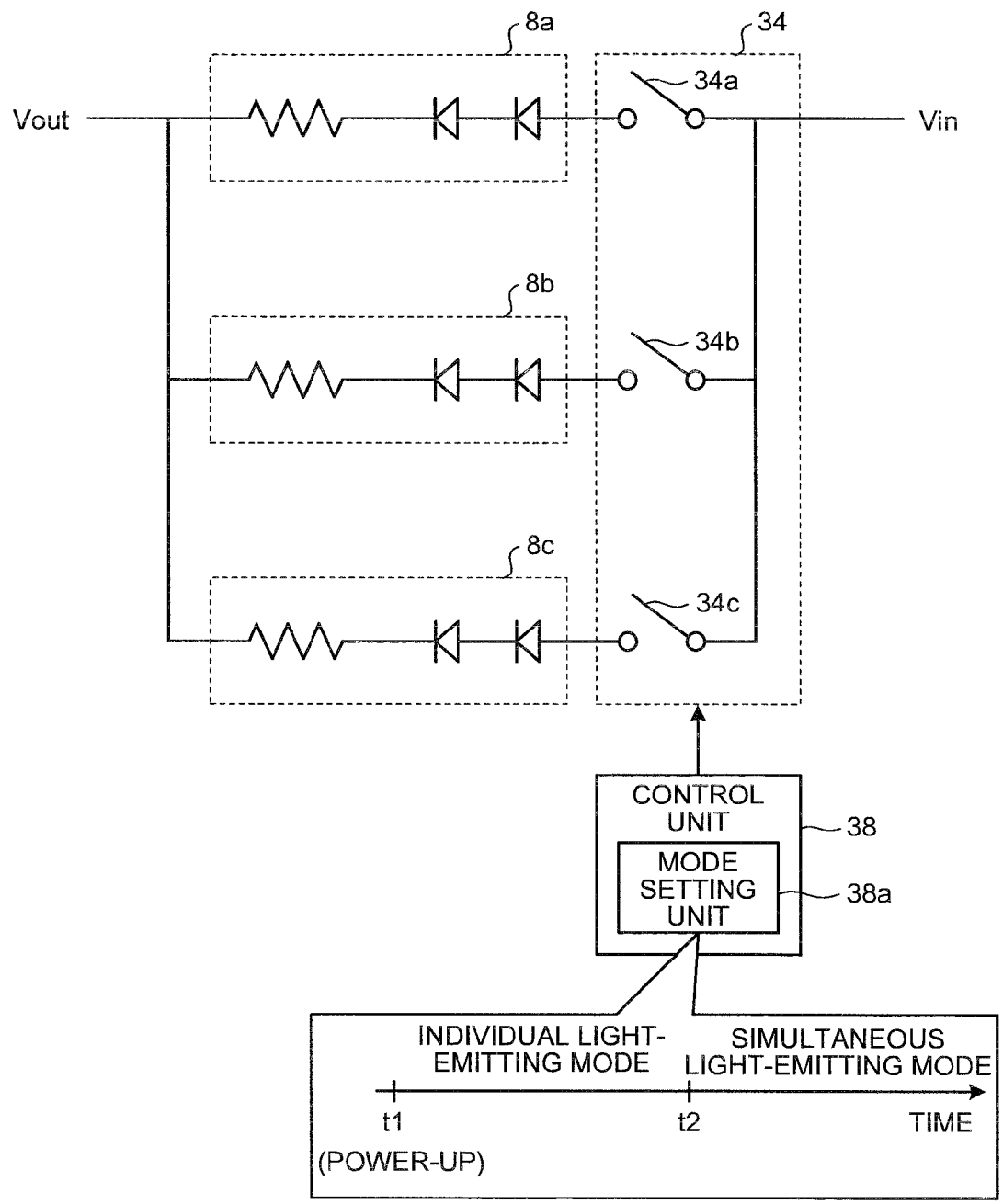
FIG. 22 is a schematic diagram explaining an operation of the capsule endoscope that switches a conduction state between plural light-emitting units and a power supply unit with time to change a luminescent color with time.

Next, the operation of the capsule endoscope 37 is specifically described, which includes the operation of switching the luminescent color of the color light emitted to the white chart 7d with time to sequentially capture the chart images PR, PG, PB, and PW for each frame. FIG. 22 is a schematic diagram explaining the operation of the capsule endoscope 37 that switches a conduction state between the light-emitting units 8a to 8c and the power supply unit 12 with time via the switch circuit 34 to change the luminescent color onto the white chart 7d with time.

Before inserted into an organ of the subject 100, the capsule endoscope 37 starts power supply of the power supply unit 12 by an external magnetic force (not shown), and then has the cap 29d mounted thereon. In this state, as depicted in FIG. 22, the mode setting unit 38a sets an individual light-emitting mode as a switching operation mode of the switch circuit 34 during a period from a time t1 when the power supply unit 12 starts power supply (power-up time) to a predetermined time t2.

When the individual light-emitting mode is set, the control unit 38 controls the switch circuit 34 so that the patterns of the conduction state of the light-emitting units 8a to 8c and the power supply unit 12 are sequentially switched in a predetermined order for each predetermined time. The patterns of the conduction state include, as described above, a pattern in which only the light-emitting unit 8a and the power supply unit 12 are brought into a conduction state, a pattern in which only the light-emitting unit 8b and the power supply unit 12 are brought into a conduction state, and a pattern in which only the light-emitting unit 8c and the power supply unit 12 are brought into a conduction state. The control unit 38 controls the switch circuit 34 so that the pattern of the conduction state repeats for one cycle or more.

Based on the control of the control unit 38 in the individual light-emitting mode, the switch circuit 34 sequentially closes the switches 34a to 34c for each predetermined time in the predetermined order. With this, the light-emitting units 8a to 8c sequentially emit red light, green light, and blue light, respectively, onto the white chart 7d for each predetermined time in the predetermined order. In this manner, red light, green light, and blue light sequentially emitted from the light-emitting units 8a to 8c, respectively, individually illuminate the white chart 7d.

In this case, the imaging unit 9 sequentially receives red light, green light, and blue light individually reflected from the white chart 7d, thereby sequentially capturing the chart images PR, PG, and PB for each frame. These chart images PR, PG, and PB for each frame are wirelessly transmitted to the receiving device 27, as described above.

As depicted in FIG. 22, when the predetermined time t2 elapses from the time t1 described above, the mode setting unit 38a sets the simultaneous light-emitting mode as a switching operation mode of the switch circuit 34. In this case, the control unit 38 controls the switch circuit 34 so that all of the light-emitting units 8a to 8c and the power supply unit 12 are approximately simultaneously brought into a conduction state for each predetermined time.

Based on the control of the control unit 38 in the simultaneous light-emitting mode, the switch circuit 34 approximately simultaneously opens and closes all of the switches 34a to 34c for each predetermined time. With this, the light-emitting units 8a to 8c simultaneously emit red light, green light, and blue light, respectively, onto the white chart 7d for each predetermined time. The red light, green light, and blue light thus approximately simultaneously emitted from the light-emitting units 8a to 8c, respectively, illuminate the white chart 7d in a state of forming a white light.

In this case, the imaging unit 9 receives white light reflected from the white chart 7d to capture the chart image PW for each frame. The chart image PW for each frame is wirelessly transmitted to the receiving device 27, as described above.

In this manner, the capsule endoscope 37 sequentially and wirelessly transmits each piece of chart image information about the chart images PR, PG, PB, and PW for each frame to the receiving device 27. Then, the capsule endoscope 37 with the cap 29d removed therefrom is inserted into the organ of the subject 100. While capturing an in-vivo image of the subject 100, the capsule endoscope 37 sequentially and wirelessly transmits the in-vivo image to the receiving device 27.

As described in the foregoing, in the modification example of the third embodiment of the present invention, when chart images of plural colors are to be captured, light-emitting timings of the plural light-emitting units that emit color lights of plural colors forming a white light are automatically switched along a time axis to sequentially emit the color lights of the plural colors including white light onto the white chart, thereby sequentially receiving the color lights of the plural colors reflected from the white chart. Other configuration is similar to that of the third embodiment described above. Therefore, it is possible to save effort to rotate the capsule endoscope relatively to the cap having the white chart on its inner wall surface. Thus, operations and effects similar to those of the third embodiment described above can be obtained, and also chart image information about plural colors required for calculating various correction coefficients described above can be easily and reliably acquired.

Fourth Embodiment

Next, a fourth embodiment of the present invention is described. In the modification example of the third embodiment described above, the completed capsule endoscope 37 is used to acquire chart image information about plural colors. In the fourth embodiment, in the process of assembling the capsule endoscope, an incomplete capsule endoscope without the capsule casing 6 is used to acquire chart image information about plural colors, thereby calculating various correction coefficients, such as the correction matrix and the white-balance correction coefficient as described above.

Figure 23:
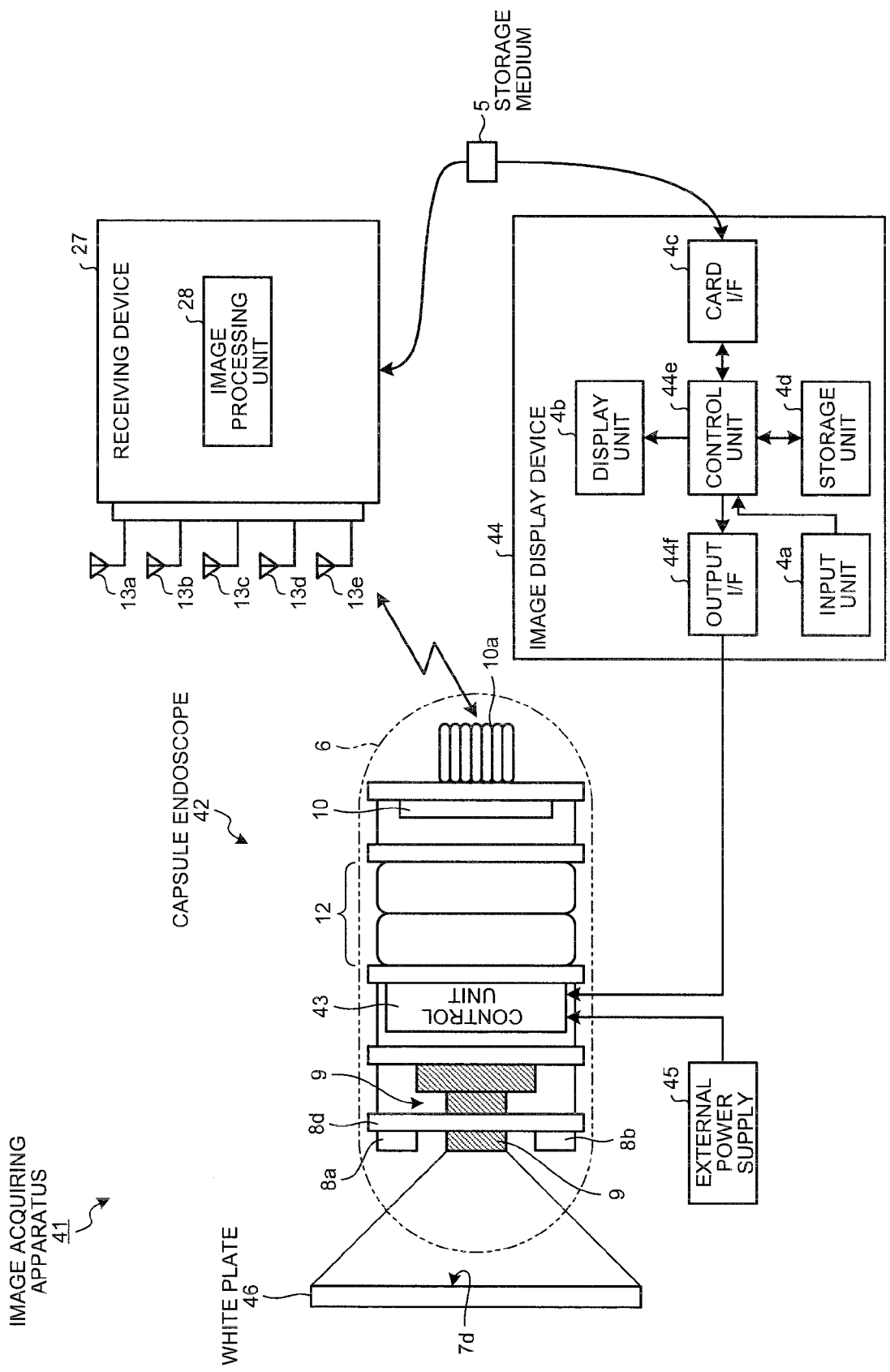
FIG. 23 is a schematic diagram depicting a configuration example of an observation apparatus according to a fourth embodiment of the present invention.
Figure 24:
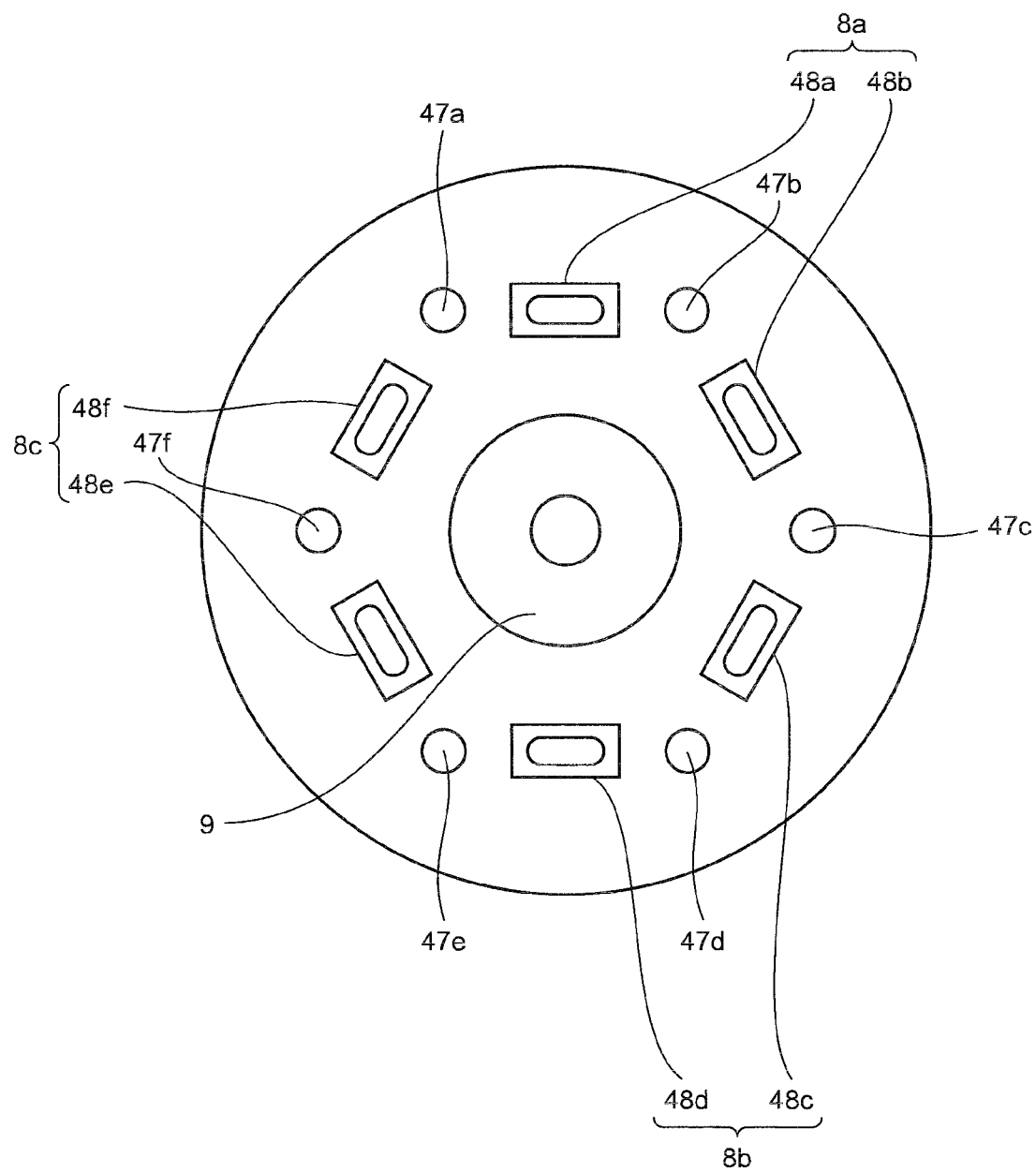
FIG. 24 is a schematic diagram of the state of an illumination substrate included in a capsule endoscope according to the fourth embodiment of the present invention.
Figure 25:
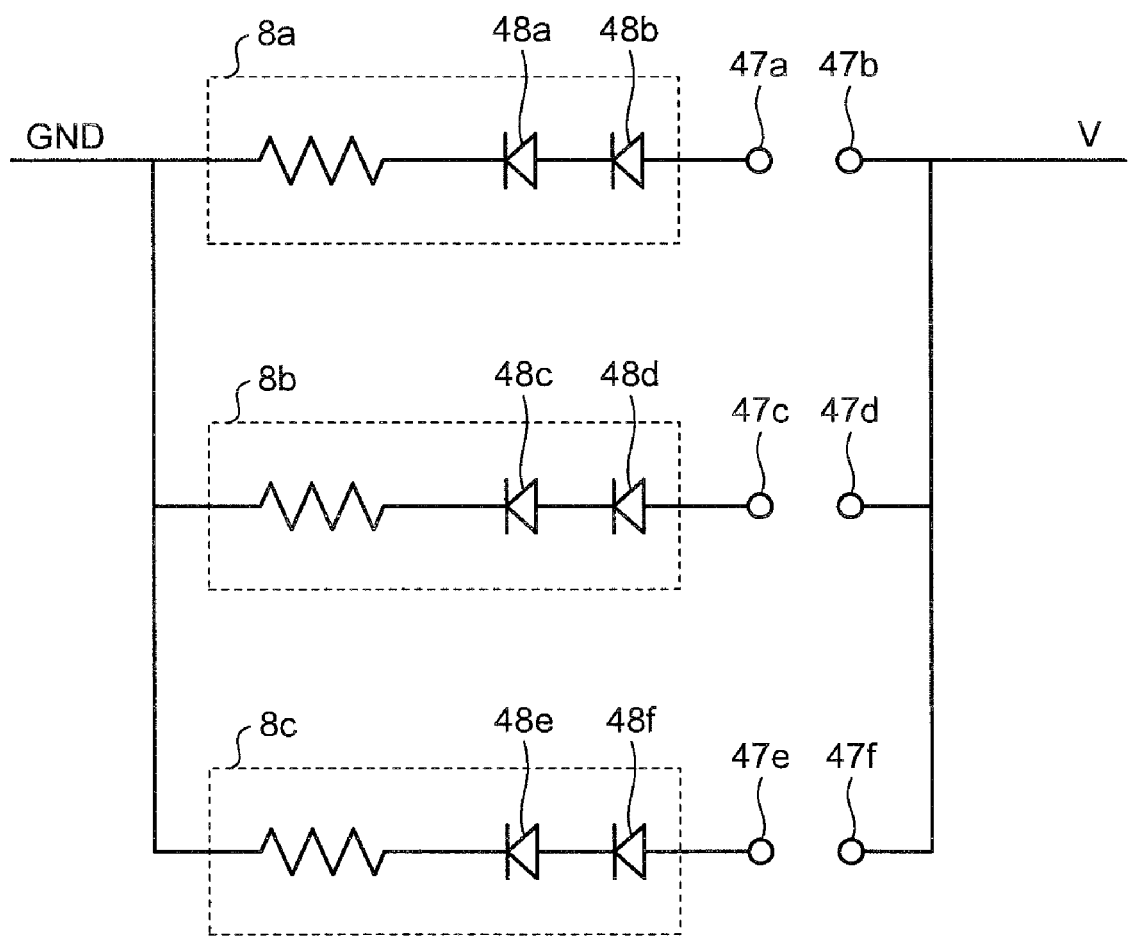
FIG. 25 is a circuit diagram schematically depicting a circuit configuration example of the illumination substrate.

FIG. 23 is a schematic diagram depicting a configuration example of an observation apparatus according to the fourth embodiment of the present invention. FIG. 24 is a schematic diagram of the state of an illumination substrate included in a capsule endoscope according to the fourth embodiment of the present invention. FIG. 25 is a circuit diagram schematically depicting a circuit configuration example of the illumination substrate. As depicted in FIGS. 23 to 25, an image acquiring apparatus 41, which is an observation apparatus according to the fourth embodiment, has a capsule endoscope 42 in place of the capsule endoscope 37 of the image acquiring apparatus 36 according to the modification example of the third embodiment described above, an image display device 44 in place of the image display device 4, and a white plate 46 in place of the cap 29d, and further has an external power supply 45. Other configurations are the same as those of the modification example of the third embodiment, and the same component units are denoted with the same reference numerals.

The capsule endoscope 42 has the light-emitting units 8a to 8c, the imaging unit 9, the communicating unit 10, and the power supply unit 12 described above. Also, the capsule endoscope 42 has an illumination substrate 8d, on which plural electrode pads 47a to 47f are formed, and a control unit 43 that controls each component unit of the capsule endoscope 42. In an incomplete state in the process of assembling, the capsule endoscope 42 sequentially receives color lights of plural colors including white light to capture the chart images PR, PG, PB, and PW of the plural colors, and sequentially and wirelessly transmits each piece of chart image information about the chart images PR, PG, PB, and PW of the plural colors to the receiving device 27. Then, the capsule endoscope 42 in such an incomplete state acquires various correction coefficients (such as the correction matrix, the white-balance correction coefficient, and the gamma value)

calculated by the image processing unit 28 of the receiving device 27. Note that the capsule endoscope 42 is completed by accommodating, in the capsule casing 6, the light-emitting units 8a to 8c, the illumination substrate 8d with the electrode pads 47a to 47f connected, the imaging unit 9, the communicating unit 10, the power supply unit 12, and the control unit 43, which are component units of the capsule endoscope 42.

As depicted in FIG. 24, the illumination substrate 8d has the plural electrode pads 47a to 47f formed thereon, and plural light-emitting elements 48a to 48f are mounted thereon. Within these plural light-emitting elements 48a to 48f, the light-emitting elements 48a and 48b are light-emitting elements of the light-emitting unit 8a that emits red light, the light-emitting elements 48c and 48d are light-emitting elements of the light-emitting unit 8b that emits green light, and the light-emitting elements 48e and 48f are light-emitting elements of the light-emitting unit 8c that emits blue light. Also, among these electrode pads 47a to 47f, the electrode pads 47a and 47b electrically connect the light-emitting unit 8a that has the light-emitting elements 48a and 48b and the external power supply 45 together, the electrode pads 47c and 47d electrically connect the light-emitting unit 8b that has the light-emitting elements 48c and 48d and the external power supply 45 together, and the electrode pads 47e and 47f electrically connect the light-emitting unit 8c that has the light-emitting elements 48e and 48f and the external power supply 45 together. On the illumination substrate 8d, as depicted in FIG. 25, a circuit for switching conduction states of the light-emitting units 8a to 8c and the external power supply 45 is formed. Note that a through hole is formed on an approximately center portion of the illumination substrate 8d. In the through hole of the illumination substrate 8d, an optical system (such as a lens holder) of the imaging unit 9 is inserted.

The control unit 43 controls each of the component units of the capsule endoscope 42 (the light-emitting units 8a to 8c, the imaging unit 9, and the communicating unit 10), and also controls inputs and outputs of signals among the component units. Specifically, the control unit 43 is constructed by using a CPU that performs various processes, a ROM having process programs or the like stored therein, and a RAM having various information temporarily stored therein. The control unit 43 has plural external terminals and is connected to the image display device 44 and the external power supply 45 via a cable or the like. The control unit 43 supplies power from the external power supply 45 to the light-emitting elements 48a to 48f, depending on the connection state of the electrode pads 47a to 47f described above. Also, the control unit 43 controls the imaging unit 9 so that it consumes power supplied from the external power supply to capture the chart images PR, PG, PB, and PW of the plural colors, and controls the communicating unit 10 so that it wirelessly transmits each piece of chart image information about the chart images PR, PG, PB, and PW to the receiving device 27.

The control unit 43 acquires various correction coefficients (such as the correction matrix, the white-balance correction coefficient, and the gamma value) calculated by the image processing unit 28 of the receiving device 27 via the image display device 44, and stores the acquired various correction coefficients in its ROM. The control unit 43 generates an image signal containing the in-vivo image and the various correction coefficients, and controls the communicating unit 10 so that, when the imaging unit 9 captures an in-vivo image, the communicating unit 10 wirelessly transmits the image signal to the receiving device 27.

Note that the control unit 43 is connected to the external power supply 45 via a cable or the like until various correction coefficients are acquired as described above, consuming power supplied from the external power supply 45. When power supply to the power supply unit 12 starts by an external magnetic force after the capsule endoscope 42 is completed, the control unit 43 consumes power from the power supply unit 12. As a result, the power of the power supply unit 12 is not consumed by the control unit 43 until it acquires various correction coefficients. Therefore, power to be supplied when the capsule endoscope 42 is inserted into an organ of the subject 100 can be saved.

The image display device 44 has a control unit 44e in place of the control unit 4e of the image display device 4 (refer to FIG. 1) according to the first embodiment described above, and further has an output I/F 44f. Other configurations are the same as those of the image display device 4 of the first embodiment, and the same component units are denoted with the same reference numerals.

The output I/F 44f is connected to the control unit 43 of the capsule endoscope 42 via a cable or the like, and transmits information to be transmitted upon instruction from the control unit 44e (such as various correction coefficients, for example) to the control unit 43. The control unit 44e acquires various correction coefficients from the receiving device 27 via the portable storage medium 5. Specifically, when the image processing unit 28 calculates various correction coefficients, such as the correction matrix, the white-balance correction coefficient, and the gamma value described above, the receiving device 27 stores these various correction coefficients in the storage medium 5. The storage medium 5 storing these various correction coefficients is inserted in the card I/F 4c. The control unit 44e takes in various correction coefficients from the storage medium 5 inserted in the card I/F 4c and controls the output I/F 44f so that it transmits these various correction coefficients to the control unit 43 of the capsule endoscope 42. Other than this function, the control unit 44e has similar functions to those of the control unit 4e of the image display device 4 described above.

The white plate 46 is disposed in the field of view to be captured of the imaging unit 9 and reflects each of the color lights emitted from the light-emitting units 8a to 8c to the imaging unit 9. On a light reflection surface of the white plate 46, the white chart 7d described above is formed. The white plate 46 reflects red light, green light, and blue light emitted from the light-emitting units 8a to 8c to the imaging unit 9. When the light-emitting units 8a to 8c simultaneously emit lights, the white plate 46 reflects white light formed of these red light, green light, and blue light to the imaging unit 9.

Next, the operation of the capsule endoscope 42 is specifically described, which includes the operation of sequentially switching luminescent colors of the capsule endoscope 42 onto the white plate 46 to capture the chart images PR, PG, PB, and PW of the plural colors. As depicted in FIG. 23, in an incomplete state in which the casing 6 is not provided yet, the capsule endoscope 42 sequentially switches luminescent colors to the white plate 46 to sequentially capture the chart images PR, PG, PB, and PW of the plural colors.

Specifically, in the process of assembling the capsule endoscope 42, the white plate 46 is disposed in the field of view to be captured of the imaging unit 9 of the capsule endoscope 42 in the incomplete state. Also, the control unit 43 is connected to the external power supply 45 via a cable or the like, and is supplied with power from the external power supply 45. In this state, the electrode pads 47a and 47b are electrically connected together. With this, the light-emitting elements 48a and 48b of the light-emitting elements 48a to 48f are electrically connected to the external power supply 45 via the electrode pads 47a and 47b and the control unit 43. The control unit 43 controls the light-emitting elements 48a and 48b so that these elements emit red light to the white plate 46, and also controls the imaging unit 9 so that it receives red light reflected from the white chart 7d of the white plate 46 to capture the chart image PR for each frame. The chart image PR for each frame captured by the imaging unit 9 based on the control of the control unit 43 is wirelessly transmitted by the communicating unit 10 to the receiving device 27.

Next, after the connection between the electrode pads 47a and 47b is released, the electrode pads 47c and 47d are electrically connected together. With this, the light-emitting elements 48c and 48d of the light-emitting elements 48a to 48f are electrically connected to the external power supply 45 via the electrode pads 47c and 47d and the control unit 43. The control unit 43 controls the light-emitting elements 48c and 48d so that these elements emit green light to the white plate 46, and also controls the imaging unit 9 so that it receives green light reflected from the white chart 7d of the white plate 46 to capture the chart image PG for each frame. The chart image PG for each frame captured by the imaging unit 9 based on the control of the control unit 43 is wirelessly transmitted by the communicating unit 10 to the receiving device 27.

Subsequently, after the connection between the electrode pads 47c and 47d is released, the electrode pads 47e and 47f are electrically connected together. With this, the light-emitting elements 48e and 48f of the light-emitting elements 48a to 48f are electrically connected to the external power supply 45 via the electrode pads 47e and 47f and the control unit 43. The control unit 43 controls the light-emitting elements 48e and 48f so that these elements emit blue light to the white plate 46, and also controls the imaging unit 9 so that it receives blue light reflected from the white chart 7d of the white plate 46 to capture the chart image PB for each frame. The chart image PB for each frame captured by the imaging unit 9 based on the control of the control unit 43 is wirelessly transmitted by the communicating unit 10 to the receiving device 27.

Next, the plural electrode pads 47a to 47f are electrically connected together. With this, the light-emitting elements 48a to 48f are electrically connected to the external power supply 45 via the electrode pads 47a to 47f and the control unit 43. The control unit 43 controls the light-emitting elements 48a to 48f so that these elements approximately simultaneously emit red light, green light, and blue light to the white plate 46, and also controls the imaging unit 9 so that it receives white light (white light formed by combination of red light, green light, and blue light) reflected from the white chart 7d of the white plate 46 to capture the chart image PW for each frame. The chart image PW for each frame captured by the imaging unit 9 based on the control of the control unit 43 is wirelessly transmitted by the communicating unit 10 to the receiving device 27.

In this manner, the capsule endoscope 42 in the incomplete state sequentially acquires the chart images PR, PG, PB, and PW for each frame unit, and sequentially and wirelessly transmits each piece of chart image information about the chart images PR, PG, PB, and PW for each frame to the receiving device 27. Note that the switching order of luminescent colors of the capsule endoscope 42 in the incomplete state, that is, the connecting order of the electrode pads 47a to 47f, may be a desired connecting order as long as red light, green light, blue light, and white light can be emitted for one cycle or more in the desired order.

The image processing unit 28 of the receiving device 27 calculates various correction coefficients, such as the inverse matrix $M^{-1}$ of the color-mixture matrix M (the correction matrix), the light-receiving-amount output W in the non-color-mixture state (the white-balance correction coefficient), and the gamma value described above, based on each piece of chart image information about the chart images PR, PG, PB, and PW for each frame captured by the capsule endoscope 42 in the incomplete state. The receiving device 27 stores these various correction coefficients calculated by the image processing unit 28 in the storage medium 5. The image display device 44 acquires various correction coefficients via the storage medium 5, and transmits these various correction coefficients to the control unit 43.

The control unit 43 acquires various correction coefficients calculated by the image processing unit 28 described above via the image display device 44, and stores these various correction coefficients in its ROM. In this manner, when the control unit 43 acquires various correction coefficients, the external power supply 45 and the image display device 44 are released from the connection to the control unit 43. Then, as described above, the illumination substrate 8d in a state where the plural electrode pads 47a to 47f electrically connected to each other, the light-emitting units 8a to 8c, the imaging unit 9, the communicating unit 10, the power supply unit 12, and the control unit 43 are accommodated inside of the capsule casing 6. With this, the capsule endoscope 42 becomes in a complete-product state.

After starting power supply of the power supply unit 12 by an external magnetic force, the completed capsule endoscope 42 is inserted into an organ of the subject 100. The capsule endoscope 42 sequentially captures an in-vivo image of the subject 100 at predetermined intervals, and wirelessly transmits an image signal containing the in-vivo image and various correction coefficients to the receiving device 27. As a result, the image acquiring apparatus 41 according to the fourth embodiment can acquire the corrected in-vivo image.

As described in the foregoing, in the fourth embodiment of the present invention, as with the modification example of the third embodiment as described above, an image processing unit that calculates various correction coefficients regarding an in-vivo image is provided. A pair of electrode pads for switching conduction states of the plural light-emitting units that emit color lights of plural colors and a predetermined power supply unit (for example, the external power supply described above) is formed for each light-emitting unit. With the connection states of the electrode pads being sequentially switched, the luminescent colors with respect to the white chart are sequentially switched, and reflected light from the white chart is received to capture a chart image of plural colors for each frame. Also, various correction coefficients calculated by the image processing unit based on each piece of chart image information for each frame are saved in a storage unit on an imaging unit side (for example, capsule endoscope). Whenever the imaging unit captures a subject image, these in-vivo image and various correction coefficients are transmitted to the image processing unit, and the image processing unit corrects the in-vivo image together with the various correction coefficients. Therefore, even without providing a switch circuit or the like for switching luminescence colors on the imaging unit side, a chart image of the plural colors can be captured for each frame. Thus, operations and effects similar to those of the modification example of the third embodiment described above can be obtained, and also downsizing of the device size on the imaging unit side can be promoted.

Also, when the device on the imaging unit side is a capsule endoscope, downsizing of the capsule endoscope can be promoted. With this, a burden on the subject when the capsule endoscope is inserted into an organ can be reduced.

Modification Example of The Fourth Embodiment

Next, a modification example of the fourth embodiment of the present invention is described. In the fourth embodiment described above, color lights of plural colors are sequentially emitted to the white chart 7d of the white plate 46 to sequentially capture the chart images PR, PG, PB, and PW for each frame. In the modification example of the fourth embodiment, a color plate on which color charts of plural colors are formed on a light reflection surface is used, and white light is emitted to the color charts of the color plate to capture the chart images PR, PG, PB, and PW of the plural colors.

Figure 26:
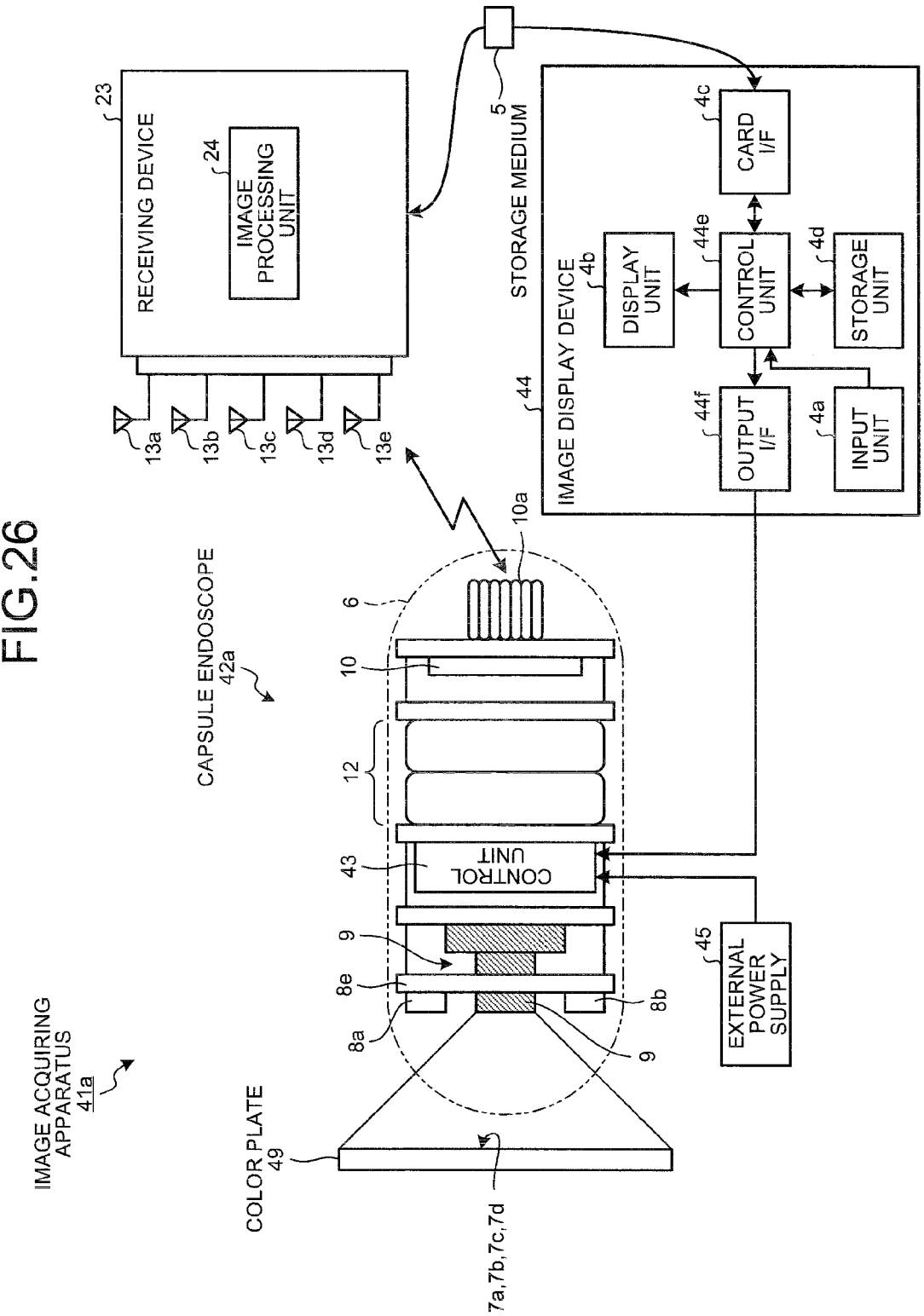
FIG. 26 is a schematic diagram depicting a configuration example of an observation apparatus according to a modification example of the fourth embodiment of the present invention.
Figure 27:
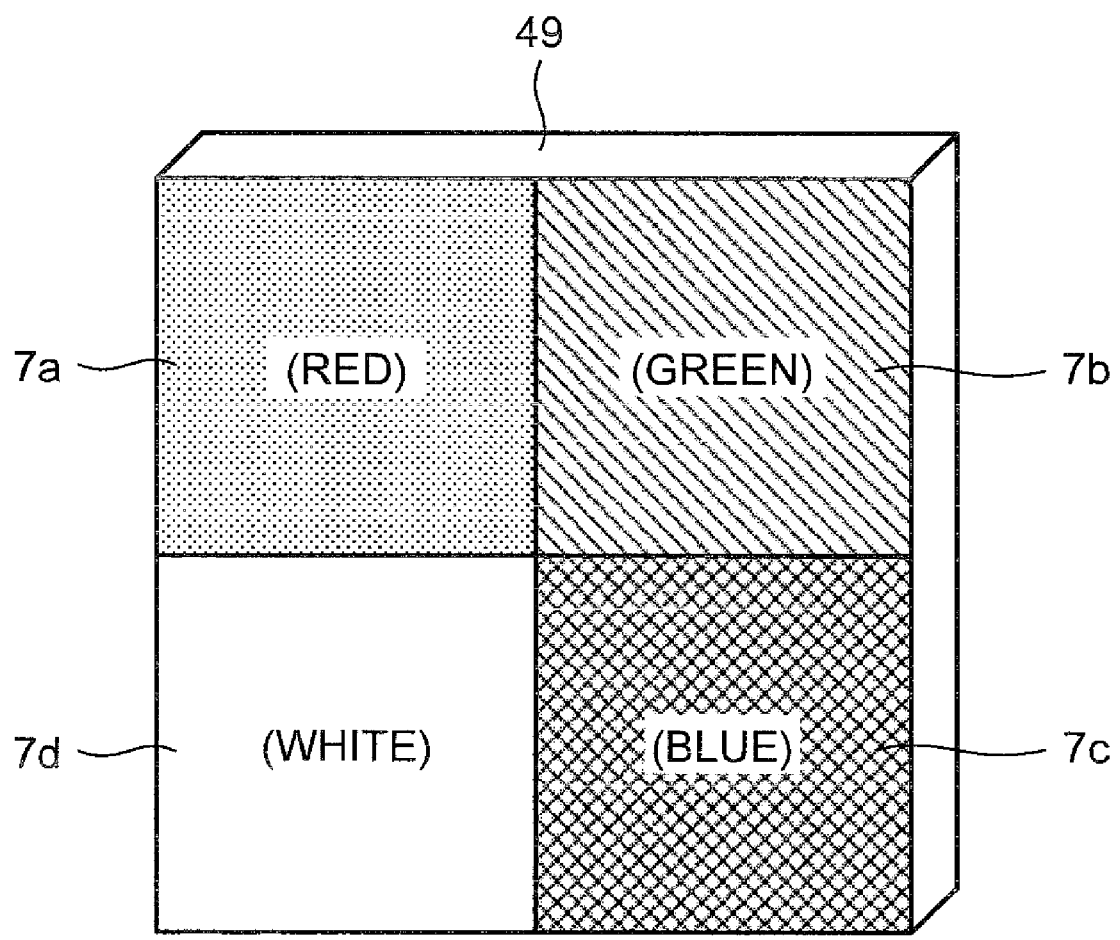
FIG. 27 is a schematic diagram depicting a configuration example of a color plate in which color charts of plural colors are formed on a reflection surface.

FIG. 26 is a schematic diagram depicting a configuration example of an observation apparatus according to the modification example of the fourth embodiment of the present invention. FIG. 27 is a schematic diagram depicting a configuration example of a color plate in which color charts of plural colors are formed on a reflection surface. As depicted in FIGS. 26 and 27, an image acquiring apparatus 41a, which is an observation apparatus according to the modification example of the fourth embodiment, has a capsule endoscope 42a in place of the capsule endoscope 42 of the image acquiring apparatus 41 according to the fourth embodiment described above, a receiving device 23 in place of the receiving device 27, and a color plate 49 in place of the white plate 46. Note that the receiving device 27 is a receiving device similar to that of the image acquiring apparatus 21 according to the second embodiment. Other configurations are the same as those of the fourth embodiment, and the same component units are denoted with the same reference numerals.

As exemplified by the capsule endoscope 42 of the fourth embodiment described above, the capsule endoscope 42a in an incomplete state captures the chart images PR, PG, PB, and PW of the plural colors. The capsule endoscope 42a has an illumination substrate 8e in place of the illumination substrate 8d of the capsule endoscope 42 of the fourth embodiment described above. As approximately similar to the illumination substrate 8d of the fourth embodiment described above, the illumination substrate 8e has the light-emitting elements 48a to 48f of the light-emitting units 8a to 8c mounted thereon, and an optical system of the imaging unit 9 is inserted in a through hole at a substrate center portion. On the illumination substrate 8e, a circuit is formed in a state where the plural electrode pads 47a to 47f as depicted in FIG. 25 have been already electrically connected. In an incomplete state, the capsule endoscope 42a that has the illumination substrate 8e consumes power from the external power supply 45 to emit white light to the color charts of the color plate 49, and receives reflected light from the color charts of the color plate 49 to capture the chart images PR, PG, PB, and PW of the plural colors.

The color plate 49 has, as depicted in FIG. 27, color charts of plural colors (the red chart 7a, the green chart 7b, the blue chart 7c, and the white chart 7d) on its reflection surface. As with the color charts of the plural colors formed on the inner wall surface of the cap 25 in the second embodiment described above, these red chart 7a, green chart 7b, blue chart 7c, and white chart 7d are formed on the reflection surface of the color plate 49 so as to each represent an approximately equal area, with the optical axis of the imaging unit 9 being taken as a center. The color plate 49 is disposed in the field of view to be captured of the imaging unit 9 and, when illuminated with white light based on simultaneous light emission of the light-emitting units 8a to 8c, reflects red light, green light, blue light, and white light correspondingly to the color charts of the plural colors to the imaging unit 9.

Here, when the reflection surface of the color plate 49 is illuminated based on simultaneous light emission of the light-emitting units 8a to 8c with white light (that is, white light formed of red light, green light, and blue light), the imaging unit 9 receives reflected light from the red chart 7a of the color charts of the plural colors formed on the reflection surface of the color plate 49 to capture the chart image PR, receives reflected light from the green chart 7b to capture the chart image PG, receives reflected light from the blue chart 7c to capture the chart image PB, and receives reflected light from the white chart 7d to capture the chart image PW. In this case, as with the case of the second embodiment described above, the imaging unit 9 captures a chart image in which the chart images PR, PG, PB, and PW of the plural colors are included in one frame.

The capsule endoscope 42a wirelessly transmits the chart images of one frame captured by the imaging unit 9 to the receiving device 23. As indicated in the second embodiment described above, the image processing unit 24 of the receiving device 23 calculates various correction coefficients, such as the correction matrix and the white-balance correction coefficient, based on the chart image information about the plural colors included in the chart images of one frame. The receiving device 23 saves these various correction coefficients calculated by the image processing unit 24 in the storage medium 5.

As with the fourth embodiment described above, these various correction coefficients saved in the storage medium 5 are acquired by the control unit 43 of the capsule endoscope 42a via the image display device 44. Then, as with the image acquiring apparatus 41 according to the fourth embodiment described above, the image acquiring apparatus 41a according to the modification example of the fourth embodiment acquires an in-vivo image of the subject 100, corrects the in-vivo image based on the various correction coefficients, and acquires the corrected in-vivo image.

As described in the foregoing, in the modification example of the fourth embodiment of the present invention, white light is emitted to color charts of plural colors, and reflected lights from the color charts of the plural colors are received to simultaneously capture chart images of plural colors including white. Based on chart image information about the plural colors, various correction coefficients regarding the in-vivo image are calculated. Other configuration is similar to that of the fourth embodiment described above. Therefore, it is not required to provide any special circuit, electrode pads, or others for sequentially switching luminescent colors from the plural light-emitting units. With the color charts of the plural colors being illuminated with white light formed based on simultaneous light emission of the plural light-emitting units, the chart images of the plural colors can be simultaneously captured. As a result, operations and effects similar to those of the fourth embodiment described above can be obtained, and also downsizing of the device size can further be promoted.

Also, when the modification example of the fourth embodiment is applied to a capsule endoscope, downsizing of the capsule endoscope can further be promoted. With this, a burden on the subject when the capsule endoscope is inserted inside of an organ can further be reduced.

Fifth Embodiment

Next, a fifth embodiment of the present invention is described. In the fourth embodiment described above, each vector component of the light-receiving-amount output (light-receiving-amount value of each color component) of each unit pixel group forming an in-vivo image is divided by the white-balance correction coefficient to correct the white balance of the in-vivo image. In the fifth embodiment, the light-emitting amount of the plural light-emitting units is adjusted correspondingly to the white-balance correction coefficient, thereby correcting the white balance of the in-vivo image.

Figure 28:
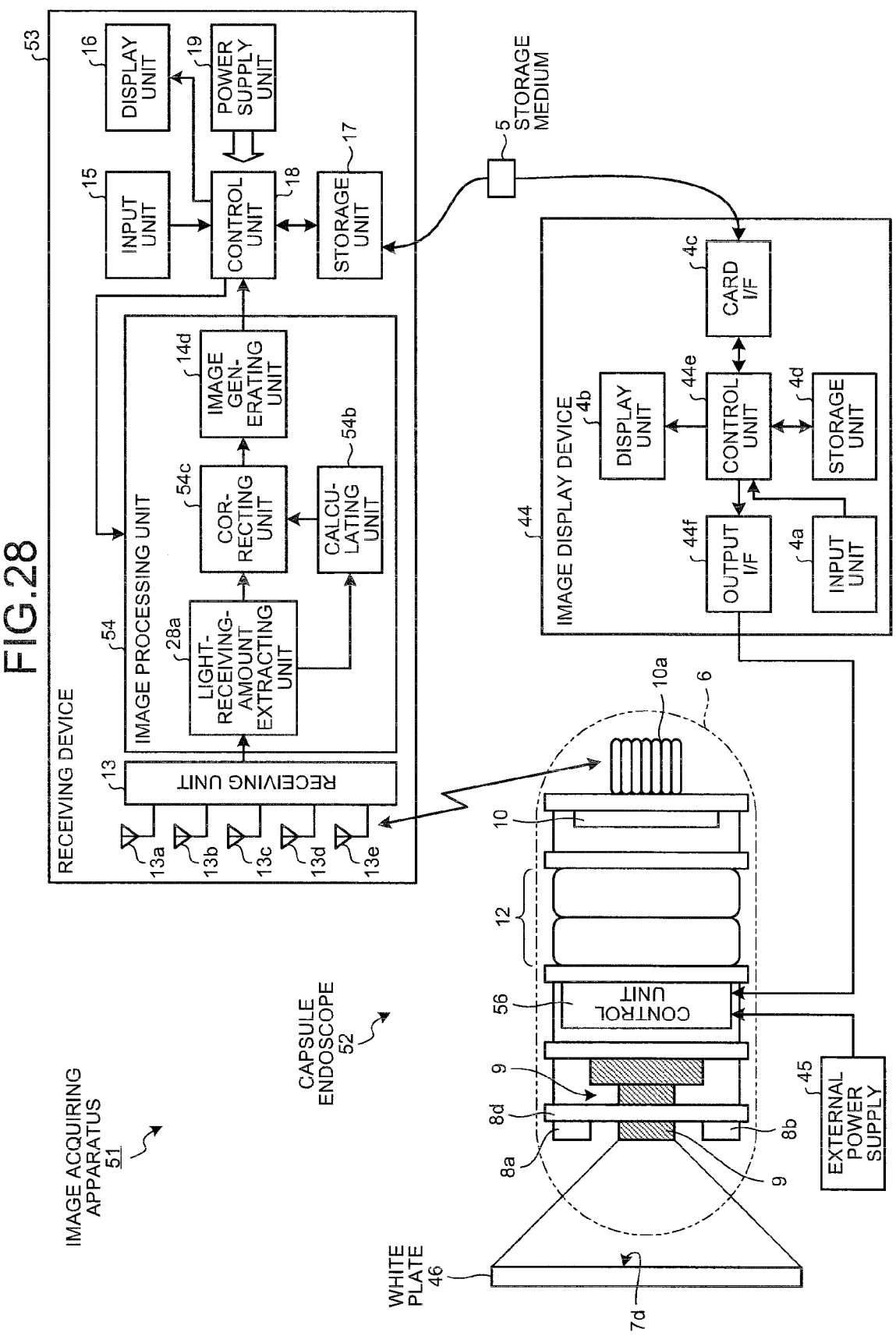
FIG. 28 is a block diagram schematically depicting a configuration example of an observation apparatus according to a fifth embodiment of the present invention.
Figure 29:
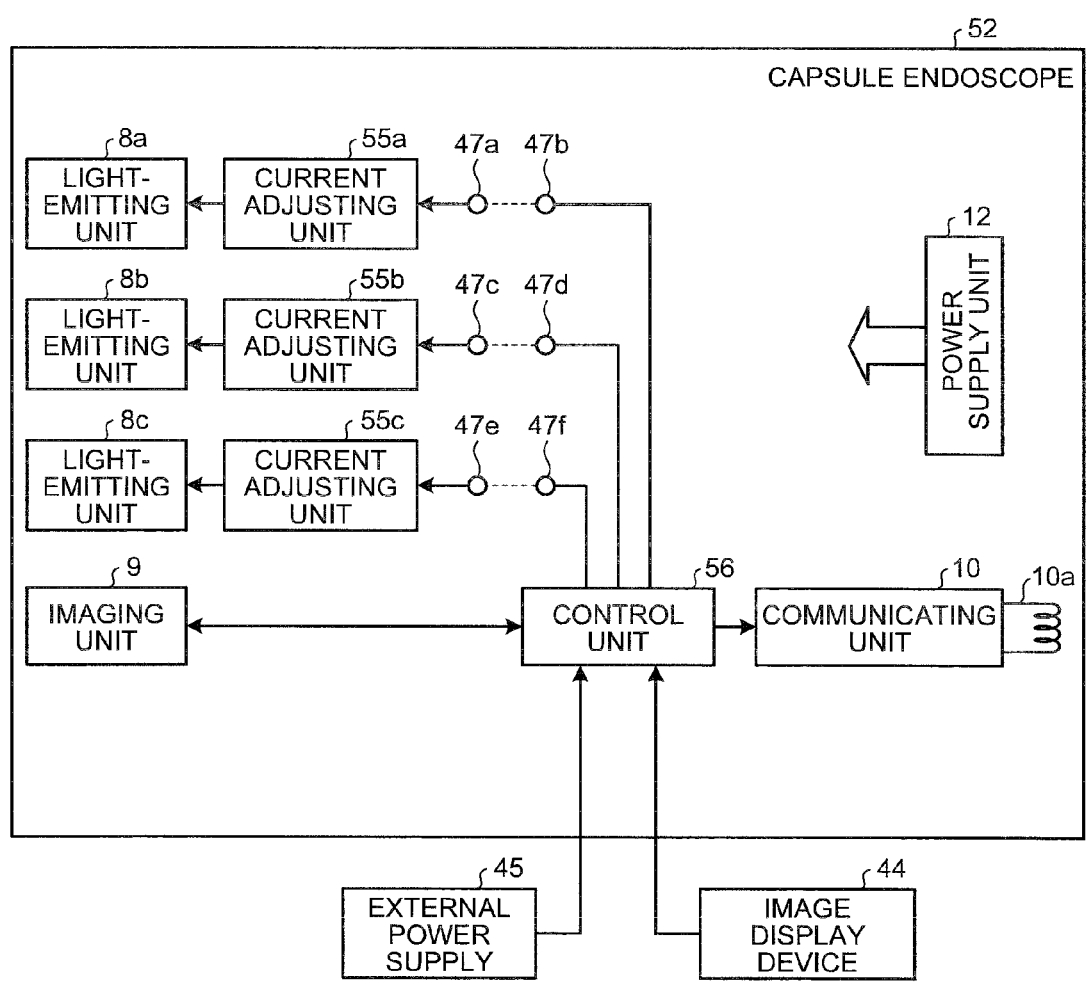
FIG. 29 is a block diagram schematically depicting a configuration example of a capsule endoscope of the observation apparatus according to the fifth embodiment.

FIG. 28 is a block diagram schematically depicting a configuration example of an observation apparatus according to the fifth embodiment of the present invention. FIG. 29 is a block diagram schematically depicting a configuration example of a capsule endoscope of the observation apparatus according to the fifth embodiment. As depicted in FIGS. 28 and 29, an image acquiring apparatus 51, which is an observation apparatus according to the fifth embodiment, has a capsule endoscope 52 in place of the capsule endoscope 42 of the image acquiring apparatus 41 according to the fourth embodiment described above, and a receiving device 53 in place of the receiving device 27. The capsule endoscope 52 has a control unit 56 in place of the control unit 43 of the capsule endoscope 42 of the fourth embodiment described above, and further has current adjusting units 55a to 55c that adjusts current values of the light-emitting units 8a to 8c, respectively. The receiving device 53 has an image processing unit 54 in place of the image processing unit 28 of the receiving device 27 of the fourth embodiment described above. Other configurations are the same as those of the fourth embodiment, and the same component units are provided with the same reference numerals.

The capsule endoscope 52 acquires each of the current values corresponding to the white-balance correction coefficient calculated by the image processing unit 54 of the receiving device 53 via the image display device 44 to adjust each of the light-emitting amounts of the plural light-emitting units 8a to 8c based on each of the current values. By adjusting each of the light-emitting amount of the light-emitting units 8a to 8c in this manner, the capsule endoscope 52 can capture an in-vivo image with the white balance corrected. The capsule endoscope 52 transmits an image signal containing the white-balance-corrected in-vivo image and various correction coefficients (various correction coefficients, such as the correction matrix and the gamma value, except the white-balance correction coefficient) to the receiving device 53. Other functions of the capsule endoscope 52 are similar to those of the capsule endoscope 42 of the fourth embodiment described above.

The current adjusting units 55a to 55c adjust the current value of power supplied to each of the light-emitting units 8a to 8c from the power supply unit 12. Specifically, based on the current value corresponding to the white-balance correction coefficient acquired from the control unit 56, the current adjusting unit 55a adjusts the current value of power supplied from the power supply unit 12 to the light-emitting unit 8a, thereby adjusting the light-emitting amount of red light emitted from the light-emitting unit 8a. Based on the current value corresponding to the white-balance correction coefficient acquired from the control unit 56, the current adjusting unit 55b adjusts the current value of power supplied from the power supply unit 12 to the light-emitting unit 8b, thereby adjusting the light-emitting amount of green light emitted from the light-emitting unit 8b. Based on the current value corresponding to the white-balance correction coefficient acquired from the control unit 56, the current adjusting unit 55c adjusts the current value of power supplied from the power supply unit 12 to the light-emitting unit 8c, thereby adjusting the light-emitting amount of blue light emitted from the light-emitting unit 8c.

The control unit 56 acquires each current value corresponding to the white-balance correction coefficient calculated by the image processing unit 54 of the receiving device 53 via the image display device 44. The control unit 56 transmits, to the current adjusting unit 55a, a current value for adjusting the light-emitting amount of red light within the current values, and controls the current adjusting unit 55a so that it adjusts the current value of power supplied from the power supply unit 12 to the light-emitting unit 8a to the transmitted current value. Also, the control unit 56 transmits, to the current adjusting unit 55b, a current value for adjusting the light-emitting amount of green light within the current values, and controls the current adjusting unit 55b so that it adjusts the current value of power supplied from the power supply unit 12 to the light-emitting unit 8b to the transmitted current value. Furthermore, the control unit 56 transmits, to the current adjusting unit 55c, a current value for adjusting the light-emitting amount of blue light within the current values, and controls the current adjusting unit 55c so that it adjusts the current value of power supplied from the power supply unit 12 to the light-emitting unit 8c to the transmitted current value.

Also, the control unit 56 generates an image signal containing the white-balance corrected in-vivo image captured by the imaging unit 9 and various correction coefficients acquired via the image display device 44 (such as the correction matrix and the gamma value), and controls the communicating unit 10 so that it wirelessly transmits the image signal to the receiving device 53. Other functions of the control unit 56 are similar to those of the control unit 43 of the capsule endoscope 42 of the fourth embodiment described above.

As with the image processing unit 28 of the receiving device 27 described above, the image processing unit 54 of the receiving device 53 acquires chart image information about the chart images PR, PG, PB, and PW for each frame via the receiving unit 13 and, based on the chart image information, calculates various correction coefficients, such as the correction matrix, the white-balance correction coefficient, and the gamma value. Then, based on the white-balance correction coefficient (each vector component of the light-receiving-amount output W described above), the image processing unit 54 calculates a current value of each of the light-emitting units 8a to 8c corresponding to the white-balance correction coefficient. Each of the current values of the light-emitting units 8a to 8c corresponding to the white-balance correction coefficient calculated by the image processing unit 54 and various correction coefficients (such as the correction matrix and the gamma value) are saved in the storage medium 5 inserted in the storage unit 17, and are acquired by the image display device 44 via the storage medium 5. Also, based on the in-vivo image information acquired from the capsule endoscope 52 via the receiving unit 13 and various correction coefficients (except the white-balance correction coefficient), the image processing unit 54 performs a color-mixture correcting process and a gamma correcting process on the white-balance-corrected in-vivo image captured by the imaging unit 9.

The image processing unit 54 has a calculating unit 54b in place of the calculating unit 14b of the image processing unit 28 of the receiving device 27, and a correcting unit 54c in place of the correcting unit 24c. Other configurations are the same as those of the image processing unit 28 of the receiving device 27 of the fourth embodiment described above.

As with the calculating unit 14b of the image processing unit 28 described above, based on each of piece of chart image information about the chart images PR, PG, PB, and PW for each frame acquired from the light-receiving-amount extracting unit 28a, the calculating unit 54b calculates the correction matrix (the inverse matrix $M^{-1}$ of the color-mixture matrix M), the white-balance correction coefficient (the light-receiving-amount output W in the non-color-mixture state), and the gamma value. Then, based on each vector component of the light-receiving-amount output W in the non-color-mixture state, the calculating unit 54b calculates each of the current values of the light-emitting units 8a to 8c corresponding to the white-balance correction coefficient. Each current value corresponding to the white-balance correction coefficient is a current value for obtaining each light-emitting amount of red light, green light, and blue light to be emitted by the light emitting units 8a to 8c to the object (the inside of the organ of the subject 100) so as to capture an in-vivo image in a white-balance-corrected state.

Note that each of the current values of the light-emitting units 8a to 8c corresponding to the white-balance correction coefficient calculated by the calculating unit 54b and various correction coefficients (such as the correction matrix and the gamma value) are saved in the storage medium 5 inserted in the storage unit 17, and is acquired by the image display device 44 via the storage medium 5.

The correcting unit 54c acquires the in-vivo image information wirelessly transmitted from the capsule endoscope 52 via the light-receiving-amount extracting unit 28a and various correction coefficients (except the white-balance correction coefficient). Here, the in-vivo image information acquired by the correcting unit 54c contains the light-receiving-amount output of each unit pixel group forming the white-balance-corrected in-vivo image captured by the imaging unit 9. The correcting unit 54c uses the white-balance-corrected in-vivo image and various correction coefficients to perform a color-mixture correcting process and a gamma correcting process on the white-balance-corrected in-vivo image. With this, a color-mixture correcting process, a white-balance correcting process, and a gamma correcting process on the in-vivo image are performed.

Next, the operation of the capsule endoscope 52 is described, which includes the operation of adjusting the light-emitting amount onto the object to capture a white-balance-corrected in-vivo image. As with the capsule endoscope 42 of the fourth embodiment described above, the capsule endoscope 52 captures the chart images PR, PG, PB, and PW for each frame, and sequentially and wirelessly transmits each piece of chart image information about the chart images PR, PG, PB, and PW for each frame to the receiving device 53.

In this state, the electrode pads 47a, 47c, and 47e and the electrode pads 47b, 47d, and 47f, depicted in FIG. 29, are electrically connected to each other, respectively. That is, the control unit 56 is in a connection state with the current adjusting unit 55a via a pair of the electrode pads 47a and 47b, is in a connection state with the current adjusting unit 55b via a pair of the electrode pads 47c and 47d, and is in a connection state with the current adjusting unit 55c via a pair of the electrode pads 47e and 47f. The control unit 56 acquires, via the image display device 44, each current value corresponding to the white-balance correction coefficient calculated by the calculating unit 54b described above and various correction coefficients, and stores each of these current values and various correction coefficients in its ROM.

When the control unit 56 acquires each current value corresponding to the white-balance correction coefficient and various correction coefficients in a manner as described above, as with the capsule endoscope 42 of the fourth embodiment described above, the capsule endoscope 52 is completed by having each component unit accommodated inside of the casing 6. The completed capsule endoscope 52 is inserted into an organ of the subject 100 to capture an in-vivo image of the subject.

Here, the current adjusting unit 55a adjusts the current value of power supplied from the power supply unit 12 to the light-emitting unit 8a to a current value acquired from the control unit 56 (a current value for adjusting the light-emitting amount of red light corresponding to the white-balance correction coefficient). The current adjusting unit 55b adjusts the current value of power supplied from the power supply unit 12 to the light-emitting unit 8b to a current value acquired from the control unit 56 (a current value for adjusting the light-emitting amount of green light corresponding to the white-balance correction coefficient). The current adjusting unit 55c adjusts the current value of power supplied from the power supply unit 12 to the light-emitting unit 8c to a current value acquired from the control unit 56 (a current value for adjusting the light-emitting amount of blue light corresponding to the white-balance correction coefficient).

The light-emitting units 8a to 8c with their current values adjusted by the current adjusting units 55a to 55c, respectively, simultaneously emit red light, green light, and blue light, respectively, with the light-emitting amount to be emitted to an object (the inside of the organ) for capturing an in-vivo image with the white balance being corrected. In this case, the imaging unit 9 captures an image of the inside of the organ illuminated with red light, green light, and blue light with their light-emitting amounts adjusted correspondingly to the white-balance correction coefficient, that is, a white-balance-corrected in-vivo image.

As described in the foregoing, in the fifth embodiment of the present invention, each of the current values of power supplied to the plural light-emitting units is adjusted correspondingly to the white-balance correction coefficient. For capturing an object image in a white-balance-corrected state, color lights of plural colors each with an adjusted light-emitting amount to be emitted to the object are simultaneously emitted. Other configuration is similar to that of the fourth embodiment described above. Therefore, operations and effects similar to those of the fourth embodiment described above can be obtained. Also, the light-receiving sensitivity (resolution) of the imaging unit can be effectively used, and also the white-balance-corrected object image can be easily captured.

Also, when the observation apparatus (image acquiring apparatus) according to the fifth embodiment is applied to a capsule endoscope, an in-vivo image subjected to white-balance correction can be captured by the capsule endoscope, resulting in an increase in accuracy of analyzing the inside of the organ of the subject.

First Modification Example of The Fifth Embodiment

Next, a first modification example of the fifth embodiment of the present invention is described. In the fifth embodiment described above, each of the current values of power supplied to the light-emitting units 8a to 8c are adjusted to adjust each of the light-emitting amounts of the light-emitting units 8a to 8c. In the first modification example of the fifth embodiment, a resistance value of each of the circuits supplying power to the light-emitting units 8a to 8c is adjusted to adjust each of the light-emitting amounts of the light-emitting units 8a to 8c, thereby correcting the white balance of the in-vivo image.

Figure 30:
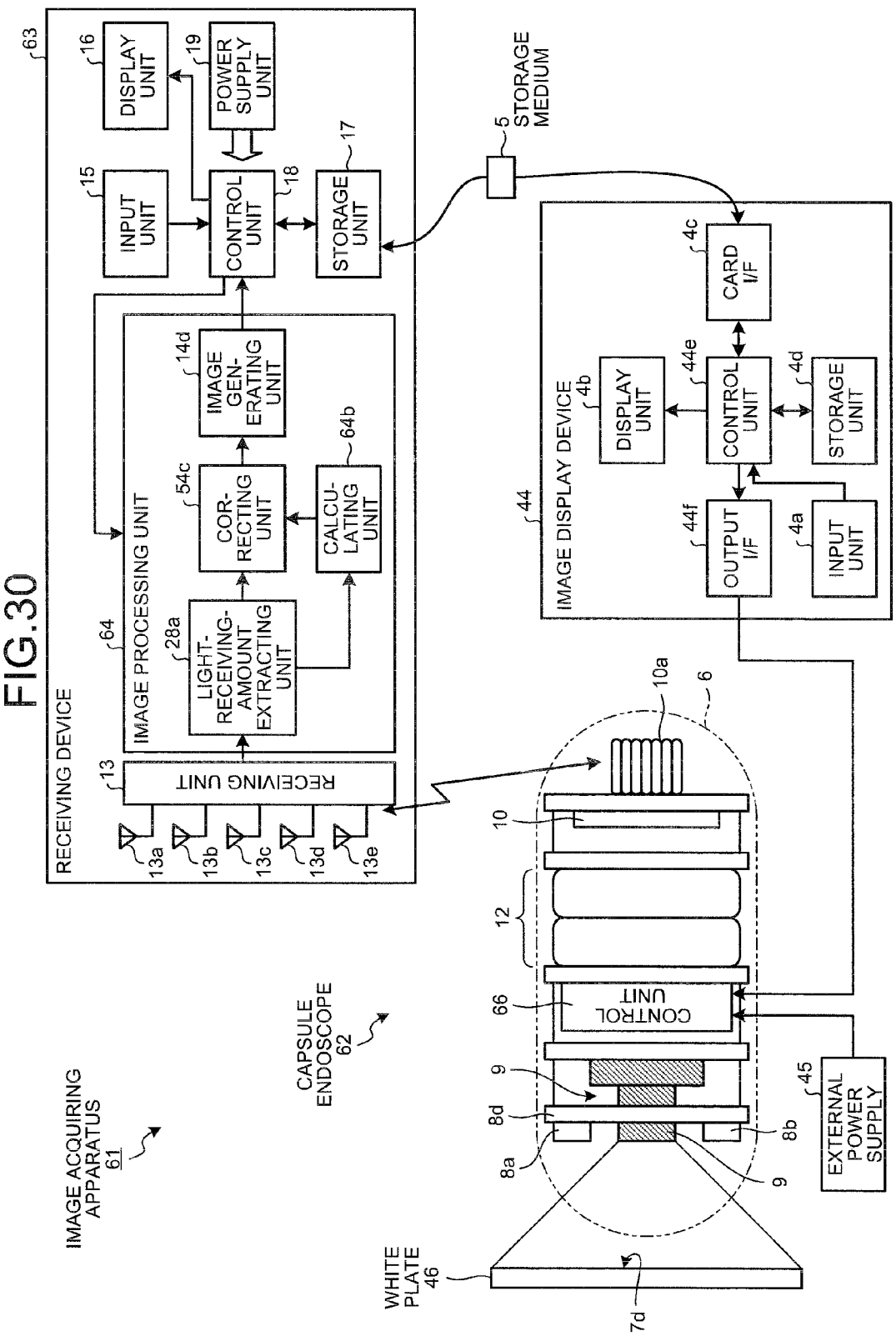
FIG. 30 is a block diagram schematically depicting a configuration example of an observation apparatus according to a first modification example of the fifth embodiment of the present invention.
Figure 31:
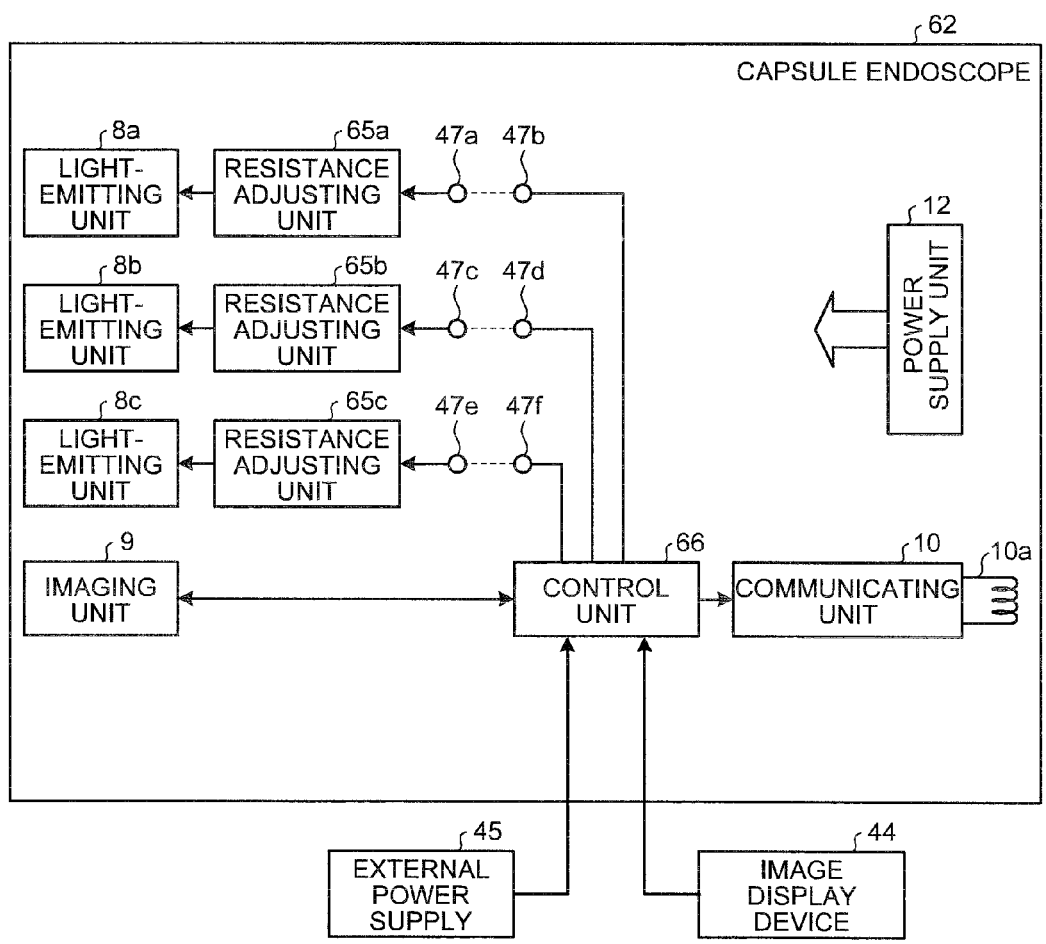
FIG. 31 is a block diagram schematically depicting a configuration example of a capsule endoscope of the observation apparatus according to the first modification example of the fifth embodiment.

FIG. 30 is a block diagram schematically depicting a configuration example of an observation apparatus according to the first modification example of the fifth embodiment of the present invention. FIG. 31 is a block diagram schematically depicting a configuration example of a capsule endoscope of the observation apparatus according to the first modification example of the fifth embodiment. As depicted in FIGS. 30 and 31, an image acquiring apparatus 61, which is an observation apparatus according to the first modification example of the fifth embodiment, has a capsule endoscope 62 in place of the capsule endoscope 52 of the image acquiring apparatus 51 according to the fifth embodiment described above, and a receiving device 63 in place of the receiving device 53. The capsule endoscope 62 has resistance adjusting units 65a to 65c in place of the current adjusting units 55a to 55c of the capsule endoscope 52 of the fifth embodiment described above, and has a control unit 66 in place of the control unit 56. The receiving device 63 has an image processing unit 64 in place of the image processing unit 54 of the receiving device 53 of the fifth embodiment described above. Other configurations are the same as those of the fifth embodiment, and the same component units are provided with the same reference numerals.

The capsule endoscope 62 acquires, via the image display device 44, each resistance value corresponding to the white-balance correction coefficient calculated by the image processing unit 64 of the receiving device 63, and adjusts each of the light-emitting amounts of the plural light-emitting units 8a to 8c based on each resistance the light-emitting units 8a to 8c in a manner as described above, the capsule endoscope 62 can capture a white-balance-corrected in-vivo image. Other functions of the capsule endoscope 62 are similar to those of the capsule endoscope 52 of the fifth embodiment described above.

The resistance adjusting units 65a to 65c adjust the resistant value of each of the circuits supplying power from the power supply unit 12 to the light-emitting units 8a to 8c. Specifically, the resistance adjusting units 65a to 65c are each constructed by using a variable resistor or the like. Based on the resistance value corresponding to the white-balance correction coefficient acquired from the control unit 66, the resistance adjusting unit 65a adjusts the resistance value of the circuit supplying power from the power supply unit 12 to the light-emitting unit 8a, thereby adjusting the light-emitting amount of red light emitted from the light-emitting unit 8a. Based on the resistance value corresponding to the white-balance correction coefficient acquired from the control unit 66, the resistance adjusting unit 65b adjusts the resistance value of the circuit supplying power from the power supply unit 12 to the light-emitting unit 8b, thereby adjusting the light-emitting amount of green light emitted from the light-emitting unit 8b. Based on the resistance value corresponding to the white-balance correction coefficient acquired from the control unit 66, the resistance adjusting unit 65c adjusts the resistance value of the circuit supplying power from the power supply unit 12 to the light-emitting unit 8c, thereby adjusting the light-emitting amount of blue light emitted from the light-emitting unit 8c.

The control unit 66 acquires each resistance value corresponding to the white-balance correction coefficient calculated by the image processing unit 64 of the receiving device 63 via the image display device 44. The control unit 66 transmits, to the resistance adjusting unit 65a, a resistance value for adjusting the light-emitting amount of red light among the resistance values, and controls the resistance adjusting unit 65a so that it adjusts the resistance value of the circuit supplying from the power supply unit 12 to the light-emitting unit 8a to the transmitted resistance value.

Also, the control unit 66 transmits, to the resistance adjusting unit 65b, a resistance value for adjusting the light-emitting amount of green light among the resistance values, and controls the resistance adjusting unit 65b so that it adjusts the resistance value of the circuit supplying from the power supply unit 12 to the light-emitting unit 8b to the transmitted resistance value. Furthermore, the control unit 66 transmits, to the resistance adjusting unit 65c, a resistance value for adjusting the light-emitting amount of blue light among the resistance values, and controls the resistance adjusting unit 65c so that it adjusts the resistance value of the circuit supplying from the power supply unit 12 to the light-emitting unit 8c to the transmitted resistance value. Other functions of the control unit 66 are similar to those of the control unit 56 of the capsule endoscope 52 of the fifth embodiment described above.

As with the image processing unit 54 of the receiving device 53 described above, the image processing unit 64 of the receiving device 63 acquires each piece of chart image information about the chart images PR, PG, PB, and PW for each frame via the receiving unit 13 and, based on the chart image information, calculates various correction coefficients, such as the correction matrix, the white-balance correction coefficient, and the gamma value. Then, based on the white-balance correction coefficient (each vector component of the light-receiving-amount output W described above), the image processing unit 64 calculates resistance values of the light-emitting units 8a to 8c corresponding to the white-balance correction coefficient. Each of the resistance values of the light-emitting units 8a to 8c corresponding to the white-balance correction coefficient calculated by the image processing unit 64 and various correction coefficients (such as the correction matrix and the gamma value) are saved in the storage medium 5 inserted in the storage unit 17, and are acquired by the image acquiring apparatus 44 via the storage medium 5. Other functions of the image processing unit 64 are similar to those of the image processing unit 54 of the receiving device 53 described above.

The image processing unit 64 has a calculating unit 64b in place of the calculating unit 54b of the image processing unit 54 of the receiving device 53 described above. Other configuration is similar to that of the image processing unit 54 of the receiving device 53 of the fifth embodiment described above.

As with the calculating unit 54b of the image processing unit 54 described above, based on each piece of the chart image information about the chart images PR, PG, PB, and PW for each frame acquired from the light-receiving-amount extracting unit 28a, the calculating unit 64b calculates the correction matrix (the inverse matrix $M^{-1}$ of the color-mixture matrix M), the white-balance correction coefficient (the light-receiving-amount output W in the non-color-mixture state), and the gamma value. Then, based on each vector component of the light-receiving-amount output W in the non-color-mixture state, the calculating unit 64b calculates each of the resistance values of the light-emitting units 8a to 8c corresponding to the white-balance correction coefficient. Each resistance value corresponding to the white-balance correction coefficient is a resistance value for obtaining each light-emitting amount of red light, green light, and blue light to be emitted by the light-emitting units 8a to 8c to the object (the inside of the organ of the subject 100) so as to capture an in-vivo image in a white-balance-corrected state.

Note that, as with the case of the fifth embodiment described above, each of the resistance values of the light-emitting units 8a to 8c corresponding to the white-balance correction coefficient calculated by the calculating unit 64b and various correction coefficients (such as the correction matrix and the gamma value) are saved in the storage medium 5 inserted in the storage unit 17, and are acquired by the image display device 44 via the storage medium 5.

Next, the operation of the capsule endoscope 62 is described, which includes the operation of adjusting the light-emitting amount onto the object to capture a white-balance-corrected in-vivo image. As with the capsule endoscope 52 of the fifth embodiment described above, the capsule endoscope 62 captures the chart images PR, PG, PB, and PW for each frame, and sequentially and wirelessly transmits each piece of chart image information about the chart images PR, PG, PB, and PW for each frame to the receiving device 63.

In this state, the electrode pads 47a, 47c, and 47e and the electrode pads 47b, 47d, and 47f, respectively, depicted in FIG. 31 are electrically connected to each other. That is, the control unit 66 is in a connection state with the resistance adjusting unit 65a via a pair of the electrode pads 47a and 47b, is in a connection state with the resistance adjusting unit 65b via a pair of the electrode pads 47c and 47d, and is in a connection state with the resistance adjusting unit 65c via a pair of the electrode pads 47e and 47f. The control unit 66 acquires, via the image display device 44, each resistance value corresponding to the white-balance correction coefficient calculated by the calculating unit 64b described above and various correction coefficients, and stores each of these resistance values and various correction coefficients in its ROM.

When the control unit 66 acquires each resistance value corresponding to the white-balance correction coefficient and various correction coefficients in a manner as described above, as with the capsule endoscope 52 of the fifth embodiment described above, the capsule endoscope 62 completed hv having each component unit accommodated inside of the casing 6. The completed capsule endoscope 62 is inserted inside of an organ of the subject 100 to capture an in-vivo image of the subject.

Here, the resistance adjusting unit 65a adjusts the resistance value of the circuit supplying power from the power supply unit 12 to the light-emitting unit 8a to a resistance value acquired from the control unit 66 (a resistance value for adjusting the light-emitting amount of red light corresponding to the white-balance correction coefficient). The resistance adjusting unit 65b adjusts the resistance value of the circuit supplying power from the power supply unit 12 to the light-emitting unit 8b to a resistance value acquired from the control unit 66 (a resistance value for adjusting the light-emitting amount of green light corresponding to the white-balance correction coefficient). The resistance adjusting unit 65c adjusts the resistance value of the circuit supplying power from the power supply unit 12 to the light-emitting unit 8c to a resistance value acquired from the control unit 66 (a resistance value for adjusting the light-emitting amount of blue light corresponding to the white-balance correction coefficient).

The light-emitting units 8a to 8c with their resistance values adjusted by the resistance adjusting units 65a to 65c, respectively, simultaneously emit red light, green light, and blue light, respectively, with the light-emitting amount to be emitted to an object (the inside of the organ) for capturing an in-vivo image with the white balance being corrected. In this case, the imaging unit 9 captures an image of the inside of the organ illuminated with red light, green light, and blue light with their light-emitting amounts adjusted correspondingly to the white-balance correction coefficient, that is, a white-balance-corrected in-vivo image.

As described in the foregoing, in the first modification example of the fifth embodiment of the present invention, each of the resistance values of the circuits supplying power to the plural light-emitting units is adjusted correspondingly to the white-balance correction coefficient. For capturing an object image in a white-balance-corrected state, color lights of plural colors each with an adjusted light-emitting amount to be emitted to the object are simultaneously emitted. Other configuration is similar to that of the fifth embodiment described above. Therefore, operations and effects similar to those of the fifth embodiment described above can be obtained.

Second Modification Example of The Fifth Embodiment

Next, a second modification example of the fifth embodiment of the present invention is described. In the fifth embodiment described above, each of the current values of power supplied to the light-emitting units 8a to 8c are adjusted to adjust each of the light-emitting amounts of the light-emitting units 8a to 8c. In the second modification example of the fifth embodiment, a light-emitting time of each of the light-emitting units 8a to 8c is adjusted to adjust each of the light-emitting amounts of the light-emitting units 8a to 8c, thereby correcting the white balance of the in-vivo image.

Figure 32:
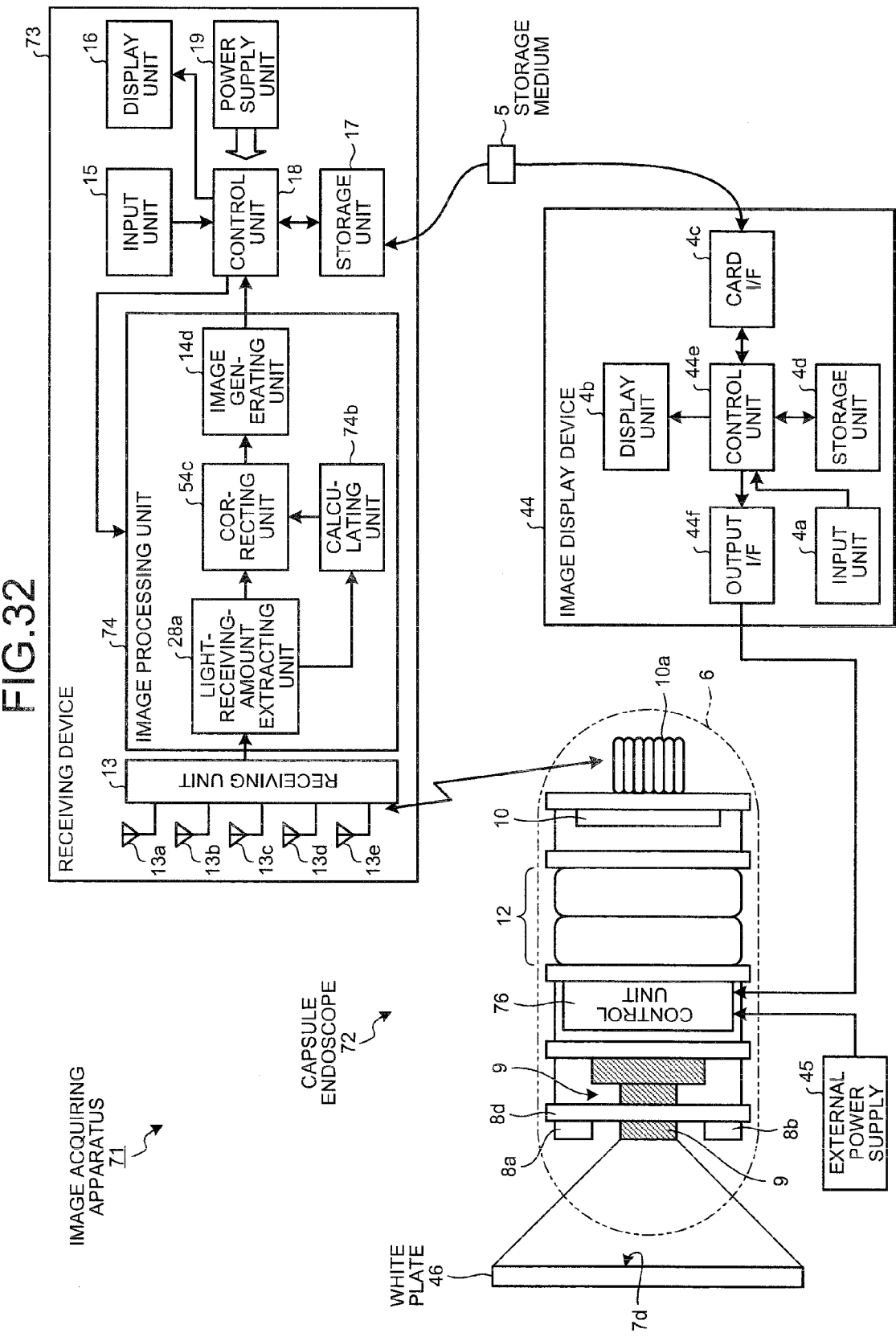
FIG. 32 is a block diagram schematically depicting a configuration example of an observation apparatus according to a second modification example of the fifth embodiment of the present invention.
Figure 33:
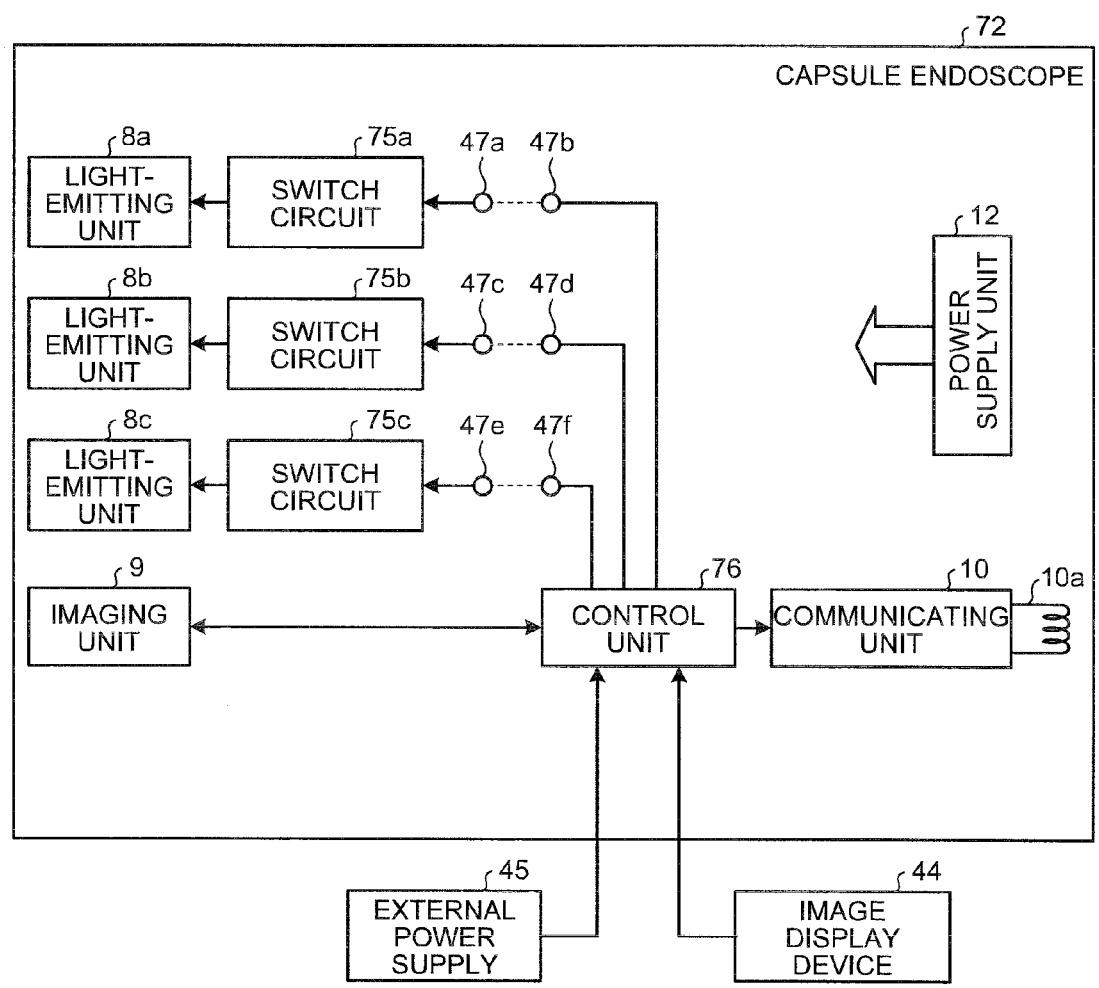
FIG. 33 is a block diagram schematically depicting a configuration example of a capsule endoscope of the observation apparatus according to the second modification example of the fifth embodiment.

FIG. 32 is a block diagram schematically depicting a configuration example of an observation apparatus according to the second modification example of the fifth embodiment of the present invention. FIG. 33 is a block diagram schematically depicting a configuration example of a capsule endoscope of the observation apparatus according to the second modification example of the fifth embodiment. As depicted in FIGS. 32 and 33, an image acquiring apparatus 71, which is an observation apparatus according to the second modification example of the fifth embodiment has a capsule endoscope 72 in place of the capsule endoscope 52 of the image acquiring apparatus 51 according to the fifth embodiment described above, and a receiving device 73 in place of the receiving device 53. The capsule endoscope 72 has switch circuits 75a to 75c for adjusting a light-emitting time in place of the current adjusting units 55a to 55c of the capsule endoscope 52 of the fifth embodiment described above, and has a control unit 76 in place of the control unit 56. The receiving device 73 has an image processing unit 74 in place of the image processing unit 54 of the receiving device 53 of the fifth embodiment described above. Other configurations are the same as those of the fifth embodiment, and the same component units are provided with the same reference numerals.

The capsule endoscope 72 acquires, via the image display device 44, each light-emitting time corresponding to the white-balance correction coefficient calculated by the image processing unit 74 of the receiving device 73, and adjusts each of the light-emitting amounts of the plural light-emitting units 8a to 8c based on each light-emitting time. By adjusting each of the light-emitting amounts of the light-emitting units 8a to 8c in a manner as described above, the capsule endoscope 72 can capture a white-balance-corrected in-vivo image. Other functions of the capsule endoscope 72 are similar to those of the capsule endoscope 52 of the fifth embodiment described above.

The switch circuits 75a to 75c adjust the light-emitting amount of each of the light-emitting units 8a to 8c by switching an ON/OFF state of the circuits supplying power from the power supply unit 12 to the light-emitting units 8a to 8c. Specifically, based on the control of the control unit 76, the switch circuit 75a switches an ON/Off state of the circuit supplying power from the power supply unit 12 to the light-emitting unit 8a, thereby adjusting the light-emitting time of the light-emitting unit 8a to adjust the light-emitting amount of red light emitted from the light-emitting unit 8a. Based on the control of the control unit 76, the switch circuit 75b switches an ON/Off state of the circuit supplying power from the power supply unit 12 to the light-emitting unit 8b, thereby adjusting the light-emitting time of the light-emitting unit 8b to adjust the light-emitting amount of green light emitted from the light-emitting unit 8b. Based on the control of the control unit 76, the switch circuit 75c switches an ON/Off state of the circuit supplying power from the power supply unit 12 to the light-emitting unit 8c, thereby adjusting the light-emitting time of the light-emitting unit 8c to adjust the light-emitting amount of blue light emitted from the light-emitting unit 8c.

The control unit 76 acquires, via the image display device 44, each light-emitting time corresponding to the white-balance correction coefficient calculated by the image processing unit 74 of the receiving device 73. The control unit 76 controls the switch circuit 75a so that the power-supply circuit is closed (in an ON state) for the light-emitting time for adjusting the light-emitting amount of red light among the light-emitting times. In this case, the control unit 76 controls the light-emitting time of the light-emitting unit 8a based on the control over the switch circuit 75a, thereby controlling the light-emitting amount of red light emitted from the light-emitting unit 8a. Also, the control unit 76 controls the switch circuit 75b so that the power-supply circuit is closed for the light-emitting time for adjusting the light-emitting amount of green light among the light-emitting times. In this case, the control unit 76 controls the light-emitting time of the light-emitting unit 8b based on the control over the switch circuit 75b, thereby controlling the light-emitting amount of green light emitted from the light-emitting unit 8b. Furthermore, the control unit 76 controls the switch circuit 75c so that the power-supply circuit is closed for the light-emitting time for adjusting the light-emitting amount of blue light among the light-emitting times. In this case, the control unit 76 controls the light-emitting time of the light-emitting unit 8c based on the control over the switch circuit 75c, thereby controlling the light-emitting amount of blue light emitted from the light-emitting unit 8c. Other functions of the control unit 76 are similar to those of the control unit 56 of the capsule endoscope 52 of the fifth embodiment described above.

As with the image processing unit 54 of the receiving device 53 described above, the image processing unit 74 of the receiving device 73 acquires each piece of chart image information about the chart images PR, PG, PB, and PW for each frame via the receiving unit 13 and, based on the chart image information, calculates various correction coefficients, such as the correction matrix, the white-balance correction coefficient, and the gamma value. Then, based on the white-balance correction coefficient (each vector component of the light-receiving-amount output W described above), the image processing unit 74 calculates light-emitting times of the light-emitting units 8a to 8c corresponding to the white-balance correction coefficient. Each of the light-emitting times of the light-emitting units 8a to 8c corresponding to the white-balance correction coefficient calculated by the image processing unit 74 and various correction coefficients (such as the correction matrix and the gamma value) are saved in the storage medium 5 inserted in the storage unit 17, and are acquired by the image display device 44 via the storage medium 5. Other functions of the image processing unit 74 are similar to those of the image processing unit 54 of the receiving device 53 described above.

The image processing unit 74 has a calculating unit 74b in place of the calculating unit 54b of the image processing unit 54 of the receiving device 53 described above. Other configuration is similar to that of the image processing unit 54 of the receiving device 53 of the fifth embodiment.

As with the calculating unit 54b of the image processing unit 54 described above, based on each piece of the chart image information about the chart images PR, PG, PB, and PW for each frame acquired from the light-receiving-amount extracting unit 28a, the calculating unit 74b calculates the correction matrix (the inverse matrix $M^{-1}$ of the color-mixture matrix M), the white-balance correction coefficient (the light-receiving-amount output W in the non-color-mixture state), and the gamma value. Then, based on each vector component of the light-receiving-amount output W in the non-color-mixture state, the calculating unit 74b calculates each of the light-emitting times of the light-emitting units 8a to 8c corresponding to the white-balance correction coefficient. Each light-emitting time corresponding to the white-balance correction coefficient is a light-emitting time for obtaining each light-emitting amount of red light, green light, and blue light to be emitted by the light-emitting units 8a to 8c to the object (the inside of the organ of the subject 100) so as to capture an in-vivo image in a white-balance-corrected state.

Note that, as with the case of the fifth embodiment described above, each of the light-emitting times of the light-emitting units 8a to 8c corresponding to the white-balance correction coefficient calculated by the calculating unit 74b and various correction coefficients (such as the correction matrix and the gamma value) are saved in the storage medium 5 inserted in the storage unit 17, and are acquired by the image display device 44 via the storage medium 5.

Next, the operation of the capsule endoscope 72 is described, which includes the operation of adjusting the light-emitting amount onto the object to capture a white-balance-corrected in-vivo image. As with the capsule endoscope 52 of the fifth embodiment described above, the capsule endoscope 72 captures the chart images PR, PG, PB, and PW for each frame, and sequentially and wirelessly transmits each piece of chart image information about the chart images PR, PG, PB, and PW for each frame to the receiving device 73.

In this state, the electrode pads 47a, 47c, and 47e and the electrode pads 47b, 47d, and 47f, respectively, depicted in FIG. 33 are electrically connected to each other. That is, the control unit 76 is in a connection state with the switch circuit 75a via a pair of the electrode pads 47a and 47b, is in a connection state with the switch circuit 75b via a pair of the electrode pads 47c and 47d, and is in a connection state with the switch circuit 75c via a pair of the electrode pads 47e and 47f. The control unit 76 acquires, via the image display device 44, each light-emitting time corresponding to the white-balance correction coefficient calculated by the calculating unit 74b described above and various correction coefficients; and stores each of these light-emitting times and various correction coefficients in its ROM.

When the control unit 76 acquires each light-emitting time corresponding to the white-balance correction coefficient and various correction coefficients in a manner as described above, as with the capsule endoscope 52 of the fifth embodiment described above, the capsule endoscope 72 is completed by having each component unit accommodated inside of the casing 6. The completed capsule endoscope 72 is inserted inside of an organ of the subject 100 to capture an in-vivo image of the subject.

Here, the control unit 76 controls the switch circuit 75a so that the circuit closes for the light-emitting time of red light among the light-emitting times corresponding to the white-balance correction coefficient, controls the switch circuit 75b so that the circuit closes for the light-emitting time of green light, and controls the switch circuit 75c so that the circuit closes for the light-emitting time of blue light. Based on the control of the control unit 76, the switch circuit 75a causes the circuit to be in an ON state for the light-emitting time of red light, the switch circuit 75b causes the circuit to be in an ON state for the light-emitting time of green light, and the switch circuit 75c causes the circuit to be in an ON state for the light-emitting time of blue light. With such a switching operation of the switch circuits 75a to 75c, each of the light-emitting times of the light-emitting units 8a to 8c is adjusted to each light-emitting time corresponding to the white-balance correction coefficient.

The light-emitting units 8a to 8c with their light-emitting times adjusted simultaneously emit red light, green light, and blue light, respectively, with the light-emitting amount to be emitted to an object (the inside of the organ) for capturing an in-vivo image with the white balance being corrected. In this case, the imaging unit 9 captures an image of the inside of the organ illuminated with red light, green light, and blue light with their light-emitting amounts adjusted correspondingly to the white-balance correction coefficient, that is, a white-balance-corrected in-vivo image.

As described in the foregoing, in the second modification example of the fifth embodiment of the present invention, each of the light-emitting times of the plural light-emitting units is adjusted correspondingly to the white-balance correction coefficient. For capturing an object image in a white-balance-corrected state, color lights of plural colors each with an adjusted light-emitting amount to be emitted to the object are simultaneously emitted. Other configuration is similar to that of the fifth embodiment described above. Therefore, operations and effects similar to those of the fifth embodiment described above can be obtained.

Sixth Embodiment

Next, a sixth embodiment of the present invention is described. In the modification example of the third embodiment described above, based on each piece of chart image information of the chart images PR, PG, PB, and PW, various correction coefficients are calculated, such as the inverse matrix $M^{-1}$ of the color-mixture matrix M (the correction matrix) and the light-receiving-amount output W in the non-color-mixture state (the white-balance correction coefficient). In the sixth embodiment, the inverse matrix $M^{-1}$ of the color-mixture matrix M is calculated based on the transmittance of each color light passing through color filters of plural colors formed on pixels of the imaging unit and, based on the inverse matrix $M^{-1}$ and the chart image information of the chart image PW, the light-receiving-amount output W in the non-color-mixture state is calculated.

Figure 34:
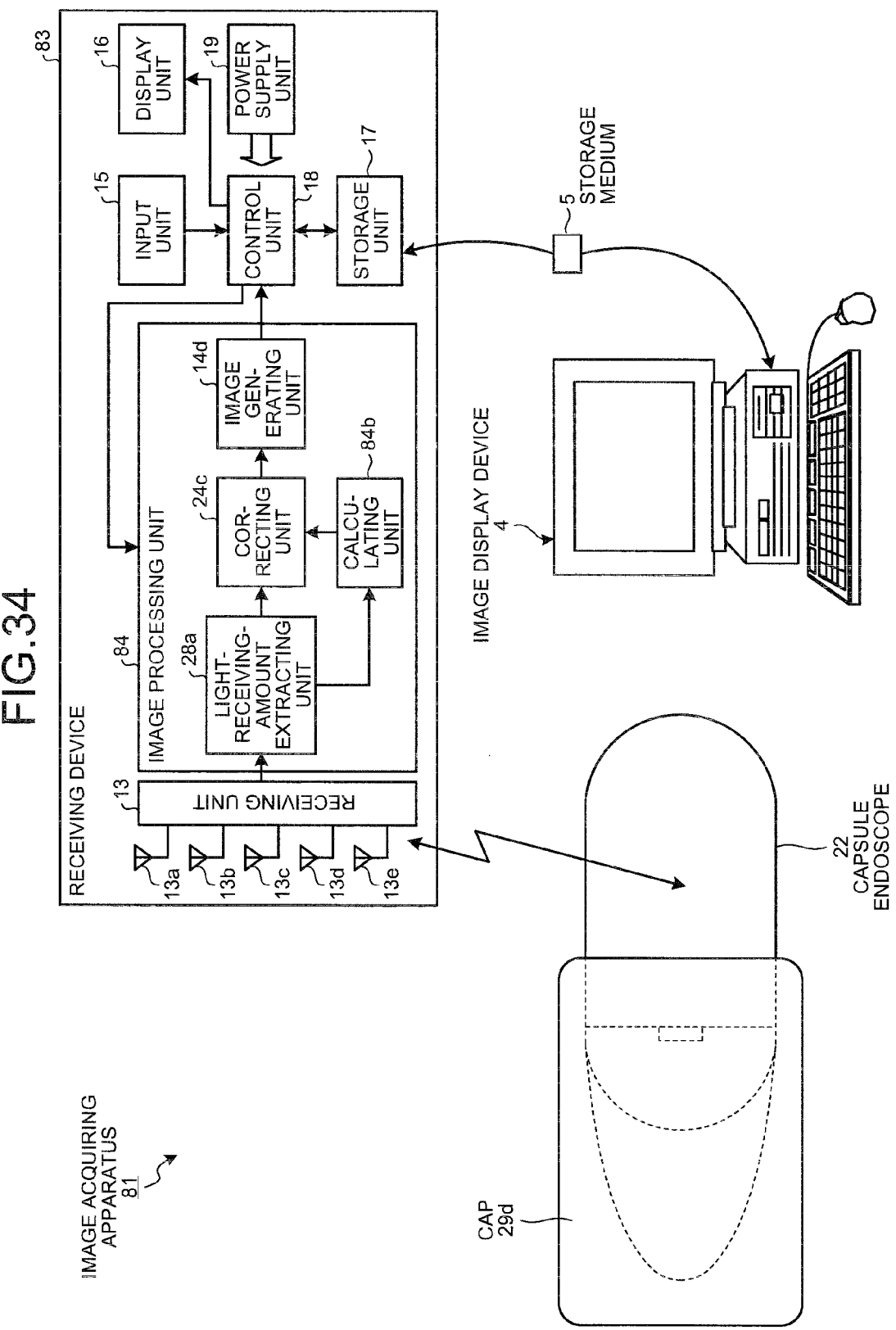
FIG. 34 is a block diagram schematically depicting a configuration example of an observation apparatus according to a sixth embodiment of the present invention.

FIG. 34 is a block diagram schematically depicting a configuration example of an observation apparatus according to the sixth embodiment of the present invention. As depicted in FIG. 34, an image acquiring apparatus 81, which is an observation apparatus according to the sixth embodiment, has the capsule endoscope 22 in place of the capsule endoscope 37 of the image acquiring apparatus 36 according to the modification example of the third embodiment described above, and a receiving device 83 in place of the receiving device 27. The receiving device 83 has an image processing unit 84 in place of the image processing unit 28 of the receiving device 27 described above. Other configurations are the same as those of the modification example of the third embodiment, and the same component units are provided with the same reference numerals.

As exemplified in the second embodiment described above, the capsule endoscope 22 simultaneously emits red light, green light, and blue light to a field of view to be captured of the imaging unit 9 to capture an image, and wirelessly transmits the captured image to the receiving device 83. The capsule endoscope 22 captures the chart image PW in a state where the cap 29d having the white chart 7d formed on its inner wall surface is mounted thereon, and wirelessly transmits the captured chart image PW to the receiving device 83. In a state of being inserted into an organ of the subject 100, the capsule endoscope 22 sequentially captures an in-vivo image of the subject 100 at predetermined intervals, and sequentially and wirelessly transmits the captured in-vivo image to the receiving device 83.

The image processing unit 84 of the receiving device 83 calculates the inverse matrix $M^{-1}$ of the color-mixture matrix M based on each transmittance of red light, green light, and blue light passing through the color filters of the plural colors formed on the pixels of the imaging unit 9 of the capsule endoscope 22. The image processing unit 84 uses thus calculated inverse matrix $M^{-1}$ to calculate the light-receiving-amount output W in the non-color-mixture state (the white-balance correction coefficient) and the gamma value. Other functions of the image processing unit 84 are approximately similar to those of the image processing unit 28 of the receiving device 27 described above.

The image processing unit 84 has a calculating unit 84b in place of the calculating unit 14b of the image processing unit 28 described above, and has the light-receiving-amount extracting unit 28a, the correcting unit 24c, and the image generating unit 14d, as with the image processing unit 28 described above.

The calculating unit 84b has wavelength bands $\Delta\lambda_1$, $\Delta\lambda_2$, and $\Delta\lambda_3$ of red light, green light, and blue light, respectively, emitted from the light-emitting units 8a to 8c of the capsule endoscope 22, and filter characteristics of color filters (the red filter FR, the green filter FG, and the blue filter FB) of the plural colors formed on the pixels of the imaging unit 9 of the capsule endoscope 22. Based on center wavelengths $\lambda_1$, $\lambda_2$, and $\lambda_3$ of these wavelength bands $\Delta\lambda_1$, $\Delta\lambda_2$, and $\Delta\lambda_3$ and the filter characteristics of the color filters of the plural colors, the calculating unit 84b calculates each of transmittances of red light, green light, and blue light passing through the color filters of the plural colors. Then, based on each calculated transmittance, the calculating unit 84b calculates the inverse matrix $M^{-1}$ of the color-mixture matrix M.

Figure 35A:
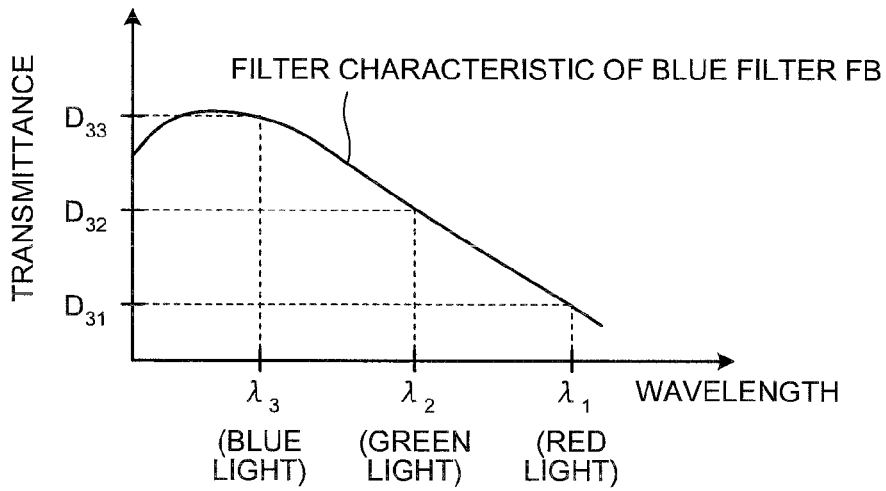
FIGS. 35A to 35C are schematic diagrams exemplifying a transmittance of each color light passing through color filers of plural colors formed for each pixel of an imaging unit.
Figure 35B:
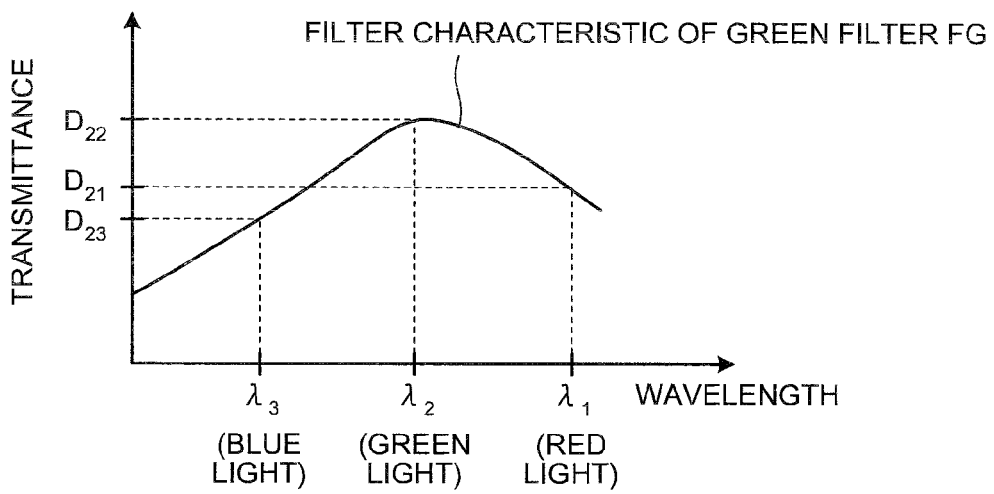
Figure 35C:
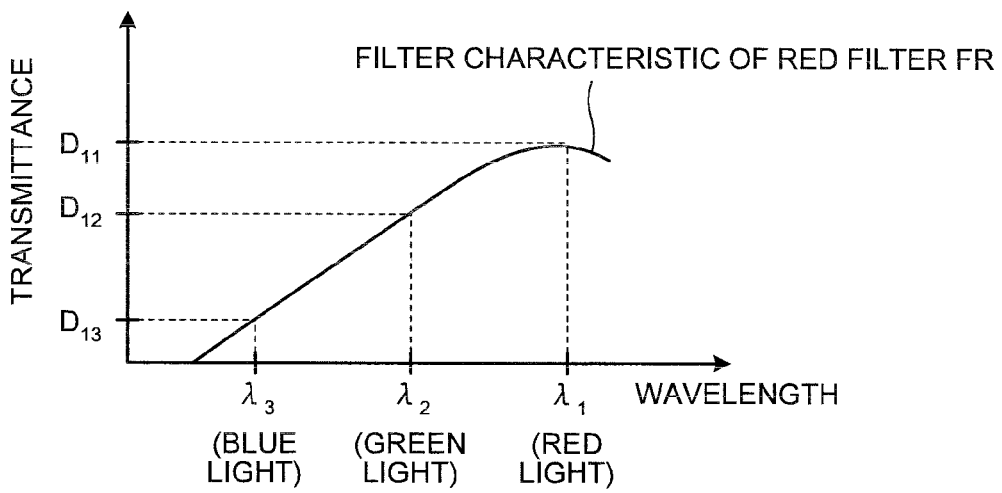

Specifically as depicted in FIGS. 35A to 35C, based on the each of the center wavelengths $\lambda_1$, $\lambda_2$, and $\lambda_3$ of red light, green light, and blue light and the filter characteristic of the red filter FR, the calculating unit 84b calculates a transmittance $D_{11}$ of red light, a transmittance $D_{21}$ of green light, and a transmittance $D_{31}$ of blue light that pass through the red filter FR. Also, based on the each of the center wavelengths $\lambda_1$, $\lambda_2$, and $\lambda_3$ of red light, green light, and blue light and the filter characteristic of the green filter FG, the calculating unit 84b calculates a transmittance $D_{21}$ of red light, a transmittance $D_{22}$ of green light, and a transmittance $D_{23}$ of blue light that pass through the green filter FG.

Furthermore, based on the each of the center wavelengths $\lambda_1$, $\lambda_2$, and $\lambda_3$ of red light, green light, and blue light and the filter characteristic of the blue filter FB, the calculating unit 84b calculates a transmittance $D_{31}$ of red light, a transmittance $D_{32}$ of green light, and a transmittance $D_{33}$ of blue light that pass through the blue filter FB.

The calculating unit 84b calculates the inverse matrix $M^{-1}$, with thus calculated transmittances $D_{11}$, $D_{21}$, and $D_{31}$ of red light, transmittances $D_{12}$, $D_{22}$, and $D_{32}$ of green light, and transmittances $D_{13}$, $D_{23}$, and $D_{33}$ of blue light as matrix elements of the color-mixture matrix M. The color-mixture matrix M calculated by the calculating unit 84b is a third-order square matrix that contains matrix elements of the same color filter in the same row and matrix elements of the same color light in the same column, and is represented by the following Equation (15):

$$M = \begin{pmatrix} k_1 D_{11} & k_2 D_{12} & k_3 D_{13} \\ k_1 D_{21} & k_2 D_{22} & k_3 D_{23} \\ k_1 D_{31} & k_2 D_{32} & k_3 D_{33} \end{pmatrix} \quad (15)$$

Also, the calculating unit 84b acquires, via the light-receiving-amount extracting unit 28, chart image information about the chart image PW captured by the capsule endoscope 22 and, based on the chart image information and the inverse matrix $M^{-1}$ (the inverse matrix of the color-mixture matrix represented by Equation (15)), calculates the light-receiving-amount output W in the non-color-mixture state (the white-balance correction coefficient). Furthermore, the calculating unit 84b uses the inverse matrix $M^{-1}$ to calculate the gamma value. The calculating unit 84b transmits the inverse matrix $M^{-1}$ (correction matrix), light-receiving-amount output W in the non-color-mixture state (white-balance correction coefficient), and gamma value calculated as described above to the correcting unit 24c.

As described in the foregoing, in the sixth embodiment of the present invention, based on each of the filter characteristics of the color filters of the plural colors formed on the pixels of the imaging unit and the light-emitting wavelength of each of the plural light-emitting units that simultaneously emit plural color lights, each of transmittances of the color lights of the plural colors that pass through the color filters of the plural colors is calculated. An inverse matrix (correction matrix) of a color-mixture matrix is calculated in advance, with each of the transmittances of the color lights of the plural colors being taken as a matrix element. By using white chart image information captured by the imaging unit and the inverse matrix of the color-mixture matrix, a white-balance correction coefficient is calculated. Other configuration is similar to that of the modification example of the third embodiment described above. Therefore, the inverse matrix of the color-mixture matrix can be calculated even without capturing chart images of plural colors, such as RGB. Thus, operations and effects similar to those of the modification example of the third embodiment described above can be obtained, and a simple observation apparatus and observation method capable of reducing some work for capturing chart images of plural colors can be provided.

Although in the first to sixth embodiments and each modification example thereof of the present invention, the observation apparatus (image acquiring apparatus) that has a capsule endoscope, in which plural light-emitting units that emit color lights of plural colors and an imaging unit are incorporated inside of a capsule casing, is exemplarily described, the invention is not limited thereto. Any observation apparatus even without having a capsule endoscope may long as apparatus simultaneously emits white light or color lights of plural colors forming a white light and acquires an object image.

Figure 36:
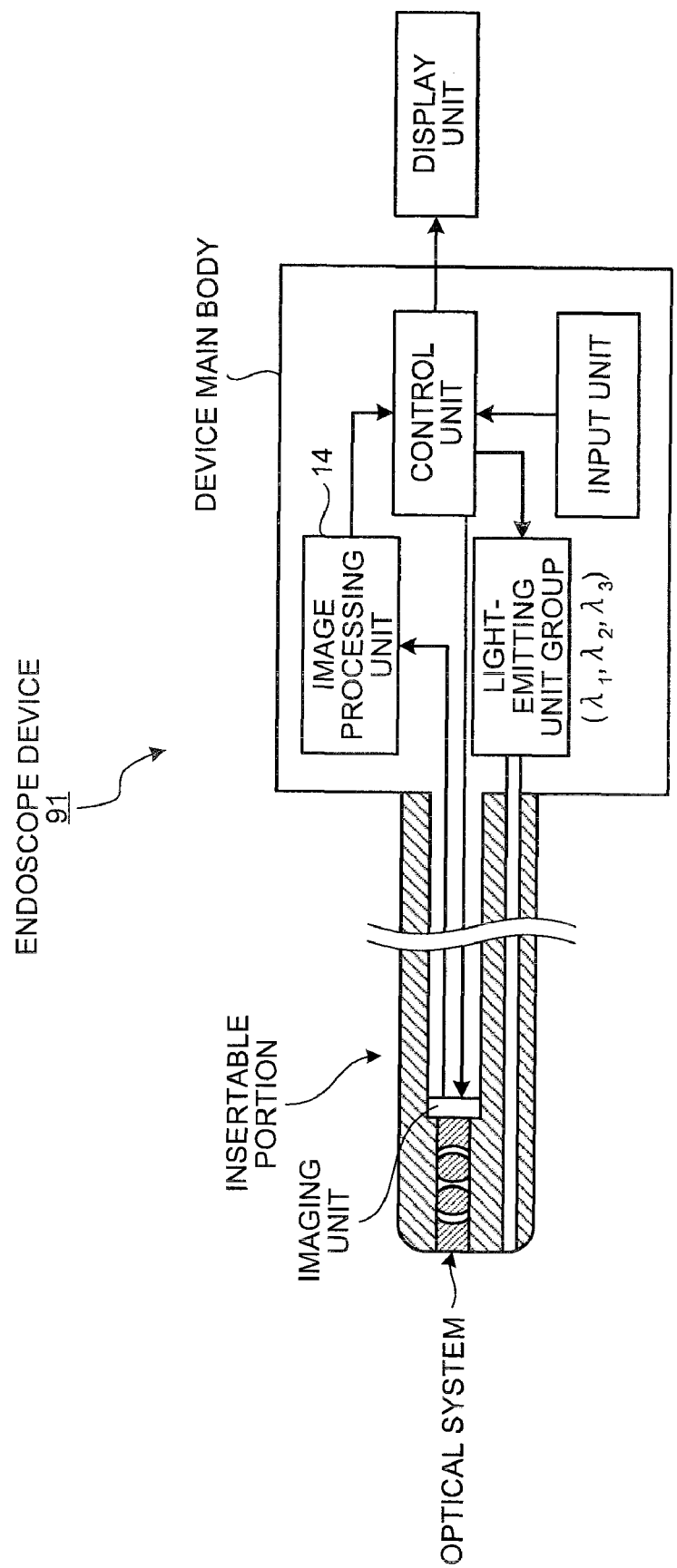
FIG. 36 is a schematic diagram exemplifying an endoscope apparatus to which the present invention is applied.

For example, as depicted in FIG. 36, the present invention may be applied to an endoscope apparatus 91 that has an optical system and an imaging unit incorporated in an insertable portion inserted inside an organ of a subject and acquires an image of the object (inside of the organ) illuminated with color lights of plural colors emitted from a light-emitting unit group incorporated in the apparatus main body. In this case, the endoscope apparatus 91 can have an input unit that inputs various instruction information for instructing a control unit, a display unit that displays a corrected object image, the control unit that controls each component unit, and an image processing unit (for example, the image processing unit 14 described above) that calculates various correction coefficients, such as the correction matrix and the white-balance correction coefficient described above and performs various correcting processes on the object image.

Figure 37:
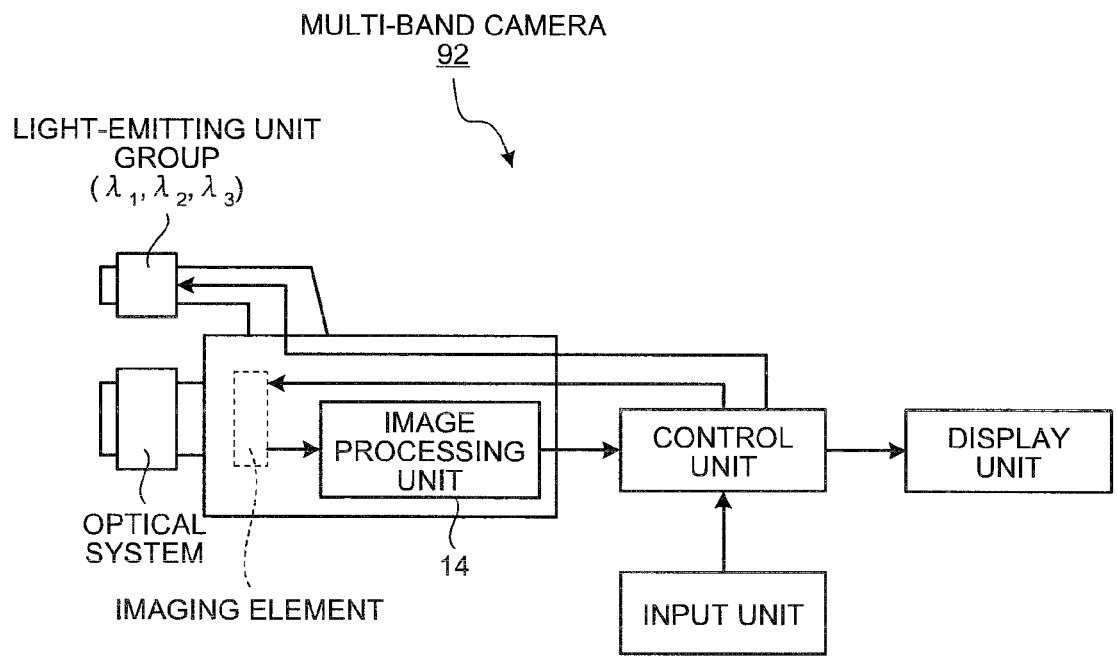
FIG. 37 is a schematic diagram exemplifying a multi-band camera to which the present invention is applied.
Figure 38:
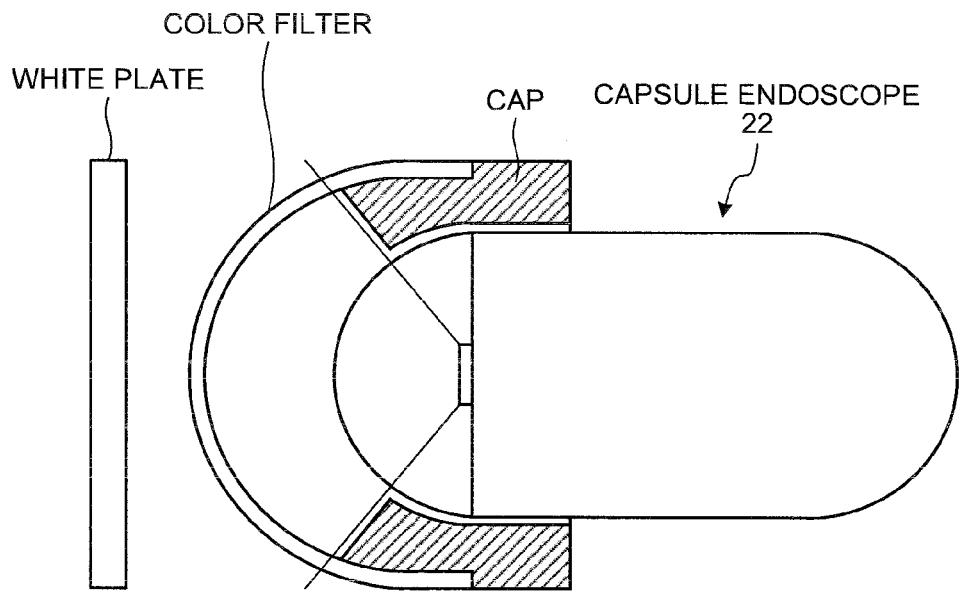
FIG. 38 is a schematic diagram exemplifying another mode of a cap to be mounted on the capsule endoscope of the modification example of the second embodiment of the present invention.

As depicted in FIG. 37, the present invention may be applied to a multi-band camera 92 that acquires an image of an object illuminated with color lights of plural colors emitted from a light-emitting unit group. In this case, the multi-band camera 92 can include a light-emitting unit group that emits color lights of plural colors, an optical system that forms an image of reflected light from an object, an imaging element that captures an image of the object illuminated by the light-emitting unit group, a display unit that displays a corrected object image, an input unit that inputs various instruction information to a control unit, the control unit that controls each component unit, and an image processing unit (for example, the image processing unit 14 described above) that calculates various correction coefficients, such as the correction matrix and the white-balance correction coefficient described above, and performs various correcting processes on the object image.

Although in the modification example of the second embodiment of the present invention, plural caps each having any of color components of color charts of plural colors including white (for example, the caps 29a to 29d) are sequentially mounted on a capsule endoscope to sequentially capture chart images of the plural colors for each frame, the invention is not limited thereto. Plural caps that have color filters of different colors may be sequentially mounted on the capsule endoscope, and reflected lights from a white plate may be received via the color filters of the caps to sequentially capture chart images of the plural colors for each frame. Such a cap has, covering an opening at one end, and a casing portion of the capsule endoscope 22 on an optical dome side is inserted from an opening at another end. The capsule endoscope 22 can have the plural caps that have respective color filters of different colors sequentially mounted thereon, and can receive reflected light from the white plate through the color filter of the mounted cap to sequentially capture chart images of the plural colors for each frame.

Although in the first to sixth embodiments and each modification example of the present invention, three light-emitting units 8a to 8c that emit red light, green light, and blue light, respectively, are provided, the invention is not limited thereto. Plural light-emitting units that emit color lights of color components other than RGB, such as cyan, magenta and yellow, may be provided. Alternatively, plural light-emitting units that emit color lights of plural color component including RGB may be provided. Alternatively, one or more light-emitting units that emit white light formed by combining color components of plural colors may be provided. In this case, the color-mixture matrix M calculated by the image processing unit of the observation apparatus according to the first to fifth embodiments and each modification example of the present invention contains, as matrix elements, a light-receiving-amount value $S_{ij}$ output for each pixel when color light of a wavelength $\lambda_j$ (j=1, 2, 3, ..., n) passes through a color filter of the pixel that should receive color light of a wavelength $\lambda_i$ (i=1, 2, 3, ..., n), and is represented by the following equation (16). On the other hand, the color-mixture matrix M calculated by the image processing unit of the observation apparatus according to the sixth embodiment of the present invention contains, as matrix elements, a transmittance $D_{ij}$ when color light of the wavelength $\lambda_j$ (j=1, 2, 3, ..., n) passes through the color filter of the pixel that should receive color light of the wavelength $\lambda_i$ (i=1, 2, 3, ..., n), and is represented by the following equation (17). Note that constants $k_1$, $k_2$, ..., $k_n$ of the color-mixture matrix M expressed in the following equations (16) and (17) are desired constants determined by the light-emitting amount of the light-emitting unit:

$$M = \begin{pmatrix} k_1 S_{11} & k_2 S_{12} & \ldots & k_n S_{1n} \\ k_1 S_{21} & k_2 S_{22} & \ldots & k_n S_{2n} \\ \vdots & \vdots & & \vdots \\ k_1 S_{n1} & k_2 S_{n2} & \ldots & k_n S_{nn} \end{pmatrix} \quad (16)$$

$$m = \begin{pmatrix} k_1 D_{11} & k_2 D_{12} & \ldots & k_n D_{1n} \\ k_1 D_{21} & k_2 D_{22} & \ldots & k_n D_{2n} \\ \vdots & \vdots & & \vdots \\ k_1 D_{n1} & k_2 D_{n2} & \ldots & k_n D_{nn} \end{pmatrix} \quad (17)$$

Although in the first to fifth embodiments and each modification example thereof of the present invention, the color-mixture matrix M is calculated based on the average light-receiving-amount value for pixel groups of color components corresponding to the chart images, the invention is not limited thereto. The color-mixture matrix M may be calculated based on a total light-receiving-amount value of the pixel groups of the color components corresponding to the chart images, or the color-mixture matrix M may be calculated based on an average light-receiving-amount value or a total light-receiving-amount value of a desired pixel group among the pixel groups corresponding to the chart images. Such a desired pixel group is desirably a pixel group near the center portion of an image of one frame containing the chart images, because this can prevent a color shift that tends to occur in a pixel group near an outer perimeter of the image due to an optical system.

Although in the first to sixth embodiments and each modification example thereof of the present invention, the color-mixture state, the white balance, or the like of the object image, such as an in-vivo image are corrected, the invention is not limited thereto. The observation apparatus according to the present invention may be any as long as the apparatus corrects at least the color-mixture state of the acquired object image.

Although in the first and second embodiments, the modification example of the second embodiment and the modification example of the fourth embodiment of the present invention, the plural light-emitting units $8a$ to $8c$ that emit different color lights (red light, green light, and blue light) are provided, the invention is not limited thereto. One or more light-emitting units that emit white light may be provided.

Although in the first to sixth embodiments and each modification example thereof of the present invention, the image processing unit that calculates various correction coefficients, such as the inverse matrix $M^{-1}$ of the color-mixture matrix M (correction matrix), to perform various correcting processes on the object image is incorporated in the receiving device, the invention is not limited thereto. This image processing unit may be incorporated in the image display device of the observation apparatus according to the present invention.

Although in the second and third embodiments and each modification example thereof of the present invention, chart images of plural colors are captured before examination of the subject, that is, before an in-vivo image of the subject is captured, to calculate the color-mixture matrix M, the invention is not limited thereto. Chart images of plural colors may be captured after examination of the subject, that is, after an in-vivo image of the subject is captured to calculate the color-mixture matrix M. Alternatively, chart images of plural colors may be captured before examination of the subject, and the chart images of the plural colors may be read during or after the examination of the subject, that is, during or after capturing of an in-vivo image of the subject, to calculate the color-mixture matrix M. In this case, an in-vivo image group before correction is saved in the storage unit in advance and, after the color-mixture matrix M is calculated, then various correcting processes can be performed on the in-vivo image group before correction.

Although in the second and third embodiments and each modification example thereof of the present invention, the light-receiving-amount extracting unit of the image processing unit described above identifies an in-vivo image and a chart image, the invention is not limited thereto. The image processing unit described above may be incorporated in the image display device of the observation apparatus according to the present invention, and a user, such as a doctor or nurse, may select a chart image displayed on the display unit of this image display device.

Although in the fifth embodiment and the first and second modification examples thereof of the present invention, in the process of assembling a capsule endoscope, a capsule endoscope in an incomplete state is used to capture chart images of plural colors, and various correction coefficients and the parameters for adjusting the light-emitting amount (each current value, each resistance value, or each light-emitting time described above) calculated by the image processing unit described above are input to the capsule endoscope in an incomplete state, the invention is not limited thereto. A completed capsule endoscope after completion of assembly may be used to capture chart images of plural colors, and various correction coefficients and the parameters for adjusting the light-emitting amount calculated by the image processing unit described above may be input to the completed capsule endoscope. In this case, the communicating unit of the capsule endoscope can be configured to enable bi-directional communications, and various correction coefficients and the parameters for adjusting the light-emitting amount calculated by the image processing unit can be transmitted to the capsule endoscope through wireless communication.

Although in the fourth and fifth embodiments and each modification example thereof of the present invention, various correction coefficients or the like calculated by the image processing unit described above are input to the capsule endoscope via the image display device, the invention is not limited thereto. Various correction coefficients or the like may be directly input from the receiving device to the capsule endoscope through wired communication via a cable or the like, or through wireless communication.

Although in the first to sixth embodiments and each modification example thereof of the present invention, for example, element lights of plural colors (different color lights) reflected from the color charts after emitted from the plural light-emitting units of the capsule endoscope and then received by the imaging unit are combined with each other to form white light, the invention is not limited thereto. The element lights of the plural colors are not necessarily required to form white light when simultaneously emitted (that is, when combined with each other). For example, a combination of colors of these element lights may be a combination of only blue and green. In this case, the white balance is taken in order to complete a balance for adjusting the light amount of each of the blue element light and the green element light, and not necessarily for adjustment so that the acquired image becomes white. The same goes to the case of another combination of colors of element lights of the plural colors.

Although in the first to sixth embodiments and each modification example thereof of the present invention, the red filter, the blue filter, and the green filter are provided in order to let the element light of each color pass through at a high transmittance, the invention is not limited thereto. Each color filter may be any as long as it is a filter assigned with a transmittance of each element light as a weight. In this case, as with the case of providing the red filter, the blue filter, and the green filter, by ascertaining the state of applying a weight of the transmittance to the element light of each color filter, components of each element light can be separated from the data acquired by the imaging unit.

Although in the first to sixth embodiments and each modification example thereof of the present invention, an imaging element is used as a light detecting unit that detects light reflected from the observation target, the invention is not limited thereto. A detecting unit may be used that detects a light amount by changing patterns of assigning a weight to each element light. This detecting unit can detect a value obtained by averaging optical components of the observation target at a specific position in the subject. The imaging element in the first to sixth embodiments and the modification examples can be said such that a plurality of such the detecting unit is provided.

According to the present invention, even without providing an imaging unit with a special filter that allows a color light of a narrow wavelength band to pass through, color lights of color-mixture components received by the imaging unit can be reliably eliminated when color lights of plural colors are simultaneously radiated to a subject in order to capture an image of the subject. As a result, image blurring due to the motion of the subject or the movement of the imaging unit can be reduced, and the capture frame rate can be increased. Also, a color mixture of the color components that occurs when color lights of plural wavelength bands are simultaneously received can be corrected. Thus, an effect of providing an observation apparatus and an observation method capable of acquiring a subject image that is excellent in color reproducibility can be attained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
    a light radiating unit that radiates a plurality of element lights, each of which has a limited wavelength band, to an observation target;
    a light detecting unit that detects the plurality of element lights reflected by the observation target in a plurality of patterns by changing a weight for each of the element lights; and
    a processing unit that performs a procedure of separating a component of each of the element lights from a plurality of detection results of the light detecting unit based on the weight for each of the element lights of the light detecting unit.

2. The observation apparatus according to claim 1, wherein the processing unit performs a process of multiplying a vector generated from the plurality of detection results of the light detecting unit by an inverse matrix of a matrix that is formed by arranging vectors for the respective patterns at the light detecting unit, each vector representing the weight for the element light in each detection result.

3. The observation apparatus according to claim 1, further comprising:
    a reflecting unit that reflects the lights radiated by the light radiating unit; and
    an element-light selecting unit that selectively allows a specific one of the element lights to enter the light detecting unit.

4. The observation apparatus according to claim 3, wherein the reflecting unit is provided on the element-light selecting unit, and
    the reflecting unit reflects only the specific one of the element lights.

5. The observation apparatus according to claim 1, further comprising:
    an imaging unit that acquires an image of the observation target, the imaging unit including a plurality of the light detecting units; and
    an element-light selecting unit having reflecting areas for the respective element lights on a same plane, the reflecting areas reflecting only the element lights.

6. The observation apparatus according to claim 5, wherein the element-light selecting unit is placed in front of the light radiating unit and the imaging unit, and includes a transparent portion that allows the lights radiated from the light radiating unit and the lights reflected by the observation target to pass through.

7. The observation apparatus according to claim 3, wherein the reflecting unit is white, and
    the element-light selecting unit is placed between the light radiating unit and the reflecting unit and is a filter that allows only the specific one of the elements light to pass through.

8. The observation apparatus according to claim 3, wherein the reflecting unit is white, and
    the element-light selecting unit controls the light radiating unit so that the light radiating unit radiates the element lights in a sequentially switching manner.

9. The observation apparatus according to claim 3, wherein the reflecting unit is white, and
    the element-light selecting unit includes:
    an instructing unit that makes an instruction for a selection from the element lights; and
    a control unit that controls the light radiating unit so that the light radiating unit radiates the element lights to be radiated in a switching manner based on the instruction from the instructing unit.

10. The observation apparatus according to claim 1, further comprising an imaging unit that acquires an image of the observation target, the imaging unit including a plurality of the light detecting units.

11. The observation apparatus according to claim 1, further comprising an element-light adjusting unit that adjusts a radiation amount for each of the element lights.

12. The observation apparatus according to claim 11, further comprising a white reflecting unit that is white, reflects the lights radiated from the light radiating unit, and is placed so that the light detecting unit detects the reflected lights, wherein
    the element-light adjusting unit adjusts a radiation amount of each of the element lights based on the process result of the processing unit obtained when the white reflecting unit is placed.

13. The observation apparatus according to claim 1, wherein the plurality of element lights form a white light.

14. An observation method comprising:
- simultaneously radiating a plurality of element lights, each of which has a limited wavelength band, to an observation target;
- measuring light amounts of the plurality of element lights reflected by the observation target in a plurality of patterns by changing a weight for each of the element lights; and
- separating a light amount of each of the element lights from the measured light amounts in the plurality of patterns based on the weight for each of the element lights used when measuring the light amount.

15. The observation method according to claim 14, further comprising measuring a weight of each of the element lights for each of the measurement patterns of the light amount.

16. The observation method according to claim 15, wherein the measuring the weight includes:
- separating an element light from the radiated plurality of element lights and reflecting the element light;
- measuring a light amount of the reflected element light in a plurality of patterns; and
- repeating the separating, reflecting and measuring the light amount while switching the element lights to be separated.

17. The observation method according to claim 15, wherein the measuring the weight includes:
- radiating only the element light;
- reflecting the radiated element light;
- measuring a light amount of the reflected element light in a plurality of patterns; and
- repeating the radiating, reflecting, and measuring the light amount while switching the element lights to be radiated.

18. The observation method according to claim 14, further comprising displaying the result of separating the light amount of the element light.

19. The observation method according to claim 14, further comprising storing the result of separating the light amount of the element light.

20. The observation method according to claim 14, wherein the measuring light amounts is a step of acquiring an image of the observation target illuminated with the radiated lights.

* * * * *